US009116137B1

(12) United States Patent
Gettings et al.

(10) Patent No.: US 9,116,137 B1
(45) Date of Patent: Aug. 25, 2015

(54) SELECTIVE ELECTRICAL COUPLING BASED ON ENVIRONMENTAL CONDITIONS

(71) Applicant: Leeo, Inc., Palo Alto, CA (US)

(72) Inventors: Adam M. Gettings, Red Wing, MN (US); Andrew G. Stevens, Palo Alto, CA (US); Bjorn H. Hovland, Woodside, CA (US); Yi Zheng, Palo Alto, CA (US); Lucas Ivers, Mountain View, CA (US); Nina S. Joshi, Saratoga, CA (US)

(73) Assignee: Leeo, Inc., Palo Alto, CA (US)

( * ) Notice: Subject to any disclaimer, the term of this patent is extended or adjusted under 35 U.S.C. 154(b) by 8 days.

(21) Appl. No.: 14/334,550

(22) Filed: Jul. 17, 2014

Related U.S. Application Data

(63) Continuation of application No. PCT/US2014/046748, filed on Jul. 15, 2014.

(51) Int. Cl.
*G01N 33/00* (2006.01)
*G05B 13/02* (2006.01)
*H02J 7/00* (2006.01)

(52) U.S. Cl.
CPC .......... *G01N 33/00* (2013.01); *G05B 13/02* (2013.01); *G05B 2219/2642* (2013.01); *H02J 7/0027* (2013.01)

(58) Field of Classification Search
CPC ........ H04L 63/10; G05B 15/02; G05B 13/02; G05B 2219/2642; G05B 19/042; G05B 19/418; G05B 19/4185; G05B 2219/23377; G05B 2219/25092; G05B 2219/25168; G05B 2219/2614; G05B 2219/2639; G05B 2219/33343; G05B 2219/34481; H02J 3/14; H02J 2003/143; G01N 33/00
USPC .............. 73/865.8; 307/31, 39, 112; 340/540, 340/501, 572.1, 628, 632, 3.1, 500, 506, 340/539.22; 702/188; 324/71.1
See application file for complete search history.

(56) References Cited

U.S. PATENT DOCUMENTS

| 4,093,867 A | 6/1978 | Shah et al. |
| 4,418,333 A | 11/1983 | Schwarzbach et al. |

(Continued)

FOREIGN PATENT DOCUMENTS

| EP | 1500955 | 1/2005 |
| GB | 2454731 | 5/2009 |

(Continued)

OTHER PUBLICATIONS

Carriazo-Osorio, Fernando, "Impacts of Air Pollution on Property Values: An Economic Valuation for Bogota, Colombia", http://www.demogr.mpg.de/papers/workshops/01 0518yaper02.pdf, Aug. 19, 2007.

(Continued)

*Primary Examiner* — Hezron E Williams
*Assistant Examiner* — Marrit Eyassu
(74) *Attorney, Agent, or Firm* — Steven Stupp; Hudak Consulting Group, LLC

(57) ABSTRACT

An environmental monitoring device that includes a switching mechanism is described. During operation of the environmental monitoring device, the switching mechanism (such as a switch) selectively electrically couples a first electrical-connection node and a second electrical-connection node. For example, using the switching mechanism, an electronic device that is electrically coupled to the first electrical-connection node may be selectively electrically coupled to a second electronic device that is electrically coupled to the second electrical-connection node. The selective electrical coupling may be based on one or more measurements of an environmental condition in an external environment that includes the environmental monitoring device. Moreover, a sensor mechanism in the environmental monitoring device may provide sensor data based on the one or more measurements. Alternatively, an antenna and an interface circuit in the environmental monitoring device may receive the sensor data from a third electronic device.

22 Claims, 26 Drawing Sheets

(56) References Cited

U.S. PATENT DOCUMENTS

| | | | |
|---|---|---|---|
| 4,450,436 A | 5/1984 | Massa | |
| 4,896,039 A | 1/1990 | Fraden | |
| 5,045,833 A | 9/1991 | Smith | |
| 5,156,203 A | 10/1992 | Funakoshi et al. | |
| 5,159,315 A * | 10/1992 | Schultz et al. | 340/539.26 |
| 5,532,660 A | 7/1996 | Smith et al. | |
| 5,623,197 A * | 4/1997 | Roseman et al. | 320/134 |
| 5,646,591 A | 7/1997 | Issa et al. | |
| 5,675,070 A | 10/1997 | Gelperin | |
| 5,801,297 A | 9/1998 | Mifsud et al. | |
| 6,023,223 A | 2/2000 | Baxter, Jr. | |
| 6,216,956 B1 | 4/2001 | Ehlers et al. | |
| 6,415,205 B1 | 7/2002 | Myron et al. | |
| 6,428,334 B1 | 8/2002 | Skarie et al. | |
| 6,492,907 B1 | 12/2002 | McCracken | |
| 6,672,129 B1 | 1/2004 | Frederickson et al. | |
| 6,753,776 B2 | 6/2004 | Drinkard | |
| 6,753,786 B1 | 6/2004 | Apperson et al. | |
| 6,759,763 B2 | 7/2004 | Barton | |
| 7,089,780 B2 | 8/2006 | Sunshine et al. | |
| 7,098,782 B1 | 8/2006 | Peckham et al. | |
| 7,116,213 B2 * | 10/2006 | Thiesen et al. | 340/10.1 |
| 7,257,397 B2 | 8/2007 | Shamoon et al. | |
| 7,304,259 B2 | 12/2007 | Schwarz et al. | |
| 7,337,078 B2 | 2/2008 | Bond et al. | |
| RE40,437 E | 7/2008 | Rosen | |
| 7,400,594 B2 | 7/2008 | Pereira et al. | |
| 7,515,041 B2 | 4/2009 | Eisold et al. | |
| 7,522,036 B1 | 4/2009 | Preuss et al. | |
| 7,764,180 B2 | 7/2010 | Huang | |
| 7,784,293 B2 | 8/2010 | Violand et al. | |
| 7,818,184 B2 | 10/2010 | Penny et al. | |
| 7,825,546 B2 | 11/2010 | Li et al. | |
| 7,905,154 B2 | 3/2011 | Jones | |
| 7,952,475 B2 | 5/2011 | Ivanov et al. | |
| 7,994,928 B2 | 8/2011 | Richmond | |
| 8,113,069 B2 | 2/2012 | Settles | |
| 8,125,194 B2 | 2/2012 | Nethken | |
| 8,170,722 B1 | 5/2012 | Elberbaum | |
| 8,224,576 B2 | 7/2012 | Jensen et al. | |
| 8,242,640 B2 | 8/2012 | Lee et al. | |
| 8,289,135 B2 | 10/2012 | Griffin | |
| 8,301,271 B2 | 10/2012 | Lee et al. | |
| 8,335,936 B2 | 12/2012 | Jonsson et al. | |
| 8,451,132 B1 | 5/2013 | Van Vleet | |
| 8,475,367 B1 | 7/2013 | Yuen et al. | |
| 8,489,437 B1 | 7/2013 | Dlott et al. | |
| 8,605,091 B2 | 12/2013 | Bradbury et al. | |
| 8,610,587 B2 | 12/2013 | Tropper | |
| 8,639,391 B1 | 1/2014 | Alberth, Jr. et al. | |
| 8,683,236 B2 | 3/2014 | Ukita et al. | |
| 2001/0007800 A1 | 7/2001 | Skarie et al. | |
| 2002/0011947 A1 | 1/2002 | Stolarczyk | |
| 2002/0050932 A1 | 5/2002 | Rhoades et al. | |
| 2002/0069076 A1 | 6/2002 | Faris et al. | |
| 2002/0097546 A1 | 7/2002 | Weinberger | |
| 2002/0152037 A1 | 10/2002 | Sunshine et al. | |
| 2003/0074092 A1 | 4/2003 | Carrabis | |
| 2003/0227220 A1 | 12/2003 | Biskup et al. | |
| 2004/0025604 A1 | 2/2004 | Call et al. | |
| 2004/0069046 A1 | 4/2004 | Sunshine et al. | |
| 2004/0075566 A1 | 4/2004 | Stepanik et al. | |
| 2004/0147038 A1 | 7/2004 | Lewis et al. | |
| 2004/0158193 A1 | 8/2004 | Bui et al. | |
| 2005/0136972 A1 | 6/2005 | Smith et al. | |
| 2005/0148890 A1 | 7/2005 | Hastings | |
| 2005/0229452 A1 | 10/2005 | Shimasaki | |
| 2006/0004492 A1 | 1/2006 | Terlson et al. | |
| 2006/0173580 A1 | 8/2006 | Desrochers et al. | |
| 2006/0250236 A1 | 11/2006 | Ackley et al. | |
| 2006/0250260 A1 | 11/2006 | Albert et al. | |
| 2007/0038334 A1 | 2/2007 | Chou et al. | |
| 2007/0061393 A1 | 3/2007 | Moore | |
| 2007/0155349 A1 | 7/2007 | Nelson et al. | |
| 2007/0168088 A1 | 7/2007 | Ewing et al. | |
| 2007/0173978 A1 | 7/2007 | Fein et al. | |
| 2007/0225868 A1 | 9/2007 | Terlson et al. | |
| 2007/0241615 A1 | 10/2007 | Goodrich | |
| 2007/0276548 A1 | 11/2007 | Uzunovic et al. | |
| 2007/0278285 A1 | 12/2007 | Ehrensvaerd | |
| 2008/0024089 A1 * | 1/2008 | Meng et al. | 320/128 |
| 2008/0097809 A1 | 4/2008 | Stroman et al. | |
| 2008/0106424 A1 | 5/2008 | Bouse | |
| 2008/0173817 A1 | 7/2008 | Goldstein et al. | |
| 2008/0211683 A1 | 9/2008 | Curt et al. | |
| 2008/0221714 A1 | 9/2008 | Schoettle | |
| 2008/0291036 A1 | 11/2008 | Richmond | |
| 2009/0054799 A1 | 2/2009 | Vrtis et al. | |
| 2009/0066513 A1 | 3/2009 | Kondo et al. | |
| 2009/0096620 A1 | 4/2009 | Kuo | |
| 2009/0141898 A1 | 6/2009 | Huang | |
| 2009/0157839 A1 | 6/2009 | Diederichs et al. | |
| 2009/0193578 A1 | 8/2009 | Jang et al. | |
| 2009/0195382 A1 | 8/2009 | Hall | |
| 2009/0225480 A1 | 9/2009 | Baxter | |
| 2009/0271013 A1 | 10/2009 | Chen | |
| 2009/0278868 A1 | 11/2009 | Nakahira et al. | |
| 2010/0025449 A1 | 2/2010 | Longobardi | |
| 2010/0090822 A1 | 4/2010 | Benson et al. | |
| 2010/0101264 A1 | 4/2010 | Nishino | |
| 2010/0145543 A1 | 6/2010 | Middlemiss | |
| 2010/0164742 A1 | 7/2010 | Anderson | |
| 2010/0235004 A1 | 9/2010 | Thind | |
| 2010/0249955 A1 | 9/2010 | Sitton | |
| 2010/0298957 A1 | 11/2010 | Sanchez Rocha et al. | |
| 2010/0306033 A1 | 12/2010 | Oved et al. | |
| 2010/0313748 A1 | 12/2010 | Schluter | |
| 2010/0318236 A1 | 12/2010 | Kilborn et al. | |
| 2011/0025499 A1 | 2/2011 | Hoy et al. | |
| 2011/0027626 A1 * | 2/2011 | Lattin | 429/50 |
| 2011/0108724 A1 | 5/2011 | Ewing et al. | |
| 2011/0187542 A1 | 8/2011 | Dittmer et al. | |
| 2011/0202193 A1 | 8/2011 | Craig et al. | |
| 2011/0216453 A1 | 9/2011 | Haines et al. | |
| 2011/0245988 A1 | 10/2011 | Ingels et al. | |
| 2011/0260851 A1 | 10/2011 | Richman | |
| 2011/0270458 A1 | 11/2011 | Liu | |
| 2011/0273283 A1 | 11/2011 | Schmuttor et al. | |
| 2011/0316355 A1 | 12/2011 | Gruber et al. | |
| 2012/0022886 A1 | 1/2012 | Ohnemus | |
| 2012/0023555 A1 | 1/2012 | Putterman | |
| 2012/0095610 A1 | 4/2012 | Chapel et al. | |
| 2012/0109398 A1 | 5/2012 | Bhakta | |
| 2012/0130544 A1 | 5/2012 | Mohan et al. | |
| 2012/0154126 A1 | 6/2012 | Cohn et al. | |
| 2012/0209634 A1 | 8/2012 | Ling et al. | |
| 2012/0265361 A1 | 10/2012 | Billingsley et al. | |
| 2012/0303554 A1 | 11/2012 | Osann | |
| 2012/0316661 A1 | 12/2012 | Rahman et al. | |
| 2012/0325023 A1 | 12/2012 | Calio et al. | |
| 2013/0006436 A1 | 1/2013 | Masters et al. | |
| 2013/0038470 A1 | 2/2013 | Niemeyer et al. | |
| 2013/0049466 A1 | 2/2013 | Adams | |
| 2013/0082817 A1 | 4/2013 | Gruenbacher et al. | |
| 2013/0083805 A1 | 4/2013 | Lu et al. | |
| 2013/0085609 A1 | 4/2013 | Barker | |
| 2013/0166089 A1 | 6/2013 | Craig et al. | |
| 2013/0174646 A1 | 7/2013 | Martin | |
| 2013/0184880 A1 | 7/2013 | McMahon | |
| 2013/0201033 A1 | 8/2013 | Cohn et al. | |
| 2013/0238153 A1 | 9/2013 | Warwick et al. | |
| 2013/0275148 A1 | 10/2013 | Attaluri et al. | |
| 2013/0289919 A1 | 10/2013 | Wilson et al. | |
| 2013/0338839 A1 | 12/2013 | Rogers et al. | |
| 2013/0339766 A1 | 12/2013 | Chen et al. | |
| 2014/0006506 A1 | 1/2014 | Frei et al. | |
| 2014/0025221 A1 | 1/2014 | Chapel et al. | |
| 2014/0028097 A1 | 1/2014 | Augur | |
| 2014/0032003 A1 | 1/2014 | Chapel et al. | |
| 2014/0046599 A1 | 2/2014 | Smith et al. | |
| 2014/0069131 A1 | 3/2014 | Masui | |
| 2014/0092765 A1 | 4/2014 | Agarwal | |
| 2014/0098445 A1 | 4/2014 | Hooper | |
| 2014/0099941 A1 | 4/2014 | Ji et al. | |

(56) References Cited

U.S. PATENT DOCUMENTS

| | | | |
|---|---|---|---|
| 2014/0100700 A1 | 4/2014 | Matsumoto et al. | |
| 2014/0156084 A1 | 6/2014 | Rahman et al. | |
| 2014/0188286 A1 | 7/2014 | Hunka | |
| 2014/0236372 A1 | 8/2014 | Ewing et al. | |
| 2014/0257572 A1 | 9/2014 | Mohan et al. | |
| 2014/0277869 A1* | 9/2014 | King et al. | 701/22 |

FOREIGN PATENT DOCUMENTS

| | | |
|---|---|---|
| WO | WO 2005/063006 | 7/2005 |
| WO | WO 2007/148299 | 12/2007 |

OTHER PUBLICATIONS

Hayashi et al., "A Network-Centric Approach to Sensor-data and Service Integration," Sep. 13-18, 2011, SICE Annual Conference, pp. 2037-2042.

Huang et al., "Pervasive, Secure Access to a Hierarchical Sensor-Based Healthcare Monitoring Architecture in Wireless Heterogeneous Networks," May 4, 2009, IEEE Journal on Selected Areas in Communications, vol. 27, No. 4, pp. 400-411.

Miyaho et al., "Sensor Network Management for Healthcare Applications," 2010, IEEE Computer Society, pp. 14-20.

"Consumer Safety Notice for Nest Protect: Smoke + CO Alarm," nest.com/letter-from-the-ceo/, May 22, 2014.

"Definition of Symptom," http://www.merriam-webster.com/medical/symptom, Apr. 23, 2009.

"For $129, the best smoke detector on the market," CNET, http://www.cnet.com/products/nest-protect/, Jul. 8, 2014.

"Guidance Regarding Methods for De-identification of Protected Health Information in Accordance with the Health Insurance Portability and Accountabiiity Act (HIPPA) Privacy Rule," Department of Health and Human Services, http://www.hhs.gov/ocr/privacy/hipaa/understanding/coveredentities/De-identification/guidance.html, Dec. 1, 2012.

"Nest Labs Recalls to Repair Nest Protect Smoke + CO Alarms Due to Failure to Sound Alert," http://www.cpsc.gov/en/Recalls/2014/Nest-Labs-Recalls-to-Repair-Nest-Protect-Smoke-CO-Alarms/, May 21, 2014.

"Privacy Protector: 6 Good Reasons to De-Identify Data," http://privacyguidance.com/blog/6-good-reasons-to-de-identify-data/, Mar. 2012.

"What is Nest Wave and how does it work?," support.nest.com/article/what-is-nest-wave-and-how-does-it-work/, Apr 4, 2014.

Brown, Rick, "Nest pulls Protect smoke detector from retail on safety issue," CNET, www.cnet.com, Apr. 3, 2014.

Chapter Five Global Positioning System, May 2013.

Internet Archive Way Back Machine Date confirmation for reference, Chapter Five Global Positioning system, Oct. 18, 2014.

McCracken, Harry, "Nest's Smoke Detector 'Recall' Doesn't Mean You Need to Send Yours Back," Tech Technologizer, www.time.com, May 21, 2014.

Mogg, Trevor, "Nest Recalls 440,000 Protect Smoke Alarms, Issues Software Update That Fixes Glitch," www.digital trends.com, May 21, 2014.

Nest Protect, Manual, Oct. 2013.

Noh et al., "Design of a Room Monitoring System for Wireless Sensor Networks", Jul. 2013, pp. 1-7.

* cited by examiner

SELECTIVE ELECTRICAL COUPLING BASED ON ENVIRONMENTAL CONDITIONS

CROSS-REFERENCE TO RELATED APPLICATION

This application is a continuation of International Application No. PCT/US14/46748, filed Jul. 15, 2014, which is incorporated by reference herein in its entirety.

BACKGROUND

1. Field

The described embodiments relate generally to an environmental monitoring device, and more specifically to techniques for monitoring environmental conditions in an environment and accordingly selectively electrically coupling electrical nodes in an environmental monitoring device.

2. Related Art

Trends in connectivity and in portable electronic devices are resulting in dramatic changes in people's lives. For example, the Internet now allows individuals access to vast amounts of information, as well as the ability to identify and interact with individuals, organizations and companies around the world. This has resulted in a significant increase in online financial transactions (which are sometimes referred to as 'ecommerce'). Similarly, the increasingly powerful computing and communication capabilities of portable electronic device (such as smartphones), as well as a large and growing set of applications, are accelerating these changes, providing individuals access to information at arbitrary locations and the ability to leverage this information to perform a wide variety of tasks.

Recently, it has been proposed these capabilities be included in other electronic devices that are located throughout our environments, including those that people interact with infrequently. In the so-called 'Internet of things,' it has been proposed that future versions of these so-called 'background' electronic devices be outfitted with more powerful computing capabilities and networking subsystems to facilitate wired or wireless communication. For example, the background electronic devices may include: a cellular network interface (LTE, etc.), a wireless local area network interface (e.g., a wireless network such as described in the Institute of Electrical and Electronics Engineers (IEEE) 802.11 standard or Bluetooth™ from the Bluetooth Special Interest Group of Kirkland, Wash.), and/or another type of wireless interface (such as a near-field-communication interface). These capabilities may allow the background electronic devices to be integrated into information networks, thereby further transforming people's lives.

However, the overwhelming majority of the existing background electronic devices in people's homes, offices and vehicles have neither enhanced computing capabilities (such as processor that can execute a wide variety of applications) nor networking subsystems. Given the economics of many market segments (such as the consumer market segment), these so-called 'legacy' background electronic devices (which are sometimes referred to as 'legacy electronic devices') are unlikely to be rapidly replaced. These barriers to entry and change are obstacles to widely implementing the Internet of things.

Furthermore, there remain many environments (such as the interiors of trucks, trains, boxes, etc.) that currently do not regularly include electronic devices. As a consequence, it may also be difficult to extend the advantages of connectivity and enhanced computing capabilities into these environments.

In addition, many of the existing background electronic devices used in people's homes, offices and vehicles are difficult to use. For example, the user interfaces in the existing background electronic devices are often outdated and cumbersome, which can make it challenging for users to select desired functionality. Alternatively, the existing background electronic devices may not currently have the desired functionality, and the user interfaces in the existing background electronic devices may not allow reprogramming or modification of capabilities of the existing background electronic devices. These limitations are often frustrating for users.

Hence, there is a need for an environmental monitoring device that addresses the above-described problems.

SUMMARY

A first group of described embodiments relates to an environmental monitoring device that includes a first electrical-connection node that electrically couples to an electronic device, and a second electrical-connection node that electrically couples to a second electronic device. Moreover, a switching mechanism (such as a switch) in the environmental monitoring device selectively electrically couples the first electrical-connection node and the second electrical-connection node. Furthermore, a control mechanism in the environmental monitoring device provides a control signal to the switching mechanism to selectively electrically couple the first electrical-connection node and the second electrical-connection node based on one or more measurements of an environmental condition in an external environment that includes the environmental monitoring device.

Note that the environmental monitoring device may include a sensor mechanism that provides sensor data based on the one or more measurements of the environmental condition. For example, the sensor mechanism may include: a temperature sensor, a humidity sensor, an acoustic sensor, a fire-detection sensor, a load-monitoring sensor, and/or a motion sensor.

In particular, the sensor mechanism may include the acoustic sensor and the environmental condition may include a sound in the external environment. In this example, the control mechanism may selectively electrically decouple the first electrical-connection node and the second electrical-connection node when the sound exceeds a threshold value, and may selectively electrically couple the first electrical-connection node and the second electrical-connection node when the sound is less than the threshold value. Thus, the control mechanism may change the control signal based on the presence or absence of the sound, such as during a telephone call.

Alternatively or additionally, the sensor mechanism may include the fire-detection sensor and the environmental condition may include presence of fire. In this example, the control mechanism may selectively electrically decouple the first electrical-connection node from the second electrical-connection node when the presence of fire is detected.

In another example, the sensor mechanism may include the load-monitoring sensor and the environmental condition may include an electrical characteristic associated with the electronic device and/or the second electronic device. Then, the control mechanism may selectively electrically decouple the first electrical-connection node from the second electrical-connection node when the electrical characteristic indicates a standby operating mode for the electronic device and/or the second electronic device. Alternatively or additionally, the selective electrical decoupling may occur when the electrical characteristic indicates a safety concern such as a fire hazard, a short circuit, a risk of electric shock or electrocution, etc.).

In some embodiments, the selective electrical coupling includes current-limited coupling between the first electrical-connection node and the second electrical-connection node.

Moreover, the selective electrical coupling may include selectively switching between a closed state of the switching mechanism and an open state of the switching mechanism. Alternatively, the selective electrical coupling may include an impedance value between the impedance values when the electrical coupling corresponds to the open state of the switching mechanism and when the electrical coupling corresponds to the closed state of the switching mechanism. Consequently, the control signal may correspond to a grey-scale value associated with the impedance value.

Note that the environmental monitoring device may be used in conjunction with a variety of electrical standards. Thus, the first electrical-connection node may correspond to a first electrical standard having a first root-mean-square voltage and the second electrical-connection node may correspond to a second electrical standard having a second root-mean-square voltage.

Furthermore, the environmental monitoring device may include one or more additional electrical-connection nodes. For example, there may be a third electrical-connection node, and the control signal may selectively electrically couple the first electrical-connection node and the third electrical-connection node based on the one or more measurements of the environmental condition. In some embodiments, the selective electrical coupling of the first electrical-connection node and the second electrical-connection node and the selective electrical coupling of the first electrical-connection node and the third electrical-connection node are independent of each other. Alternatively, the selective electrical coupling of the first electrical-connection node and the second electrical-connection node and the selective electrical coupling of the first electrical-connection node and the third electrical-connection node may depend on each other (such as concurrent or alternating electrical coupling).

While the environmental monitoring device may function independently or without direct communication with other electronic devices, in other embodiments the environmental monitoring device works in conjunction with one or more electronic devices that are remotely located from the environmental monitoring device. For example, the environmental monitoring device may include: an antenna, and an interface circuit that communicates with a third electronic device that is separate from the environmental monitoring device. This communication may include an identifier of the third electronic device, and the control mechanism may selectively electrically couple the first electrical-connection node and the second electrical-connection node based on the identifier. In some embodiments, this selective electrical coupling is based on a predefined preference of an individual associated with the identifier. Alternatively, the communication may include a preference of the individual, and the selective electrical coupling may be based on the preference.

Another embodiment provides a computer-program product for use in conjunction with the environmental monitoring device. This computer-program product may include instructions for at least some of the aforementioned operations performed by the environmental monitoring device.

Another embodiment provides a method for selectively electrically coupling the first electrical-connection node and the second electrical-connection node in the environmental monitoring device. During operation, the environmental monitoring device obtains one or more measurements of the environmental condition in the external environment that includes the environmental monitoring device. For example, the sensor mechanism may provide sensor data based on the one or more measurements of the environmental condition or the sensor data may be received from a remotely located electronic device. Then, a control mechanism in the environmental monitoring device provides the control signal to the switching mechanism in the environmental monitoring device to selectively electrically couple the first electrical-connection node and the second electrical-connection node based on the one or more measurements of the environmental condition.

A second group of described embodiments relates to an environmental monitoring device that includes a first electrical-connection node that electrically couples to an electronic device that includes a power source, and a second electrical-connection node that electrically couples to a second electronic device that includes a rechargeable battery. Moreover, a switching mechanism (such as a switch) in the environmental monitoring device selectively electrically couples the first electrical-connection node and the second electrical-connection node. Furthermore, a sensor mechanism in the environmental monitoring device provides sensor data based on one or more measurements of an environmental condition that is associated with charging of the rechargeable battery. Additionally, a control mechanism in the environmental monitoring device provides a control signal to the switching mechanism to selectively electrically couple the first electrical-connection node and the second electrical-connection node based on the one or more measurements of the environmental condition. The control mechanism also selects a charging mode of the rechargeable battery based on the one or more measurements of the environmental condition.

For example, the charging mode may include: a charging profile as a function of time that increases life of the rechargeable battery, a charging profile as a function of time that reduces a charging time of the rechargeable battery, and/or a charging profile as a function of time that reduces power consumption while charging the rechargeable battery.

Moreover, the control mechanism may determine information associated with one of the electronic device and the second electronic device based on the one or more measurements of the environmental condition during operation of the one of the electronic device and the second electronic device. For example, the environmental condition may be associated with a power-up transient signal of the electronic device and/or the second electronic device. In addition, the information may be determined based on a predefined device profile. Note that the information may include: a type of electronic device, a model of electronic device, a brand of electronic device, and/or a unique identifier of the one of the electronic device and the second electronic device.

In some embodiments, the control mechanism predicts failure of at least a component in one of the electronic device and the second electronic device based on the one or more measurements of the environmental condition as a function of time. The predicted failure may be based on the determined information.

Furthermore, the control mechanism may associate a user with the determined information based a predefined list of electronic devices of the user. Then, the selective electrical coupling of the first electrical-connection node and the second electrical-connection node may be based on a predefined preference of the user.

Additionally, the sensor mechanism may include a load-monitoring sensor and the environmental condition may include an electrical characteristic associated with the electronic device and/or the second electronic device. Then, the control mechanism may selectively electrically decouple the first electrical-connection node from the second electrical connection node when the electrical characteristic indicates a standby operating mode for the electronic device and/or the second electronic device. Alternatively or additionally, the selective electrical decoupling may occur when the electrical characteristic indicates a safety concern (such as a fire hazard, a short circuit, a risk of electric shock or electrocution, etc.). Note that the electrical characteristic may include: a current, a voltage, a phase relative to at least a reference signal, a quality factor, a harmonic of a fundamental frequency, a resonance frequency, a time constant, noise, and/or power consumption.

Another embodiment provides a computer-program product for use in conjunction with the environmental monitoring device. This computer-program product may include instructions for at least some of the aforementioned operations performed by the environmental monitoring device.

Another embodiment provides a method for selectively electrically coupling the first electrical-connection node and the second electrical-connection node in the environmental monitoring device. During operation, the environmental monitoring device receives the sensor data based on the one or more measurements of the environmental condition from the sensor mechanism in the environmental monitoring device, where the environmental condition is associated with the charging of the rechargeable battery. Then, a control mechanism in the environmental monitoring device provides the control signal to the switching mechanism in the environmental monitoring device to selectively electrically couple the first electrical-connection node and the second electrical-connection node based on the one or more measurements of the environmental condition. Moreover, the control mechanism selects the charging mode of the rechargeable battery based on the one or more measurements of the environmental condition.

A third group of described embodiments relates to an environmental monitoring device that includes a first electrical-connection node that electrically couples to an electronic device, and a second electrical-connection node that electrically couples to a second electronic device. Moreover, a switching mechanism (such as a switch) in the environmental monitoring device selectively electrically couples the first electrical-connection node and the second electrical-connection node. Furthermore, an antenna and an interface circuit in the environmental monitoring device communicate with a third electronic device that is separate from the environmental monitoring device, where the communication includes sensor data based on one or more measurements by a sensor mechanism in the third electronic device of an environmental condition in an external environment that includes the environmental monitoring device. Additionally, a control mechanism in the environmental monitoring device provides a control signal to the switching mechanism to selectively electrically couple the first electrical-connection node and the second electrical-connection node based on the one or more measurements of the environmental condition.

Note that the sensor data may include: temperature, humidity, acoustic information, fire-detection information, load-monitoring information, and/or motion information. For example, the sensor data may include acoustic information and the environmental condition may include a sound in the external environment. Then, the control mechanism may selectively electrically decouple the first electrical-connection node and the second electrical-connection node when the sound exceeds a threshold value, and may selectively electrically couple the first electrical-connection node and the second electrical-connection node when the sound is less than the threshold value. Thus, the control mechanism may change the control signal based on the presence or absence of the sound, such as during a telephone call.

Alternatively or additionally, the sensor data may include the fire-detection information and the environmental condition may include presence of fire. In this example, the control mechanism may selectively electrically decouple the first electrical-connection node from the second electrical-connection node when the presence of fire is detected.

In another example, the sensor data may include the load-monitoring information and the environmental condition may include an electrical characteristic associated with the electronic device and/or the second electronic device. Then, the control mechanism may selectively electrically decouple the first electrical-connection node from the second electrical-connection node when the electrical characteristic indicates a standby operating mode for the electronic device and/or the second electronic device. Alternatively or additionally, the selective electrical decoupling may occur when the electrical characteristic indicates a safety concern (such as a fire hazard, a short circuit, a risk of electric shock or electrocution, etc.).

In some embodiments, the selective electrical coupling includes current-limited coupling between the first electrical-connection node and the second electrical-connection node.

Moreover, the selective electrical coupling may include selectively switching between a closed state of the switching mechanism and an open state of the switching mechanism. Alternatively, the selective electrical coupling may include an impedance value between the impedance values when the electrical coupling corresponds to the open state of the switching mechanism and when the electrical coupling corresponds to the closed state of the switching mechanism. Consequently, the control signal may correspond to a grey-scale value associated with the impedance value.

Note that the environmental monitoring device may be used in conjunction with a variety of electrical standards. Thus, the first electrical-connection node may correspond to a first electrical standard having a first root-mean-square voltage and the second electrical-connection node may correspond to a second electrical standard having a second root-mean-square voltage.

Furthermore, the environmental monitoring device may include one or more additional electrical-connection nodes. For example, there may be a third electrical-connection node, and the control signal may selectively electrically couple the first electrical-connection node and the third electrical-connection node based on the one or more measurements of the environmental condition. In some embodiments, the selective electrical coupling of the first electrical-connection node and the second electrical-connection node and the selective electrical coupling of the first electrical-connection node and the third electrical-connection node are independent of each other. Alternatively, the selective electrical coupling of the first electrical-connection node and the second electrical-connection node and the selective electrical coupling of the first electrical-connection node and the third electrical-connection node may depend on each other (such as concurrent or alternating electrical coupling).

In some embodiments, the communication includes an identifier of the third electronic device, and the control mechanism selectively electrically couples the first electrical-connection node and the second electrical-connection node based on the identifier. For example, the control mechanism may be associated the identifier with a predefined preference of an individual, and the selective electrical coupling may be based on the predefined preference. Alternatively, the communication may include a preference of the individual, and the selective electrical coupling may be based on the preference.

Another embodiment provides a computer-program product for use in conjunction with the environmental monitoring device. This computer-program product may include instructions for at least some of the aforementioned operations performed by the environmental monitoring device.

Another embodiment provides a method for selectively electrically coupling the first electrical-connection node and the second electrical-connection node in the environmental monitoring device. During operation, the environmental monitoring device receives, from another electronic device (such as the third electronic device), the sensor data based on the one or more measurements of the environmental condition in the external environment that includes the environmental monitoring device. Then, a control mechanism in the environmental monitoring device provides the control signal to the switching mechanism in the environmental monitoring device to selectively electrically couple the first electrical-connection node and the second electrical-connection node based on the one or more measurements of the environmental condition.

A fourth group of described embodiments relates to an environmental monitoring device that includes a first electrical-connection node that electrically couples to an electronic device, and a second electrical-connection node that electrically couples to a second electronic device. Moreover, a switching mechanism (such as a switch) in the environmental monitoring device selectively electrically couples the first electrical-connection node and the second electrical-connection node. Furthermore, an antenna and an interface circuit in the environmental monitoring device communicate with a third electronic device that is separate from the environmental monitoring device, where the communication includes location information of an individual. Additionally, a control mechanism in the environmental monitoring device provides a control signal to the switching mechanism to selectively electrically couple the first electrical-connection node and the second electrical-connection node based on one or more measurements of an environmental condition in an external environment that includes the environmental monitoring device and the location information.

For example, the selective electrical coupling may occur when the location information indicates that the individual is within a region. This region may include the external environment. Note that the location information may be based on triangulation and trilateration. Moreover, the location information may be based on: communication in a network, a local positioning system, and/or a Global Positioning System. Furthermore, the location information may specify the location of the individual in two dimensions and/or three dimensions. Additionally, the location information may include: an absolute position of the individual and/or a position of the individual relative to that of the environmental monitoring device.

In some embodiments, the control mechanism calculates, based on the location information, a predicted location of the individual and a time when the individual is estimated to be proximate to the location. Then, the selective electrical coupling may be based on the predicted location and the time.

Moreover, the communication may include an identifier of the third electronic device, and the control mechanism may selectively electrically couple the first electrical-connection node and the second electrical-connection node based on the identifier. In some embodiments, this selective electrical coupling is based on a predefined preference of an individual associated with the identifier. Alternatively, the communication may include a preference of the individual, and the selective electrical coupling may be based on the preference.

Furthermore, the environmental monitoring device may include a sensor mechanism that provides sensor data based on the one or more measurements of the environmental condition. Alternatively, the interface circuit may communicate with a fourth electronic device that is separate from the environmental monitoring device, and which includes the sensor mechanism that provides the sensor data based on the one or more measurements of the environmental condition. In these embodiments, the communication includes the sensor data.

Another embodiment provides a computer-program product for use in conjunction with the environmental monitoring device. This computer-program product may include instructions for at least some of the aforementioned operations performed by the environmental monitoring device.

Another embodiment provides a method for selectively electrically coupling the first electrical-connection node and the second electrical-connection node in the environmental monitoring device. During operation, the environmental monitoring device receives, from another electronic device (such as the third electronic device), the location information of the individual. Then, a control mechanism in the environmental monitoring device provides the control signal to the switching mechanism in the environmental monitoring device to selectively electrically couple the first electrical-connection node and the second electrical-connection node based on the one or more measurements of the environmental condition and the location information.

A fifth group of described embodiments relates to an environmental monitoring device that includes a first electrical-connection node that electrically couples to an electronic device, and a second electrical-connection node that electrically couples to a second electronic device. Moreover, a switching mechanism (such as a switch) in the environmental monitoring device selectively electrically couples the first electrical-connection node and the second electrical-connection node. Furthermore, a sensor mechanism in the environmental monitoring device provides sensor data based on one or more measurements of an environmental condition that corresponds to (or may be related to or a function of) power consumption by the electronic device and/or the second electronic device. An antenna and an interface circuit in the environmental monitoring device communicate with a third electronic device that is separate from the environmental monitoring device, where the communication includes the environmental condition. Additionally, a control mechanism in the environmental monitoring device provides a control signal to the switching mechanism to selectively electrically couple the first electrical-connection node and the second electrical-connection node based on the one or more measurements of the environmental condition.

For example, the environmental condition may include energy consumption and/or power consumption. Moreover, the environmental condition may indicate, during a time interval, usage of the electronic device and/or the second electronic device (such as whether or not the electronic device and/or the second electronic device were used). Alternatively or additionally, the environmental condition may indicate a duration of usage of the electronic device and/or the second electronic device.

In some embodiments, the sensor mechanism includes a load-monitoring sensor and the environmental condition includes an electrical characteristic associated with the electronic device and/or the second electronic device. For example, the electrical characteristic may include: a current, a voltage, a phase relative to at least a reference signal, a quality factor, a harmonic of a fundamental frequency, a resonance frequency, a time constant, noise, and/or power consumption. Moreover, the environmental condition may be associated with a power-up transient signal of the electronic device and/or the second electronic device. In particular, the electrical characteristic may include a time-varying power consumption of the electronic device and/or the second electronic device, where the time variation may include a sequence of approximately discrete values (such as two power-consumption levels or multiple power-consumption levels). Furthermore, the electrical characteristic may correspond to (or be related to or a function of): a pulse-code modulation sequence, a quadrature-modulation sequence, and/or a DC-balanced sequence.

In some embodiments, the selective electrical decoupling occurs when the electrical characteristic indicates a safety concern (such as a fire hazard, a short circuit, a risk of electric shock or electrocution, etc.).

Moreover, the control mechanism may determine information associated with one of the electronic device and the second electronic device based on the one or more measurements environmental condition during operation of the one of the electronic device and the second electronic device. For example, the information may include: a type of electronic device, a model of electronic device, a brand of electronic device, and/or a unique identifier of the one of the electronic device and the second electronic device. Furthermore, the control mechanism may associate a user with the determined information based a predefined list of electronic devices of the user. Alternatively or additionally, the selective electrical coupling may be based on a predefined preference of the user.

Another embodiment provides a computer-program product for use in conjunction with the environmental monitoring device. This computer-program product may include instructions for at least some of the aforementioned operations performed by the environmental monitoring device.

Another embodiment provides a method for selectively electrically coupling the first electrical-connection node and the second electrical-connection node in the environmental monitoring device. During operation, the environmental monitoring device receives, from the sensor mechanism in the environmental monitoring device, the sensor data based on the one or more measurements of an environmental condition in the external environment that includes the environmental monitoring device, where the environmental condition corresponds to power consumption by the second electronic device that is separate from the environmental monitoring device, and that is electrically coupled to the second electrical-connection node. Then, a control mechanism in the environmental monitoring device provides the control signal to the switching mechanism in the environmental monitoring device to selectively electrically couple the first electrical-connection node and the second electrical-connection node based on the one or more measurements of the environmental condition.

A sixth group of described embodiments relates to an environmental monitoring device that includes a first electrical-connection node that electrically couples to an electronic device, and a second electrical-connection node that electrically couples to a second electronic device. Moreover, a switching mechanism (such as a switch) in the environmental monitoring device selectively electrically couples the first electrical-connection node and the second electrical-connection node. Furthermore, a control mechanism in the environmental monitoring device provides a control signal to the switching mechanism to selectively electrically couple the first electrical-connection node and the second electrical-connection node based on one or more measurements of an environmental condition in an external environment that includes the environmental monitoring device. Additionally, an override mechanism in the environmental monitoring device specifies an electrical coupling state of the first electrical-connection node and the second electrical-connection node, where the electrical coupling state specified by the override mechanism supersedes the selective electrical coupling specified by the control signal.

Note that the override mechanism may supersede the selective electrical coupling either directly or indirectly. For example, the override mechanism may be electrically coupled to the switching mechanism and/or the control mechanism.

Moreover, the override mechanism may have a first electrical coupling state and a second electrical coupling state, and may include a switch and/or a button. In a first electrical coupling state of the override mechanism, the first electrical-connection node and the second electrical-connection node may be electrically coupled, and in a second electrical coupling state of the override mechanism the first electrical-connection node and the second electrical-connection node may be electrically decoupled.

Furthermore, the environmental monitoring device may include a sensor mechanism that provides sensor data based on the one or more measurements of the environmental condition. Alternatively or additionally, the environmental monitoring device includes an antenna and an interface circuit that communicate with a third electronic device that is separate from the environmental monitoring device. This communication may include the sensor data based on the one or more additional measurements, provided by the third electronic device, of the environmental condition, where the sensor data is associated with the sensor mechanism in the third electronic device. Note that the sensor mechanism may include: a temperature sensor, a humidity sensor, an acoustic sensor, a fire-detection sensor, a load-monitoring sensor, and/or a motion sensor.

In some embodiments, the environmental monitoring device includes a safety mechanism that detects a safety condition and decouples the first electrical-connection node and the second electrical-connection node. For example, the safety mechanism may include an insertion sensor that detects insertion of an object other than a plug into a socket associated with the first electrical-connection node and/or the second electrical-connection node. Moreover, the insertion sensor may include: an optical detector, a pressure sensor (such as a spring), a chemical sensor, and/or an electrical sensor.

Furthermore, the safety condition may involve detecting: insertion of the object into a hot contact associated with the socket; and/or a ground-fault current.

Additionally, the socket may have a first hole and a second hole, and the safety condition may involve detecting insertion of the object into the first hole without insertion of the object into the second hole. The detection of the insertion of the object into the first hole and the absence of detection of the insertion of the object into the second hole may be within a time interval.

Another embodiment provides a computer-program product for use in conjunction with the environmental monitoring device. This computer-program product may include instructions for at least some of the aforementioned operations performed by the environmental monitoring device.

Another embodiment provides a method for selectively electrically coupling the first electrical-connection node and the second electrical-connection node in the environmental monitoring device. During operation, the environmental monitoring device obtains the one or more measurements of the environmental condition in the external environment that includes the environmental monitoring device. Then, the control mechanism in the environmental monitoring device provides the control signal to the switching mechanism in the environmental monitoring device to selectively electrically couple the first electrical-connection node and the second electrical-connection node based on the one or more measurements of the environmental condition. Next, the override mechanism specifies the electrical coupling state of the first electrical-connection node and the second electrical-connection node, where the electrical coupling state specified by the override mechanism supersedes the selective electrical coupling specified by the control signal.

The preceding summary is provided as an overview of some exemplary embodiments and to provide a basic understanding of aspects of the subject matter described herein. Accordingly, the above-described features are merely examples and should not be construed as narrowing the scope or spirit of the subject matter described herein in any way. Other features, aspects, and advantages of the subject matter described herein will become apparent from the following Detailed Description, Figures, and Claims.

BRIEF DESCRIPTION OF THE FIGURES

Note that like reference numerals refer to corresponding parts throughout the drawings. Moreover, multiple instances of the same part are designated by a common prefix separated from an instance number by a dash.

DETAILED DESCRIPTION

Figure 1:
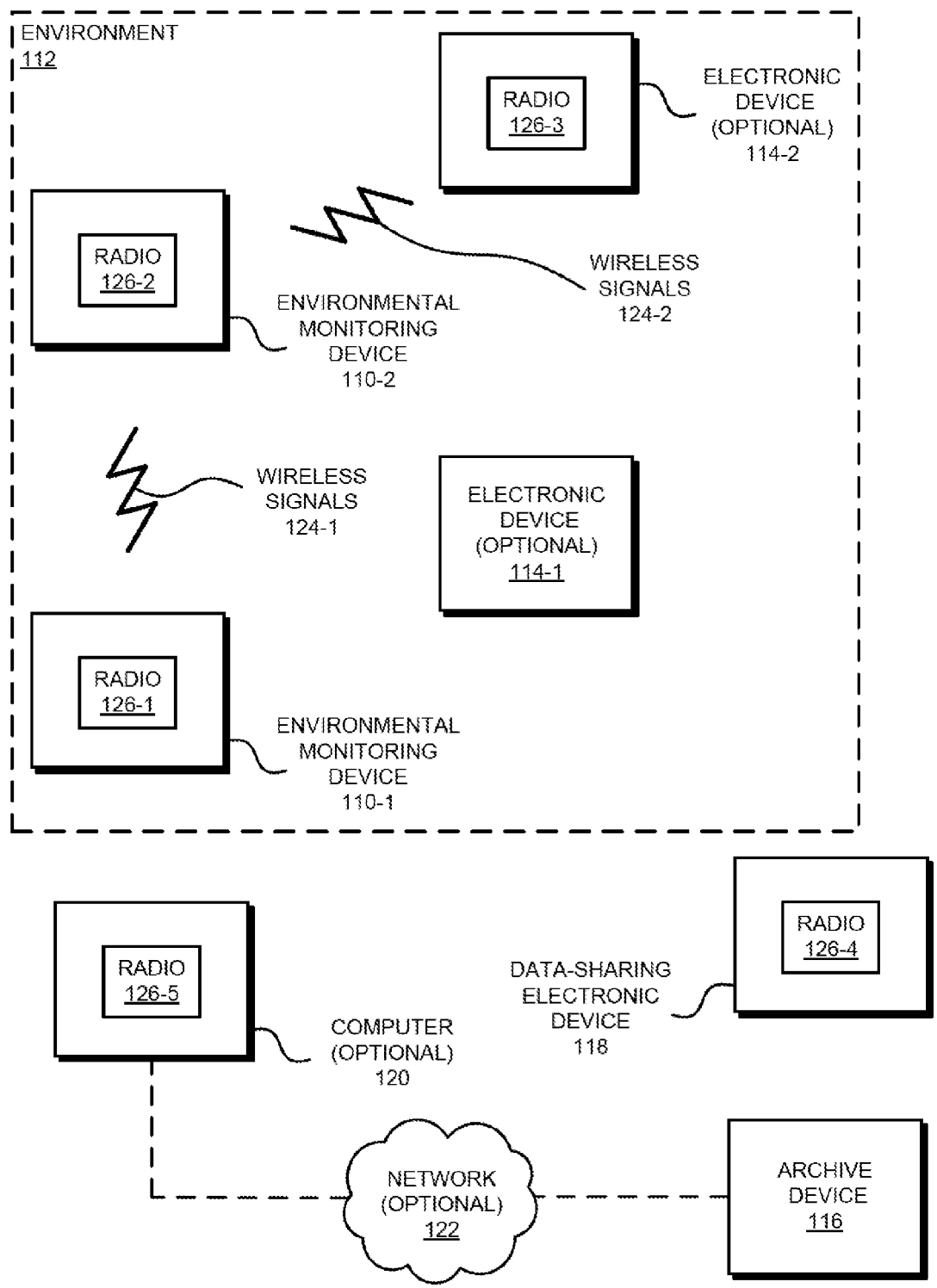
FIG. 1 is a block diagram illustrating electronic devices communicating in accordance with an embodiment of the present disclosure.

In one group of embodiments, an environmental monitoring device that includes a switching mechanism is described. During operation of the environmental monitoring device, the switching mechanism (such as a switch) selectively electrically couples a first electrical-connection node and a second electrical-connection node. For example, using the switching mechanism, an electronic device that is electrically coupled to the first electrical-connection node may be selectively electrically coupled to a second electronic device that is electrically coupled to the second electrical-connection node. The selective electrical coupling may be based on one or more measurements of an environmental condition in an external environment that includes the environmental monitoring device. Moreover, a sensor mechanism in the environmental monitoring device may provide sensor data based on the one or more measurements. Alternatively, an antenna and an interface circuit in the environmental monitoring device may receive the sensor data from a third electronic device.

In this way, the environmental monitoring device facilitates switching based on the environmental condition in the environment. For example, when a sound is present, a fire is detected, or an electrical characteristic of one of the electronic device and the second electronic device indicates a safety concern (such as a fire hazard, a short circuit, a risk of electric shock or electrocution, etc.), the first electrical-connection node may be electrically decoupled from the second electrical-connection node. Consequently, the environmental monitoring device may allow the switch state (i.e., the selective electrical coupling) to be dynamically adapted based on changing environmental conditions. This capability may allow the environmental monitoring device to work in conjunction with legacy electronic devices (i.e., without direct electrical coupling of instructions or without communication with the legacy electronic devices) and/or in conjunction with electronic devices that communicate directly with or that are electrically coupled to the environmental monitoring device. Thus, the environmental monitoring device may offer improved functionality and services, thereby promoting sales of the environmental monitoring device (and, more generally, commercial activity) and enhancing customer satisfaction with the environmental monitoring device.

In a second group of embodiments, an environmental monitoring device that includes a switching mechanism is described. During operation of the environmental monitoring device, the switching mechanism (such as a switch) selectively electrically couples a first electrical-connection node and a second electrical-connection node. For example, using the switching mechanism, an electronic device having a power source may be selectively electrically coupled to a second electronic device having a rechargeable battery. The selective electrical coupling may be based on one or more measurements of an environmental condition in an external environment that includes the environmental monitoring device by a sensor mechanism in the environmental monitoring device. This environmental condition may be associated with charging of the rechargeable battery. In addition, a control mechanism in the environmental monitoring device selects a charging mode of the rechargeable battery based on the one or more measurements of the environmental condition.

In this way, the environmental monitoring device facilitates switching based on the charging of the rechargeable battery (such as a charging state of the rechargeable battery). For example, this capability may allow the environmental monitoring device to: increase or maximize the life of the rechargeable battery, reduce or minimize the charging time, and/or reduce or minimize energy consumption during the charging. Moreover, the environmental monitoring device may allow the rechargeable battery to be safely charged, e.g., by identifying a safety concern (such as a fire hazard, a short circuit, a risk of electric shock or electrocution, etc.). In addition, the environmental monitoring device may allow the impending failure of a component in the rechargeable battery (or an electronic device that includes the rechargeable battery) to be determined. Consequently, the environmental monitoring device may provide efficient and safe charging of the rechargeable battery, which may increase customer satisfaction and, thus, may promote sales of the environmental monitoring device (and, more generally, commercial activity).

In a third group of embodiments, an environmental monitoring device that includes a switching mechanism is described. During operation of the environmental monitoring device, the switching mechanism (such as a switch) selectively electrically couples a first electrical-connection node and a second electrical-connection node. For example, using the switching mechanism, an electronic device that is electrically coupled to the first electrical-connection node may be selectively electrically coupled to a second electronic device that is electrically coupled to the second electrical-connection node. Moreover, an antenna and an interface circuit in the environmental monitoring device may receive sensor data from a third electronic device based on one or more measurements of an environmental condition in an external environment that includes the environmental monitoring device. Furthermore, the selective electrical coupling may be based on the one or more measurements of the environmental condition.

In this way, the environmental monitoring device facilitates switching based on distributed measurements of the environmental condition in the environment (such as by a sensor mechanism in the third electronic device, which is separate from the environmental monitoring device). For example, when a sound is present, a fire is detected, or an electrical characteristic of one of the electronic device and the second electronic device indicates a safety concern (such as a fire hazard, a short circuit, a risk of electric shock or electrocution, etc.), the first electrical-connection node may be electrically decoupled from the second electrical-connection node. Consequently, the environmental monitoring device may allow the switch state (i.e., the selective electrical coupling) to be dynamically adapted based on changing environmental conditions. This capability may allow the environmental monitoring device to work in conjunction with legacy electronic devices (i.e., without direct electrical coupling of instructions or without communication with the legacy electronic devices) and/or in conjunction with electronic devices that communicate directly with or that are electrically coupled to the environmental monitoring device. Thus, the environmental monitoring device may offer improved functionality and services, thereby promoting sales of the environmental monitoring device (and, more generally, commercial activity) and enhancing customer satisfaction with the environmental monitoring device.

In a fourth group of embodiments, an environmental monitoring device that includes a switching mechanism is described. During operation of the environmental monitoring device, the switching mechanism (such as a switch) selectively electrically couples a first electrical-connection node and a second electrical-connection node. For example, using the switching mechanism, an electronic device that is electrically coupled to the first electrical-connection node may be selectively electrically coupled to a second electronic device that is electrically coupled to the second electrical-connection node. Moreover, an antenna and an interface circuit in the environmental monitoring device may receive location information for an individual from a third electronic device. Furthermore, the selective electrical coupling may be based on one or more measurements of an environmental condition in an external environment that includes the environmental monitoring device and the location information. Note that a sensor mechanism in the environmental monitoring device may provide sensor data based on the one or more measurements. Alternatively, the antenna and the interface circuit in the environmental monitoring device may receive the sensor data from a fourth electronic device.

In this way, the environmental monitoring device facilitates switching based on the environmental condition in the environment and the location of the individual. For example, when the individual is in a region that includes the environmental monitoring device and the environmental condition matches one or more preferences of the individual, the first electrical-connection node may be electrically decoupled from the second electrical-connection node. Consequently, the environmental monitoring device may allow the switch state (i.e., the selective electrical coupling) to be dynamically adapted based on changing environmental conditions and the changing location of the individual. Thus, the environmental monitoring device may offer improved functionality and services, thereby promoting sales of the environmental monitoring device (and, more generally, commercial activity) and enhancing customer satisfaction with the environmental monitoring device.

In a fifth group of embodiments, an environmental monitoring device that includes a switching mechanism is described. During operation of the environmental monitoring device, the switching mechanism (such as a switch) selectively electrically couples a first electrical-connection node and a second electrical-connection node. For example, using the switching mechanism, an electronic device that is electrically coupled to the first electrical-connection node may be selectively electrically coupled to a second electronic device that is electrically coupled to the second electrical-connection node. The selective electrical coupling may be based on one or more measurements of an environmental condition in an external environment that includes the environmental monitoring device by a sensor mechanism in the environmental monitoring device. This environmental condition corresponds to power consumption by the electronic device and/or the second electronic device. Moreover, an antenna and an interface circuit in the environmental monitoring device communicate the environmental condition with a third electronic device.

In this way, the environmental monitoring device facilitates switching based on the energy consumption or the power consumption of the electronic device and/or the second electronic device. For example, the environmental condition may indicate usage of the electronic device and/or the second electronic device and/or a duration of usage of the electronic device and/or the second electronic device. Moreover, if an electrical characteristic of one of the electronic device and the second electronic device indicates a safety concern (such as a fire hazard, a short circuit, a risk of electric shock or electrocution, etc.), the first electrical-connection node may be electrically decoupled from the second electrical-connection node. Consequently, the environmental monitoring device may allow the switch state (i.e., the selective electrical coupling) to be dynamically adapted based on changing environmental conditions. Thus, the environmental monitoring device may offer improved functionality and services, thereby promoting sales of the environmental monitoring device (and, more generally, commercial activity) and enhancing customer satisfaction with the environmental monitoring device.

In a sixth group of embodiments, an environmental monitoring device that includes a switching mechanism is described. During operation of the environmental monitoring device, the switching mechanism (such as a switch) selectively electrically couples a first electrical-connection node and a second electrical-connection node. For example, using the switching mechanism, an electronic device that is electrically coupled to the first electrical-connection node may be selectively electrically coupled to a second electronic device that is electrically coupled to the second electrical-connection node. The selective electrical coupling may be based on one or more measurements of an environmental condition in an external environment that includes the environmental monitoring device by a sensor mechanism in the environmental monitoring device. Moreover, an override mechanism in the environmental monitoring device can specify an electrical coupling state of the first electrical-connection node and the second electrical-connection node that supersedes the selective electrical coupling based on the environmental condition.

In this way, the environmental monitoring device facilitates switching based on the environmental condition in the environment while allowing a user of the environmental monitoring device to override the selective electrical coupling. Consequently, the environmental monitoring device may allow the switch state (i.e., the selective electrical coupling) to be dynamically adapted based on changing environmental conditions while ensuring, as needed, that the user maintains control. These capabilities may allow the environmental monitoring device to offer improved functionality and services, thereby promoting sales of the environmental monitoring device (and, more generally, commercial activity) and enhancing customer satisfaction with the environmental monitoring device.

Note that the technique for monitoring an environmental condition is not an abstract idea. In particular, the measurements and the selective electrical coupling included in the technique for monitoring the environmental condition are not: a fundamental economic principle, a human activity (the operations in the technique for monitoring the environmental condition significantly exceed those of a human because they may involve measurements of the very large number of samples, parameters or factors in a noisy environment, as well as optional wireless communication), and/or a mathematical relationship/formula. Moreover, the technique for monitoring the environmental condition amounts to significantly more than an alleged abstract idea. In particular, the technique for monitoring the environmental condition may improve the functioning of an environmental monitoring device, an electronic device, a computer and/or the computer system that executes software and/or implements the technique for monitoring the environmental condition. For example, the technique for monitoring the environmental condition may: speed up computations performed during the technique for monitoring the environmental condition; reduce memory consumption when performing the computations (e.g., by using a distributed or disseminated architecture); improve reliability of the computations (as evidenced by improved monitoring and/or adjustment of the environmental condition); reduce network latency (e.g., by using the distributed or disseminated architecture); improve the user-friendliness of a user interface that displays results of the computations (e.g., by allowing a user to view information about the environmental condition and/or to modify a setting of the environmental monitoring device); and/or improve other performance metrics related to the function of the environmental monitoring device, the electronic device, the computer and/or the computer system.

Communication between electronic devices (such as the environmental monitoring device and an alarm device) may utilize wired, optical and/or wireless communication. For example, the wireless communication may involve communicating packets or frames that are transmitted and received by radios in the electronic devices in accordance with a communication protocol, such as: Bluetooth™ (from the Bluetooth Special Interest Group of Kirkland, Wash.), an Institute of Electrical and Electronics Engineers (IEEE) 802.15 standard (such as ZigBee® from the ZigBee® Alliance of San Ramon, Calif.), an Institute of Electrical and Electronics Engineers (IEEE) 802.11 standard, Z-Wave, a power-line communication standard, an infra-red communication standard, a universal serial bus (USB) communication standard, a near-field-communication standard or specification (from the NFC Forum of Wakefield, Mass.), another wireless ad-hoc network standard, and/or another type of wireless interface. In some embodiments, the communication protocol may be compatible with a $2^{nd}$ generation or mobile telecommunication technology, a $3^{rd}$ generation of mobile telecommunications technology (such as a communication protocol that complies with the International Mobile Telecommunications-2000 specifications by the International Telecommunication Union of Geneva, Switzerland), a $4^{th}$ generation of mobile telecommunications technology (such as a communication protocol that complies with the International Mobile Telecommunications Advanced specification by the International Telecommunication Union of Geneva, Switzerland), and/or another cellular-telephone communication technique. For example, the communication protocol may include Long Term Evolution or LTE. In the discussion that follows, ZigBee® is used as an illustrative example. In addition, the communication may occur via a wide variety of frequency bands, including frequencies associated with the so-called 'white space' in frequencies bands associated with analog television broadcasting.

The communication between the electronic devices is shown in FIG. 1, which presents a block diagram illustrating communication among environmental monitoring devices 110, optional electronic devices 114 (such as regulator devices e.g., optional electronic device 114-2, and/or legacy electronic devices, e.g., optional electronic device 114-1) and data-sharing electronic device 118 using wireless signals, and communication with optional computer 120 and optional network 122 (such as the Internet, a wireless local area network, an Ethernet network, an intra-net, an optical network, etc.) and aggregating or archive device 116 (which may or may not involve wireless signals). In particular, the communication between environmental monitoring devices 110, optional electronic devices 114, archive device 116, data-sharing electronic device 118 and/or optional computer 120 may involve the exchange of packets. These packets may be included in frames in one or more wireless channels.

Moreover, as described further below with reference to FIG. 2, environmental monitoring devices 110, archive device 116, data-sharing electronic device 118, optional computer 120 and/or optionally some of optional electronic devices 114 (such as optional electronic device 114-2) may include subsystems, such as: a networking subsystem, a memory subsystem, a processing subsystem, an optional user-interface subsystem, and a sensor subsystem. In addition, these electronic devices may include radios 126 in the networking subsystems. More generally, environmental monitoring devices 110, archive device 116, data-sharing electronic device 118, optional computer 120 and/or optionally some of optional electronic devices 114 can include (or can be included within) any electronic devices with networking subsystems that enable wirelessly communication with another electronic device. This can comprise transmitting frames on wireless channels to enable the electronic devices to make initial contact, followed by exchanging subsequent data/management frames (such as connect requests or petitions to establish a connection or link), configuring security options (e.g., encryption on a link or in a mesh network), transmitting and receiving packets or frames, etc.

As can be seen in FIG. 1, wireless signals 124 (represented by jagged lines) are transmitted from/received by radios 126 in environmental monitoring devices 110, data-sharing electronic device 118, optional computer and/or optionally some of optional electronic devices 114 (such as optional electronic device 114-2). In general, wireless communication among these electronic devices may or may not involve a connection being established among the electronic devices, and therefore may or may not involve communication via a wireless network. (Note that the communication between optional computer 120 and archive device 116 may occur via optional network 122, which may involve wired or optical communication with a different communication protocol than wireless signals 124.)

Furthermore, the processing of a packet or frame in an electronic device (such as environmental monitoring device 110-1) may include: receiving wireless signals 124 with the packet or frame; decoding/extracting the packet or frame from received wireless signals 124 to acquire the packet or frame; and processing the packet or frame to determine information contained in the packet or frame (such as at least a portion of a certified data packet).

As described further below with reference to FIGS. 11-26, environmental monitoring devices 110 may monitor environmental conditions in an environment 112 (which is sometimes referred to as an 'external environment'), such as a portion of a building, the building, a container or a package, a vehicle, a liquid, and/or a train car. (Note that one or more of environmental monitoring devices 110 may be immersed in a liquid, and environment 112 may be at a fixed location or time-varying locations.) For example, at least some of environmental monitoring devices 110 may include sensors (or sensor devices) that provide sensor data that reflects the environmental conditions in environment 112. In general, the sensor data may be provided without or excluding interaction (such as communication and/or electrical coupling) among environmental monitoring devices 110 and optional electronic devices 114. Thus, sensors in environmental monitoring devices 110 may indirectly infer information about the operation and/or the performance of optional electronic devices 114 based on the monitored environmental conditions. However, in some embodiments at least some of environmental monitoring devices 110 interact directly with at least some of optional electronic devices 114 (via communication or electrical coupling), thereby facilitating direct measurement of the sensor data, as well as feedback control of these electronic devices by at least some of environmental monitoring devices 110. In some embodiments, one or more of environmental monitoring devices 110 is integrated into one or more other electronic device, such as one or more of optional electronic devices 114.

The sensor data may be analyzed locally by at least one of environmental monitoring devices 110 and/or remotely by archive device 116. Moreover, the sensor data and/or the analyzed sensor data may be communicated among environmental monitoring devices 110. In particular, environmental monitoring devices 110 may form a ZigBee® mesh network, with ZigBee® end devices communicating with a ZigBee® coordinator (such as environmental monitoring device 110-1)

via one or more optional ZigBee® routers. Then, environmental monitoring device 110-1 may communicate (wirelessly and/or via optional computer 120 and optional network 122) the sensor data and/or the analyzed sensor data to archive device 116.

In addition, the sensor data and/or the analyzed sensor data may be communicated or shared with one or more other electronic devices, such as data-sharing electronic device 118 (e.g., a cellular telephone or a portable electronic device) and/or remote servers or computers not shown in FIG. 1. For example, the sensor data and/or the analyzed sensor data may be communicated to data-sharing electronic device 118 by at least some of environmental monitoring devices 110, such as the one or more optional ZigBee® routers and/or the ZigBee® coordinator. (Thus, at least some of environmental monitoring devices 110 may function as sensor-data hubs for other environmental monitoring devices 110.) Alternatively, the sensor data, the analyzed sensor data and/or operational information (such as remaining battery life) about at least some of environmental monitoring devices 110 may be communicated to data-sharing electronic device 118 by archive device 116 using wired, optical and/or wireless communication. Data-sharing electronic device 118 may display or provide this information to a user. In some embodiments, data-sharing electronic device 118 compares the information from multiple environmental monitoring devices 110 to ensure consistency before presenting the information to the user. This may reduce the likelihood of false alarms or misinformation. Alternatively, data-sharing electronic device 118 can present comparisons of the information from multiple environmental monitoring devices 110.

The sensor data, the analyzed sensor data and/or information that is communicated and/or stored by environmental monitoring devices 110 and/or archive device 116 may be protected. This may involve encryption using an encryption key (such as an encryption key associated with one of environmental monitoring devices 110 and/or a secure channel in a processor in one of environmental monitoring devices 110). The encryption key may use symmetric or asymmetric encryption techniques. Alternatively or additionally, a secure or one-way cryptographic hash function (such as SHA-256) may be used. For example, the secure hash may supplement encryption that is associated with a network interface in one or more of environmental monitoring devices 110. In some embodiments, the information communicated and/or stored in FIG. 1 is digitally signed by environmental monitoring devices 110.

Furthermore, archive device 116 may store the sensor data and/or the analyzed sensor data in secure, certified historical records or logs of the environmental conditions in environment 112. In principle, the information stored by archive device 116 may be protected. However, in some embodiments, users of environmental monitoring devices 110, who, in general, control how their data is used and shared, may instruct environmental monitoring devices 110 to provide, via the mesh network, information to archive device 116 that allows archive device 116 to unprotect the sensor data and/or the analyzed sensor data. Similarly, in response to requests from authorized recipients for the sensor data and/or the analyzed sensor data (such as a request from data-sharing electronic device 118), archive device 116 may provide access to the stored sensor data and/or the analyzed sensor data. If the sensor data and/or the analyzed sensor data are protected, the associated environmental monitoring devices 110 may provide protection information to data-sharing electronic device 118 that allows data-sharing electronic device 118 to unprotect the sensor data and/or the analyzed sensor data.

Environmental monitoring devices 110 may allow a variety of services to be offered to: users associated with environmental monitoring devices 110 (such as owners or renters of these environmental monitoring devices), suppliers of components or spare parts, maintenance personnel, security personnel, emergency service personnel, insurance companies, insurance brokers, realtors, leasing agents, apartment renters, hotel guests, hotels, restaurants, businesses, organizations, governments, potential buyers of physical objects, a shipping or transportation company, etc. For example, based on the analyzed sensor data feedback about the operation of one or more of optional electronic devices 114 (such as a legacy electronic device) may be provided by one or more of environmental monitoring devices 110 on displays, using speakers and, more generally, on physiological output devices that provide sensory information (such as lighting or an illumination pattern). Thus, a user may be alerted if a legacy electronic device is activated or if it is not functioning properly. More generally, the feedback may indicate the presence of an environmental condition in environment 112, such as: presence of an allergen, fire, flooding, a power outage, a chemical contaminant, an infestation, opening of a door, an individual entering or leaving a room, an individual getting out of bed, an individual waking up, an individual crying, an individual tossing and turning in bed, an individual shivering, a change in health condition of an individual (such as an illness, a chronic disease, etc.), etc.

Additionally, one or more of environmental monitoring devices 110 provide a maintenance notification based on the analyzed sensor data, which is associated with the operation of one of optional electronic devices 114 (such as a legacy electronic device or an electronic device that is included in a feedback loop with one of environmental monitoring devices 110) and/or which represents an environmental condition in environment 112. For example, the maintenance notification may include an instruction to replace a battery. In addition, the maintenance notification and any subsequent remedial action (such as a repair or service performed on one of optional electronic devices 114) may be stored in a historical record or log for environment 112 (such as a historical record maintained by archive device 116).

In some embodiments, a regulator device (such as one of optional electronic devices 114, e.g., a thermostat, a humidifier, an air purifier, a ventilator device, a fan, a motor, a window opener, a door opener, an access-control device for the environment, etc.) that regulates an environmental condition is modified based on a comparison of the sensor data and a target value of the environmental condition in environment 112. For example, one of environmental monitoring devices 110 may provide a control signal to the regulator device to modify an environmental condition (such as the temperature, humidity, airflow, etc.) based on a comparison of the sensor data and a target value performed by the environmental monitoring device, or another technique (which may be implemented using software) that uses an environmental condition as an input. (Note that the regulator device may include its own environmental sensor or thermostat, as well as a control mechanism and/or a switching mechanism to turn the regulator device on and off based on measurements provided by the environmental sensor. Thus, environmental monitoring devices 110 may perform measurements and/or selectively electrically couple the regulator device to a power source using an environmental sensor, control mechanism and/or a switching mechanism that are in addition to those included in the regulator device.)

Instead of providing the control signal to the regulator device, one of environmental monitoring devices 110 may perform the same function by selectively electrically coupling the regulator device to a power source using a switch (or a switching mechanism) in the environmental monitoring device (and, thus, external to the regulator device). More generally, environmental monitoring devices 110 may selectively electrically couple or decouple one or more of the electronic devices in FIG. 1 from each other and/or one or more power sources (such as a wall outlet) based on one or more of the monitored environmental conditions. As described further below with reference to FIGS. 11-26, this capability may allow the environmental monitoring devices 110 to respond to and/or modify the one or more environmental conditions. For example, when an acoustic sensor detects sound (such as that associated with a phone call or the opening or closing of a door), a noisy piece of equipment may be decoupled from a power source. Alternatively or additionally, when a fire-detection sensor detects the presence of fire or when a load-monitoring sensor detects an electrical characteristic such as a current, a voltage, a phase relative to at least a reference signal, a quality factor, a harmonic of a fundamental frequency, a resonance frequency, a time constant, noise, power consumption, etc.) that indicates there is a safety concern, the switch may change state to selectively decouple one or more of the electronic devices in FIG. 1 from other electronic devices and/or the one or more power sources. Similarly, the monitored electrical characteristic may be used to control the charging of a rechargeable battery and, in particular, to select a charging mode of the rechargeable battery. This may allow the life of the rechargeable battery to be increased, the charging time to be reduced and/or the power consumption during the recharging to be increased.

Furthermore, the environmental condition may include or correspond to (e.g., may be related to or a function of) power consumption by at least one of the electronic devices in FIG. 1. In these embodiments, environmental monitoring devices 110 may monitor and/or regulate the power consumption. Thus, the selective electrical coupling may be based on usage and/or a duration of usage of the at least one of the electronic devices in FIG. 1. In some embodiments, the selective electrical coupling is based on additional parameters, such as one or more preferences of an individual and/or a current or predicted location (and arrival time) of an individual, which may allow environmental monitoring devices 110 to provide services such as so-called 'geo-fencing' or a 'geo-fencing service' (e.g., where the selective electrical coupling occurs when the individual is within a particular region, at a particular location or not at the particular location).

In these ways, environmental monitoring devices 110 and/or archive device 116 may be used to: implement an information network with one or more legacy electronic devices; securely aggregate and selectively disseminate sensor data about environmental conditions; provide feedback about one or more environmental conditions in environment 112 (such as an alert provided by one of optional electronic devices 114); allow users to remotely control alerts provided by environmental monitoring devices 110 by modifying alert settings of environmental monitoring devices 110; selectively change a switching state of a switch in at least one of environmental monitoring devices 110 based at least on one or more environmental conditions in environment 112; and facilitate monitoring and maintaining of the one or more environmental conditions in environment 112.

Although we describe the environment shown in FIG. 1 as an example, in alternative embodiments, different numbers or types of electronic devices may be present. For example, some embodiments comprise more or fewer electronic devices.

We now describe embodiments of the environmental monitoring device, the archive device, and other electronic devices in FIG. 1. FIG. 2 presents a block diagram illustrating environmental monitoring device 200, such as one of environmental monitoring devices 110. This electronic device includes processing subsystem 210 (and, more generally, a control mechanism), memory subsystem 212, a networking subsystem 214, an optional user-interface subsystem 216, optional sensor subsystem 218 (i.e., a data-collection subsystem and, more generally, a sensor mechanism), feedback subsystem 232, power subsystem 246 and switching subsystem 250. Processing subsystem 210 includes one or more devices configured to perform computational operations and to executed techniques to process sensor data. For example, processing subsystem 210 can include one or more microprocessors, application-specific integrated circuits (ASICs), microcontrollers, programmable-logic devices, and/or one or more digital signal processors (DSPs).

In addition, processing subsystem 210 may include an optional secure channel 220, which is a system-on-chip within one or more processors in processing subsystem 210 that: performs secure processing of information, securely communicates with other components in environmental monitoring device 200, and more generally performs secure services. This secure channel may include one or more processors, a secure boot ROM, one or more security peripherals, and/or other components. The security peripherals may be hardware-configured to assist in the secure services performed by optional secure channel 220. For example, the security peripherals may include: authentication hardware implementing various authentication techniques, encryption hardware configured to perform encryption, secure-interface controllers configured to communicate over a secure interface to other components, and/or other components. In some embodiments, instructions executable by optional secure channel 220 are stored in a trust zone in memory subsystem 212 that is assigned to optional secure channel 220, and optional secure channel 220 fetches the instructions from the trust zone for execution. Optional secure channel 220 may be isolated from the rest of processing subsystem 210 except for a carefully controlled interface, thus forming a secure region for optional secure channel 220 and its components. Because the interface to optional secure channel 220 is carefully controlled, direct access to components within optional secure channel 220 (such as a processor or a secure boot ROM) may be prevented. In some embodiments, optional secure channel 220 encrypts and/or decrypts authentication information communicated with optional user-interface subsystem 216 and/or received via networking subsystem 214, and encrypts and/or decrypts information (such as sensor data) communicated with optional sensor subsystem 218.

Memory subsystem 212 includes one or more devices for storing data and/or instructions for processing subsystem 210, networking subsystem 214, optional user-interface subsystem 216 and/or optional sensor subsystem 218. For example, memory subsystem 212 can include dynamic random access memory (DRAM), static random access memory (SRAM), and/or other types of memory. In some embodiments, instructions for processing subsystem 210 in memory subsystem 212 include: one or more program modules 238 or sets of instructions (such as an environmental monitoring application, an environmentally gated switching program, a data-logging application, a data-sharing application and/or a maintenance application), which may be executed in an operating environment (such as operating system 236) by processing subsystem 210. Note that the one or more computer programs may constitute a computer-program mechanism or a program module. Moreover, instructions in the various modules in memory subsystem 212 may be implemented in: a high-level procedural language, an object-oriented programming language, and/or in an assembly or machine language. Furthermore, the programming language may be compiled or interpreted, e.g., configurable or configured (which may be used interchangeably in this discussion), to be executed by processing subsystem 210.

In addition, memory subsystem 212 can include mechanisms for controlling access to the memory. In some embodiments, memory subsystem 212 includes a memory hierarchy that comprises one or more caches coupled to a memory in environmental monitoring device 200. In some of these embodiments, one or more of the caches is located in processing subsystem 210.

In some embodiments, memory subsystem 212 is coupled to one or more high-capacity mass-storage devices (not shown). For example, memory subsystem 212 can be coupled to a magnetic or optical drive, a solid-state drive, or another type of mass-storage device. In these embodiments, memory subsystem 212 can be used by environmental monitoring device 200 as fast-access storage for often-used data, while the mass-storage device is used to store less frequently used data.

Networking subsystem 214 includes one or more devices configured to couple to and communicate on a wired, optical and/or wireless network (i.e., to perform network operations), including an interface circuit 222 (such as a ZigBee® communication circuit) and one or more antennas 224. For example, networking subsystem 214 can include: a ZigBee® networking subsystem, a Bluetooth™ networking system (which can include Bluetooth™ Low Energy, BLE or Bluetooth™ LE), a cellular networking system (e.g., a 3G/4G network such as UMTS, LTE, etc.), a USB networking system, a networking system based on the standards described in IEEE 802.11 (e.g., a Wi-Fi® networking system), an Ethernet networking system, an infra-red communication system, a power-line communication system and/or another communication system (such as a near-field-communication system or an ad-hoc-network networking system).

Moreover, networking subsystem 214 includes processors, controllers, radios/antennas, sockets/plugs, and/or other devices used for coupling to, communicating on, and handling data and events for each supported networking or communication system. Note that mechanisms used for coupling to, communicating on, and handling data and events on the network for each network system are sometimes collectively referred to as a 'network interface' for the network system. Moreover, in some embodiments a 'network' between the electronic devices does not yet exist. Therefore, environmental monitoring device 200 may use the mechanisms in networking subsystem 214 for performing simple wireless communication between environmental monitoring device 200 and other electronic devices, e.g., transmitting advertising frames, petitions, beacons and/or information associated with near-field communication.

Optional user-interface subsystem 216 may include one or more processors, controllers and devices for receiving information for a user of environmental monitoring device 200. For example, optional user-interface subsystem 216 may include a user-interface device 226 (and, more generally, a user-input mechanism), such as: a keypad, a touch-sensitive display, optical character recognition, image recognition, gesture recognition, biometric recognition (such as a fingerprint, a palm print, a retinal pattern, etc.), and/or voice recognition. The information may include: authentication information from the user (such as a passcode or a security code for unlocking access to environmental monitoring device 200, some of the functionality of environmental monitoring device 200 and/or to allow environmental monitoring device 200 to be moved from a current location); user-feedback about a request for access to sensor data associated with environmental monitoring device 200; and/or user preferences for operation of environmental monitoring device 200 (such as alarm settings, when and/or how to provide notifications, etc.). This information may be securely communicated to processing subsystem 210 (such as by encrypting the information). In addition, the information communicated may also include an encryption key that is specific to environmental monitoring device 200 and/or components in environmental monitoring device 200, such as optional secure channel 220.

Furthermore, optional sensor subsystem 218 may include one or more sensor devices 228 (or a sensor array), which may include one or more processors and memory. For example, the one or more sensor devices 228 may include: a thermal sensor (such as a thermometer), a humidity sensor, a barometer, a camera or video recorder (such as a CCD or CMOS imaging sensor), one or more microphones (which may be able to record acoustic information, including acoustic information in an audio hand of frequencies, in mono or stereo), a load-monitoring sensor (and, more generally, a sensor that monitors one or more electrical characteristics), an infrared sensor (which may be active or passive), a microscope, a particle detector (such as a detector of dander, pollen, dust, exhaust, etc.), an air-quality sensor, a particle sensor, an optical particle sensor, an ionization particle sensor, a smoke detector (such as an optical smoke detector or an ionizing smoke detector), a fire-detection sensor, a radon detector, a carbon-monoxide detector, a chemical sensor or detector, a volatile-organic-compound sensor, a combustible gas sensor, a chemical-analysis device, a mass spectrometer, a microanalysis device, a nano-plasmonic sensor, a genetic sensor (such as a micro-array), an accelerometer, a position or a location sensor (such as a location sensor based on the Global Positioning System or GPS), a gyroscope, a motion sensor (such as a light-beam sensor), a contact sensor, a strain sensor (such as a strain gauge), a proximity sensor, a microwave/radar sensor (which may be active or passive), an ultrasound sensor, a vibration sensor, a fluid flow sensor, a photodetector, a Geiger counter, a radio-frequency radiation detector, and/or another device that measures a physical effect or that characterizes an environmental factor or physical phenomenon (either directly or indirectly).

Moreover, the one or more sensor devices 228 may include redundancy (such as multiple instances of a type of sensor device) to address sensor failure or erroneous readings, to provide improved accuracy and/or to provide improved precision. Note that sensor data acquired by the one or more sensor devices 228 may be securely communicated to processing subsystem 210 (such as by encrypting the sensor data). In addition, the sensor data communicated may also include a digital signature that is specific to environmental monitoring device 200 and/or components in environmental monitoring device 200, such as optional secure channel 220.

Feedback subsystem 232 may include a display 234 for displaying information, such as: feedback about an environmental condition in an environment that includes environmental monitoring device 200, information about the operation of environmental monitoring device 200, and/or a maintenance notification associated with a regulator device in the environment or environmental monitoring device 200 (such as when one of one or more power sources 248 needs to be replaced). In particular, feedback subsystem 232 may include a display driver and display 234, such as: a liquid-crystal display, an e-ink display, an organic light emitting diode display, a braille output device, a laser projection display, a multi-touch touchscreen, a color-wheel display and, more generally, a device for visually displaying or providing information. Note that display subsystem 232 may be included in optional user-interface subsystem 216.

In addition, feedback subsystem 232 may include one or more light sources 242 (and, more generally, an illumination mechanism), such as: incandescent light sources, electroluminescent light sources (e.g., light emitting diodes), etc. These light sources may provide different illumination patterns or illumination sequences, which may be programmable. The different illumination patterns may have: different spatial patterns in the environment that includes environmental monitoring device 200, different wavelengths of light and/or different light intensities. The different illumination sequences can include: pulse width modulation, flashing sequences of lights of one or more colors or intensities, a flashing sequence of long, medium and/or short duration flashes or pulses (such as flashes having a duration of 10, 1 or 0.1 s, respectively), or any other suitable illumination sequence. Thus, a particular illumination pattern may illuminate at least a portion of the environment (such as by providing a green color when environmental monitoring device 200 is supplying power to another electronic device and/or by providing a blue color when environmental monitoring device 200 is communicating via a network).

Moreover, environmental monitoring device 200 may include power subsystem 246 with one or more power sources 248. Each of these power sources may include: a battery (such as a rechargeable or a non-rechargeable battery), a DC power supply, a transformer, and/or a switched-mode power supply. Moreover, the one or more power sources 248 may operate in a voltage-limited mode or a current-limited mode. Furthermore, these power sources may be mechanically and electrically coupled by a male or female adaptor to a wall or electrical-outlet socket or plug (such as a two or three-pronged electrical-outlet plug, which may be collapsible or retractable), a light socket (or light-bulb socket), electrical wiring (such as a multi-wire electrical terminal), a generator, a USB port or connector, a DC-power plug or socket, a cellular-telephone charger cable, a photodiode, a photovoltaic cell, etc. This mechanical and electrical coupling may be rigid or may be remateable. As described further below with reference to FIGS. 11-13, the one or more power sources 248 may be mechanically and electrically coupled to an external power source or another electronic device by one of the electrical-connection nodes in switch 252 in switching subsystem 250.

In some embodiments, power subsystem 246 includes or functions as a pass-through power supply for an electrical connector to an external electronic device (such as an appliance) that can be plugged into the electrical connector. Power to this electrical connector (and, thus, the external electronic device) may be controlled locally by processing subsystem 210, optional user-interface subsystem 216, feedback subsystem 232 (such as via optional switch 244), switching subsystem 250 (such as by switch 252), and/or remotely via networking subsystem 214. Moreover, the power to the electrical connector may be turned on or off in response to sensor data provided by optional sensor subsystem 218 (such as when a signal is greater than or less than a user-specified or an environmental-regulation-specified threshold value, e.g., a dust concentration of 20 mg/m$^3$). Note that power subsystem 246 and/or switching subsystem 250 may be compatible with one or more electrical standards. For example, the electrical standards may have different root-mean-square voltages (such as 120 V and 220 V).

During operation of environmental monitoring device 200, processing subsystem 210 may execute one or more program modules 238, such as an environmental monitoring application. In particular, environmental monitoring application may instruct one or more sensor devices 228 to measure or acquire sensor data that represents one or more environmental conditions in an environment that includes environmental monitoring device 200. For example, the environmental condition may include: presence of an individual (such as a resident or a potential burglar), opening of a door, an individual getting out of bed, an individual waking up, an individual crying, an individual tossing and turning in bed, an individual shivering, presence of a chemical compound (such as exhaust, carbon monoxide, radon, smoke, a non-volatile organic compound and/or a volatile organic compound), presence, of an allergen (such as dander or pollen), presence of dust, presence of a fungus, a fire, presence of smoke, flooding, a water leak, a chemical leak, presence of an insect or rodent (and, more generally, an infestation), discharge of a firearm, a possible altercation or criminal act (such as domestic violence), a medical emergency, a change in health condition of an individual, availability of electrical power (such as whether there is a power failure), a lighting condition (such as whether the lights are on or off), temperature deviating from a predefined target, and/or humidity deviating from a predefined target. In some embodiments, the environmental condition is associated with the operation of a regulator device (which may or may not be a legacy electronic device). The regulator device (and, more generally, one of optional electronic devices 114 in FIG. 1) may include: a smoke detector, a thermostat, a carbon-monoxide detector, an appliance, a pet or animal feeder, a plant or animal watering device, a clock, a security alarm, a humidifier, an air filter, a switch, a light, etc. Note that the monitoring of the sensor data may be continuous, periodic (such as after a time interval has elapsed) or as needed (such as event-driven monitoring).

Alternatively or additionally, instead of measuring the sensor data using optional sensor subsystem 218 or in conjunction with the measured sensor data from optional sensor subsystem 218, environmental monitoring device 200 may receive the sensor data from another electronic device (such as one of the other electronic devices in FIG. 1) that includes one or more sensor devices that are similar to sensor devices 228. In particular, the sensor data may be received from the other electronic device using networking subsystem 214.

The measured and/or the received sensor data may be communicated to processing subsystem 210. Then, the environmental monitoring application may optionally analyze the sensor data, e.g., calculating a discrete or a Fourier transform, determining a histogram, performing filtering or signal processing, performing data compression, calibrating one or more of sensor devices 228, managing power consumption of environmental monitoring device 200, identifying one or more of sensor devices 228 that are not working or which are outputting erroneous sensor data, applying another transformation, calculating statistics (such as moments of a distribution), performing supervised learning (such as Bayesian analysis), performing noise reduction, normalizing the sensor data, converting units, etc. (Alternatively or additionally, the sensor data or a document summarizing the sensor data may be communicated to another electronic device using networking subsystem 214 and the analysis may be performed remotely, e.g. by archive device 116 in FIGS. 1 and 4.) For example, the analysis may determine whether an environmental condition is present in the environment. In some embodiments, this analysis is based on information, such as sensor data and/or environmental conditions, received from other environmental monitoring devices. This may allow calibration settings, such as environment-specific threshold values, to be determined for the environment and/or environmental monitoring device 200. (Alternatively or additionally, the calibration settings may be manually set by a user or by software that implements a calibration technique.) In addition, the analysis may be based on information from external data sources, such as datasets of weather and environmental phenomena, e.g., tornados, hurricanes, earthquakes, tsunamis, weather forecasts, etc.

Then, the environmental monitoring application may provide feedback to a user of environmental monitoring device 200, data-sharing electronic device 118 (FIG. 1) and/or directly to one of optional electronic devices 114 in FIG. 1 (if this electronic device is able to communicate with environmental monitoring device 200 via networking subsystem 214). In particular, the environmental monitoring application may instruct feedback subsystem 232 to provide sensory information, such as; a text or graphical message, a graph, a report, a chart, a spectrum, a video displayed on display 234, a sound or audio message (such as an alert) output by optional speakers 240 and/or an illumination pattern output by optional light sources 242. For example, the sensory information may include: a range of values, numerical measurements, shades of gray (or grayscale), colors, chemical formulas, images, illumination patterns, textures, patterns (which may correspond to one or more environmental conditions), tessellations with gradients of larger or smaller element sizes, and/or tessellations of increasing or decreasing element sizes (such as tessellation that are adjusted to be larger or smaller as a given environmental condition increases or decreases). Thus, in some embodiments the sensory information includes a change in the color of environmental monitoring device 200. Alternatively or additionally, the feedback may include a change in the illumination pattern provided by optional light sources 242. In some embodiments, the feedback is communicated using networking subsystem 214 and presented to the user (or other individuals) on another electronic device, such as data-sharing electronic device 118 (FIG. 1) or a different electronic device (such as the user's cellular telephone, tablet computer or computer) that is used for remote visualization of: the sensor data, the analyzed sensor data, the environmental condition and/or the feedback.

For example, in response to an environmental condition or a threat, environmental monitoring device 200 may output an alert, which may include audible sound (or feedback) in the environment and/or information that is wirelessly communicated to one or more electronic devices (such as data-sharing electronic device 118 in FIG. 1). There may be different types of alerts (such as different warning sounds, lights, messages, etc.) for different environmental conditions. Additionally, environmental monitoring device 200 may output or provide more than one alert at the same time.

In some embodiments, the environmental monitoring application may provide, via networking subsystem 214, the feedback to one or more of environmental monitoring devices 110 (FIG. 1) and/or other electronic devices (such as computers or servers associated with or operated on behalf of component suppliers, retailers, insurance companies, security personnel, emergency service personnel, maintenance organizations, shipping companies, landlords or property owners, a corporate-compliance organization, inspectors, businesses, government agencies, etc.). For example, the environmental monitoring application may utilize a Short Message Service, email, a social network and/or a messaging service with a restricted number of characters per message. Alternatively or additionally, the feedback may be posted to a web page or website (and, more generally, a location on a network), and one or more recipients may be notified via networking subsystem 214, e.g., a link to the location may be provided to the recipients.

In turn, an electronic device (such as data-sharing electronic device 118 in FIG. 1) may, via networking subsystem 214, modify settings of environmental monitoring device 200 (such as alarm settings, user preferences, etc.) that change how the feedback is provided locally (e.g., using optional speakers 240) and/or remotely (e.g., using networking subsystem 214), and which more generally change one or more functions of environmental monitoring device 200. For example, a user of data-sharing electronic device 118 in FIG. 1 may access a web page associated with a provider of environmental monitoring device 200 to modify one or more settings, such as to disable the providing of alerts or feedback.

When the providing of the alert is disabled, processing subsystem 210 may continue to assess a potentially threatening environmental condition (such as the possible presence of smoke or carbon monoxide) based on subsequent sensor data and, if the threat is increasing (such as if the concentration of carbon monoxide is increasing or has become dangerous), may reactivate the providing of the alert. Alternatively, after a time interval (such as 5, 10, 15 or 30 minutes), the modified alert setting may automatically revert to the original alert setting, so that environmental monitoring device 200 can provide alerts again. In some embodiments, a user subsequently changes the modified alert setting back to the original alert setting or resets the alert setting to default. Thus, environmental monitoring device 200 may continue to assess the impact of one or more environmental factors (and, more generally, the environmental condition) on the safety of the external environment, while also providing a user operational control over alerts. In addition, environmental monitoring device 200 may provide fail safes both in how alerts are disabled and by reactivating alerts in case the threat is increasing.

Note that the sensor data and/or the analyzed sensor data may be stored, at least temporarily, in a data structure in memory subsystem 212. This is shown in FIG. 3, which presents a data structure 300. In particular, data structure 300 may include entries 308 with: sensor data 310, timestamps 312, locations 314, optional analyzed sensor data 316, and/or environmental conditions 318. Note that locations 314 (or location information) may specify locations were the sensor data was acquired or measured. For example, the location information may be measured using a sensor device in environmental monitoring device 200 in FIG. 2 (such as a location monitor) and/or the location information may be received from another electronic device that is proximate to environmental monitoring device 200 in FIG. 2 (such as an individual's cellular telephone that is within 1-10 in). Thus, the location may be determined via GPS and/or a cellular-telephone network (e.g., triangulation or trilateration).

Referring back to FIG. 2, in some embodiments processing subsystem 210 performs a remedial action in response to an alert or an alarm (i.e., based on one or more environmental conditions). This remedial action may include communicating with a regulator device to correct the environmental condition(s). For example, via networking subsystem 214, processing subsystem 210 may instruct the regulator device to:

ventilate the area, activate a humidifier, power on or power off a regulator device, initiate the operation of a mode on a regulator device, etc. As noted previously, and described further below, this same function (and, more generally, the remedial action) may be performed without communicating with the regulator device by changing a state of switch 250 in switching mechanism 250. Alternatively, as described further below, processing subsystem 210 may provide a maintenance notification (such as a notification to change an air filter). Furthermore, the alert may indicate a remedial action, such as positive or negative changes that can restore the environmental condition to a safe value. Thus, the alert may indicate that a user should turn on the ventilation or wear a safety mask when painting or vacuuming, and/or may encourage the user to stop applying a chemical product (such as paint) or to slow down the rate of application.

In some embodiments, the one or more program modules 238 include an environmentally gated switching program. If the sensor data from the one or more sensor devices 228 indicate the presence of one or more environmental conditions, processing subsystem 210 executing the environmentally gated switching program may provide an instruction or a control signal to switching mechanism 250 to change a state of switch 252, thereby selectively electrically coupling or decoupling electrical-connection nodes in switch 252. This may selectively electrically couple electronic devices to each other or to one or more power sources (such as one of power sources 248 and/or an external power source, e.g., a wall outlet). In this way, environmental monitoring device 200 may perform remedial action in response to the presence of one or more environmental conditions by selectively electrically coupling the regulator device to a power source. Thus, this capability may allow environmental monitoring device 200 to respond to and/or modify the one or more environmental conditions.

In some embodiments, the selective electrical coupling is based on additional parameters, such as one or more preferences of an individual, which may be stored in memory subsystem 212 and/or which may be received from the individual using networking subsystem 214. Alternatively or additionally, the selective electrical coupling may be based on a current or predicted location (and arrival time) of an individual. This may allow environmental monitoring device 200 to provide geo-fencing services in which the selective electrical coupling occurs when the individual is within or outside of a particular region. Thus, switch 252 in switching mechanism 250 may selectively electrically couple an electronic device from a power source when the individual is about to arrive at their home or when they wake up and go into the kitchen.

In order to allow a user local control over operation of switching mechanism 250 in spite of the one or more environmental conditions, environmental monitoring device 200 may include an override mechanism, such as optional switch 244 (or a button) in feedback subsystem 232. If the user activates or changes a position of the button or the switch on environmental monitoring device 200, this may specify the state of switch 252 (and, thus, may supersede the instruction of the control signal provided by the processing subsystem 210 based on the one or more environmental conditions).

In some embodiments, the one or more program modules 238 include a data-logging application. In conjunction with archive device 116 (FIGS. 1 and 4), the data-logging application may maintain a secure, certified historical record or log for the environment and/or a physical object in the environment (such as a 'homefax' record for an apartment or a building). Note that the physical object may include: a portion of a building (e.g., an apartment, a hotel room, an office suite, a storage unit, etc.), the building, a container (such as a box, a package or a shipping container), a vehicle (such as a car or truck), a liquid, and/or a train car. Notably, optional sensor subsystem 218 may securely communicate the sensor data to processing subsystem 210. Using optional secure channel 220, a digital signature for the sensor data may be generated, e.g., using a secure hash function and/or an encryption key that are associated with environmental monitoring device 200 and/or optional secure channel 220. For example, the digital signature may be generated using a secure hash of a time stamp, a random number (or a pseudorandom number, both of which are henceforth referred to as a 'random number'), and/or an identifier of environmental monitoring device 200. Then, the data-logging application may instruct networking subsystem 214 to communicate a certified data package (with the sensor data or analyzed sensor data, the digital signature, location information and/or an associated time stamp) to archive device 116 (FIG. 1) for inclusion in the historical record or log for the environment.

Moreover, the one or more program modules 238 may include a data-sharing application. This data-sharing application may enable a designated or authorized recipient to access protected sensor data that is stored in archive device 116 (FIG. 1). In particular, when executed by processing subsystem 210, the data-sharing application may instruct optional sensor subsystem 218 to measure or collect sensor data that represents the environmental condition. Then, the data-sharing application may protect the sensor data and/or analyzed sensor data. For example, the sensor data and/or the analyzed sensor data may be encrypted using an encryption key by processing subsystem 210 and/or optional secure channel 220. Alternatively or additionally, the sensor data and/or the analyzed sensor data may be protected using a secure hash function in conjunction with an identifier of environmental monitoring device 200 and/or a random (or pseudorandom) number generated by processing subsystem 210. Next, data-sharing application may instruct networking subsystem 214 to provide the protected sensor data and/or the analyzed sensor data to archive device 116 (FIG. 1).

Subsequently, when environmental monitoring device 200 receives, via networking subsystem 214, a request for the sensor data from data-sharing electronic device 118 (FIG. 1), the data-sharing application may access a predefined authorization preference of a user of environmental monitoring device 200 that is stored in memory subsystem 212. If the predefined authorization preference of the user authorizes the recipient associated with the request, the data-sharing application may provide, via networking subsystem 214, authorization information to archive device 116 (FIG. 1) to release the sensor data to data-sharing electronic device 118 (FIG. 1). Alternatively, the data-sharing application may instruct feedback subsystem 232 to request feedback about the request from the user. This user feedback may be received via optional user-interface subsystem 216. If the user feedback approves the request, the data-sharing application may provide, via networking subsystem 214, authorization information to archive device 116 (FIG. 1) to release the sensor data to data-sharing electronic device 118 (FIG. 1). (Thus, the user of environmental monitoring device 200 may control when other parties are allowed to access the sensor data.) Note that the data-sharing application may also provide, via networking subsystem 214, protection information specifying how to unprotect the sensor data to archive device 116 (FIG. 1) and/or to data-sharing electronic device 118 (FIG. 1). For example, the data-sharing application may provide the encryption key and/or may indicate the secure hash function, the random (or pseudorandom) number and/or the identifier.

In some embodiments, this protection information is received from the user of environmental monitoring device 200, e.g., via networking interface 214 and/or optional user-interface subsystem 216.

In some embodiments, the one or more program modules 238 include a maintenance application. This maintenance application may provide a maintenance notification related to the operation of environmental monitoring device 200, one of the other electronic devices in FIG. 1 and/or one or more environmental conditions in the environment. For example, the maintenance application may provide an instruction to: perform maintenance, replace a battery (and, more generally, one of power sources 248), replace one of the one or more sensor devices 228, order another replacement component (such as a filter) and/or to take out the garbage. When providing the maintenance notification, the maintenance application may instruct feedback subsystem 232 to present the maintenance notification to the user or maintenance personnel, and/or may instruct networking subsystem 214 to communicate the maintenance notification to another electronic device, such as the user's cellular telephone. In some embodiments, maintenance application suggests or recommends a specific provider or product to address or perform a remedial action in response to a maintenance notification. Alternatively, maintenance application may direct a user to a document (such as a web page or website) that includes information related to a maintenance notification.

Within environmental monitoring device 200, processing subsystem 210, memory subsystem 212, networking subsystem 214, optional user-interface subsystem 216, optional sensor subsystem 218, feedback subsystem 232, power subsystem 246 and/or switching subsystem 250 may be coupled using one or more interconnects, such as bus 230. These interconnects may include an electrical, optical, and/or electro-optical connection that the subsystems can use to communicate commands and data among one another. Note that different embodiments can include a different number or configuration of electrical, optical, and/or electro-optical connections among the subsystems. In some embodiments, environmental monitoring device 200 can detect tampering with secure components (such as optional secure channel 220 and/or bus 230) and may destroy encryption/decryption keys or information (such as a stored sensor data or authentication information) if tampering is detected.

Environmental monitoring device 200 can be (or can be included in) any electronic device with at least one network interface. For example, environmental monitoring device 200 can be (or can be included in): a sensor (such as a smart sensor), a tablet computer, a smartphone, a cellular telephone, an appliance, a regulator device, a consumer-electronic device (such as a baby monitor), a portable computing device, test equipment, a digital signal processor, a controller, a personal digital assistant, a laser printer (or other office equipment such as a photocopier), a personal organizer, a toy, a set-top box, a computing device (such as a laptop computer, a desktop computer, a server, and/or a subnotebook/netbook), a light (such as a nightlight), an alarm, a smoke detector, a carbon-monoxide detector, a monitoring device, and/or another electronic device (such as a switch or a router).

Although specific components are used to describe environmental monitoring device 200, in alternative embodiments, different components and/or subsystems may be present in environmental monitoring device 200. For example, environmental monitoring device 200 may include one or more additional processing subsystems, memory subsystems, networking subsystems, user-interface subsystems, sensor subsystems, feedback subsystems, power subsystems and/or switching subsystems. Additionally, one or more of the subsystems may not be present in environmental monitoring device 200. Moreover, in some embodiments, environmental monitoring device 200 may include one or more additional subsystems that are not shown in FIG. 2. For example, environmental monitoring device 200 can include: another or a different type of physiological output subsystem that provides sensory information to the user, one or more motors that rotate one or more color wheels (or color-wheel indicators) with low power consumption (such as a brushed motor, a brushless motor, a piezo-type ratcheting motor, etc.), and/or an alarm subsystem. Note that a given motor may rotate a color wheel using an open-loop control technique or a closed-loop control technique based on an encoder, such as: an optical encoder, a mechanical encoder, a potentiometer, etc. Furthermore, note that the one or more optional speakers 240 and a microphone in environmental monitoring device 200 may be used to provide audio conferencing capability to another electronic device.

Figure 2:
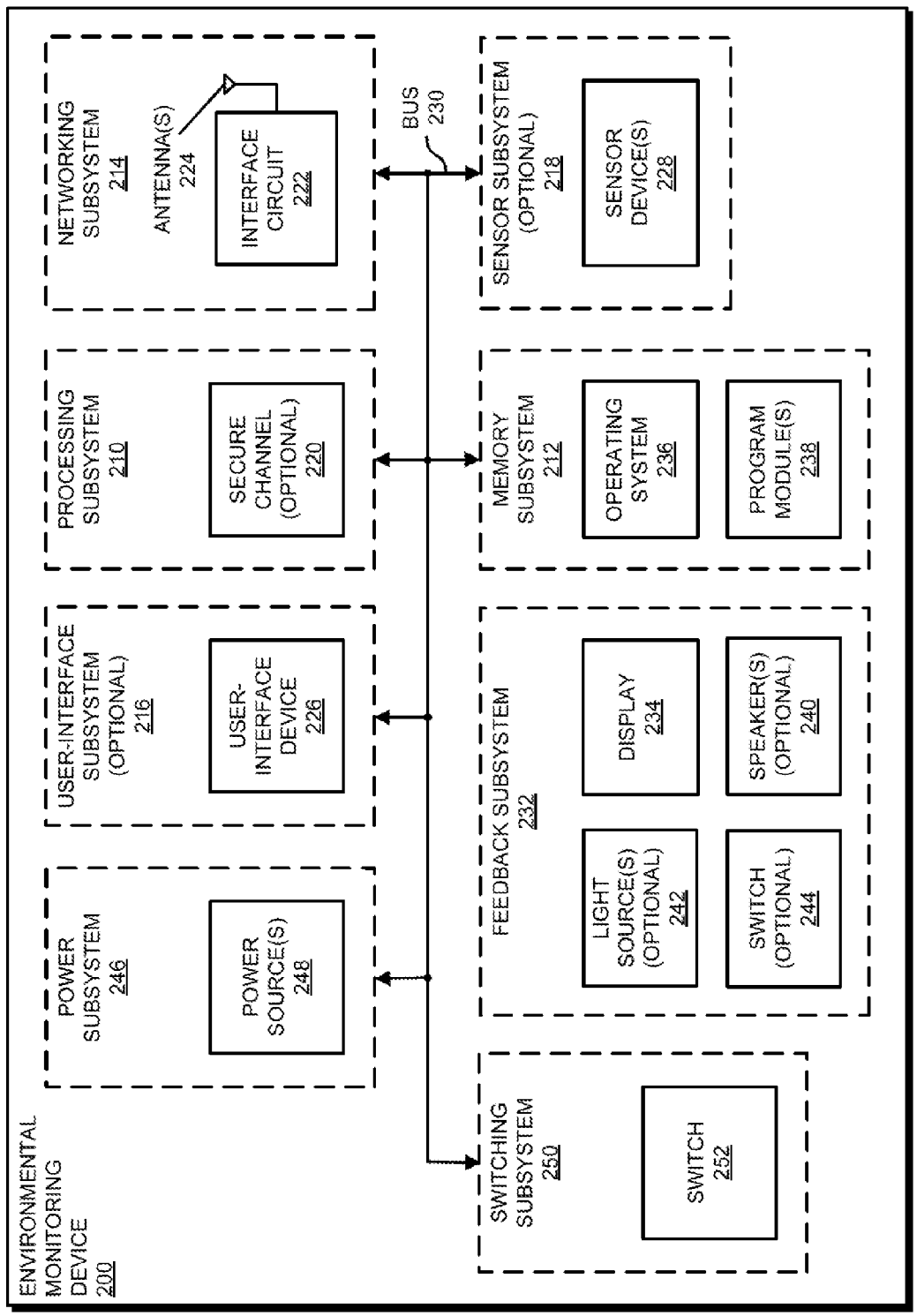
FIG. 2 is a block diagram illustrating an environmental monitoring device of FIG. 1 in accordance with an embodiment of the present disclosure.
Figure 3:
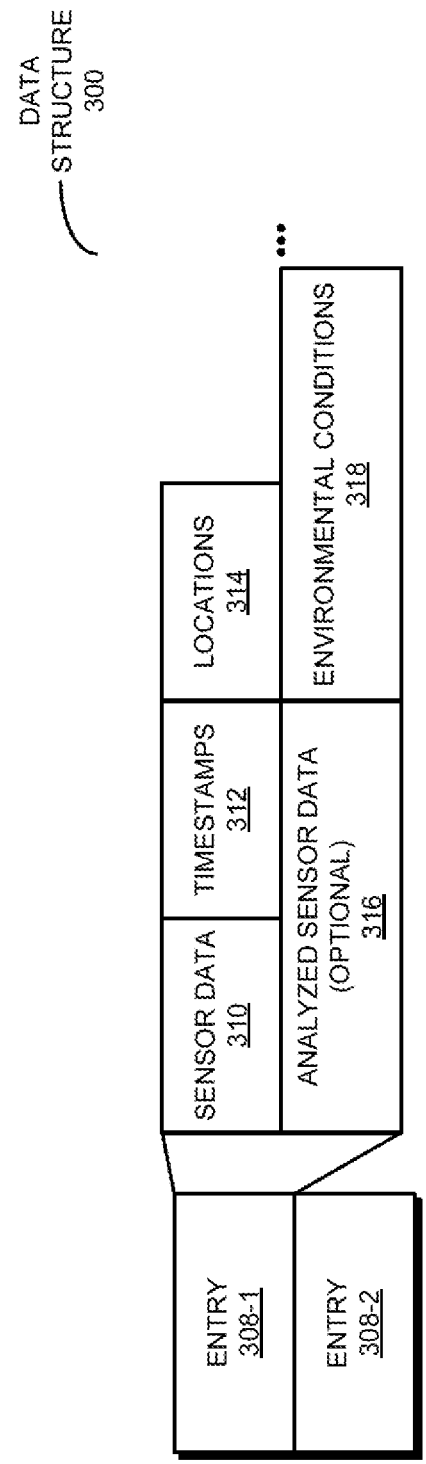
FIG. 3 is a block diagram illustrating a data structure with sensor data in the environmental monitoring device of FIG. 2 in accordance with an embodiment of the present disclosure.

Although separate subsystems are shown in FIG. 2, in some embodiments, some or all of a given subsystem or component can be integrated into one or more of the other subsystems or components in environmental monitoring device 200. For example, in some embodiments the one or more program modules 238 are included in operating system 236. In some embodiments, a component in a given subsystem is included in a different subsystem, e.g., optional switch 244 may be included in optional user-interface subsystem 216.

Moreover, the circuits and components in environmental monitoring device 200 may be implemented using any combination of analog and/or digital circuitry, including: bipolar, PMOS and/or NMOS gates or transistors. Furthermore, signals in these embodiments may include digital signals that have approximately discrete values and/or analog signals that have continuous values. Additionally, components and circuits may be single-ended or differential, and power supplies may be unipolar or bipolar.

An integrated circuit may implement some or all of the functionality of networking subsystem 214 (such as a radio) and, more generally, some or all of the functionality of environmental monitoring device 200. Moreover, the integrated circuit may include hardware and/or software mechanisms that are used for transmitting wireless signals from environmental monitoring device 200 to, and receiving signals at environmental monitoring device 200 from other electronic devices. Aside from the mechanisms herein described, radios are generally known in the art and hence are not described in detail. In general, networking subsystem 214 and/or the integrated circuit can include any number of radios. Note that the radios in multiple-radio embodiments function in a similar way to the radios described in single-radio embodiments.

In some embodiments, networking subsystem 214 and/or the integrated circuit include a configuration mechanism (such as one or more hardware and/or software mechanisms) that configures the radio(s) to transmit and/or receive on a given communication channel (e.g., a given carrier frequency). For example, in some embodiments, the configuration mechanism can be used to switch the radio from monitoring and/or transmitting on a given communication channel to monitoring and/or transmitting on a different communication channel. (Note that 'monitoring' as used herein comprises receiving signals from other electronic devices and possibly performing one or more processing operations on the received signals, e.g., determining if the received signal comprises an advertising frame, a petition, a beacon, etc.)

While a communication protocol compatible with ZigBee® was used as an illustrative example, the described embodiments of environmental monitoring device 200 may use a variety of network or communication interfaces. Furthermore while some of the operations in the preceding embodiments were implemented in hardware or software, in general the operations in the preceding embodiments can be implemented in a wide variety of configurations and architectures. Therefore, some or all of the operations in the preceding embodiments may be performed in hardware, in software or both. For example, at least some of the operations performed by processing subsystem 210 may be performed by optional sensor subsystem 218.

Figure 4:
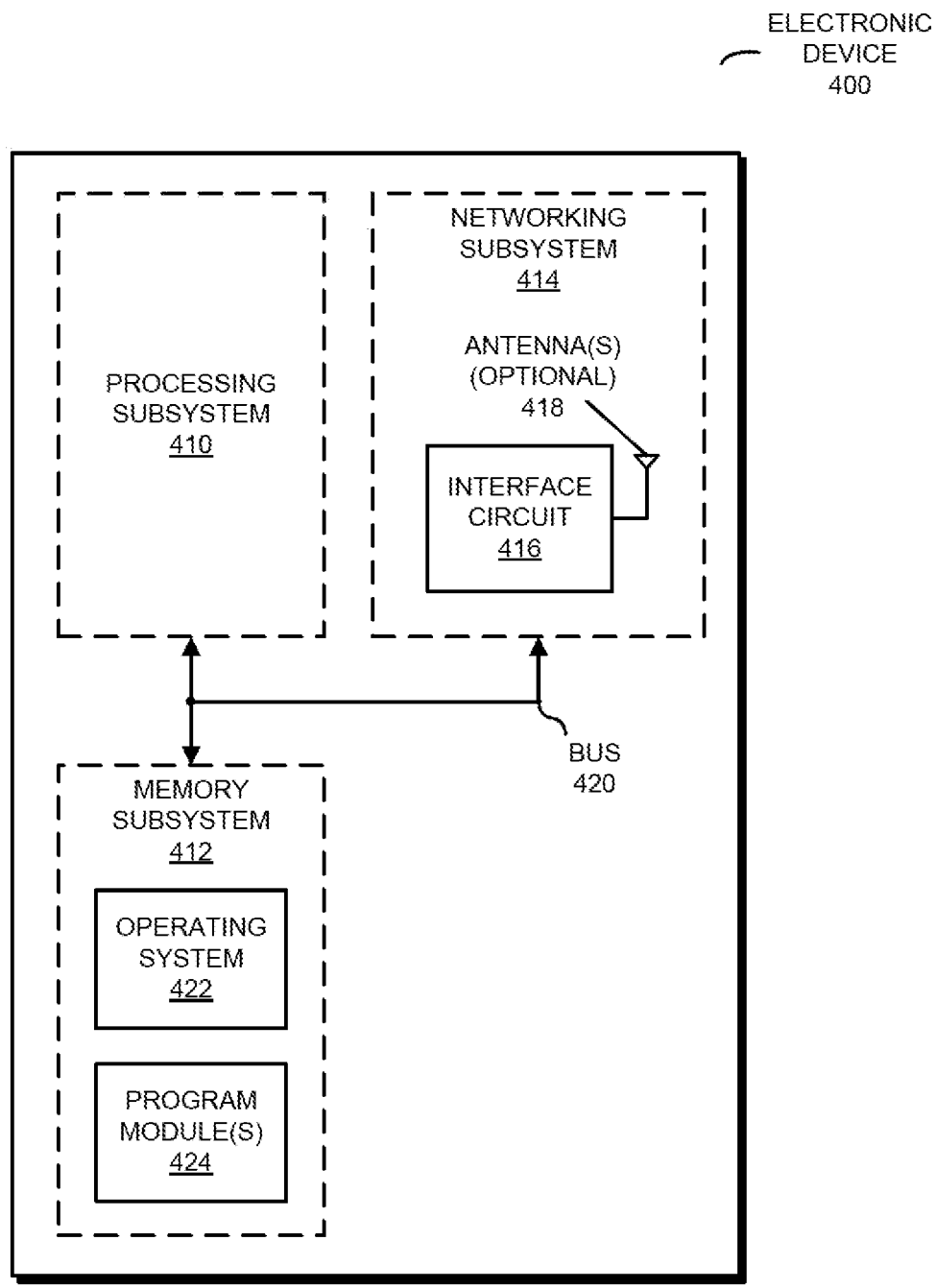
FIG. 4 is a block diagram illustrating an archive device of FIG. 1 in accordance with an embodiment of the present disclosure.

Furthermore, while the preceding discussion focused on the hardware, software and functionality in environmental monitoring device 200, archive device 116 (FIG. 1) and/or optional computer 120 (FIG. 1) may have the same or similar hardware (processors, memory, networking interfaces, etc.) and/or software to support the operations performed by these electronic devices or systems. This is shown in FIG. 4, which presents a block diagram illustrating electronic device 400, such as archive device 116 (FIG. 1). In particular, electronic device 400 includes processing subsystem 410, memory subsystem 412 and/or a networking subsystem 414. Processing subsystem 410 includes one or more devices configured to perform computational operations. For example, processing subsystem 410 can include one or more microprocessors, application-specific integrated circuits (ASICs), microcontrollers, programmable-logic devices, and/or one or more digital signal processors (DSPs).

Memory subsystem 412 includes one or more devices for storing data and/or instructions for processing subsystem 410 and/or networking subsystem 414. For example, memory subsystem 412 can include dynamic random access memory (DRAM), static random access memory (SRAM), and or other types of memory. In some embodiments, instructions for processing subsystem 410 in memory subsystem 412 include: one or more program modules 424 or sets of instructions (such as an archiving application, an analysis application, a data-sharing application and/or a notification application), which may be executed in an operating environment (such as operating system 422) by processing subsystem 410. Note that the one or more computer programs may constitute a computer-program mechanism or a program module. Moreover, instructions in the various modules in memory subsystem 412 may be implemented in: a high-level procedural language, an object-oriented programming language, and/or in an assembly or machine language. Furthermore, the programming language may be compiled or interpreted, e.g., configurable or configured (which may be used interchangeably in this discussion), to be executed by processing subsystem 410.

In addition, memory subsystem 412 can include mechanisms for controlling access to the memory. In some embodiments, memory subsystem 412 includes a memory hierarchy that comprises one or more caches coupled to a memory in electronic device 400. In some of these embodiments, one or more of the caches is located in processing subsystem 410.

In some embodiments, memory subsystem 412 is coupled to one or more high-capacity mass-storage devices (not shown). For example, memory subsystem 412 can be coupled to a magnetic or optical drive, a solid-state drive, or another type of mass-storage device. In these embodiments, memory subsystem 412 can be used by electronic device 400 as fast-access storage for often-used data, while the mass-storage device is used to store less frequently used data. Note that memory subsystem 412 may include multiple storage devices at one or more locations. Thus, data storage by memory subsystem 412 may be distributed, such as a cloud-based data-storage system.

Networking subsystem 414 includes one or more devices configured to couple to and communicate on a wired, optical and/or wireless network (i.e., to perform network operations), including an interface circuit 416 and one or more optional antennas 418. For example, networking subsystem 414 can include: a ZigBee® networking subsystem, a Bluetooth™ networking system (which can include Bluetooth™ Low Energy, BLE or Bluetooth™ LE), a cellular networking system (e.g., a 3G/4G network such as UMTS, LTE, etc.), a USB networking system, a networking system based on the standards described in IEEE 802.11 (e.g., a Wi-Fi® networking system), an Ethernet networking system and/or another communication system.

Moreover, networking subsystem 414 includes processors, controllers, radios/antennas, sockets/plugs, and/or other devices used for coupling to, communicating on, and handling data and events for each supported networking or communication system. Note that mechanisms used for coupling to, communicating on, and handling data and events on the network for each network system are sometimes collectively referred to as a 'network interface' for the network system.

During operation of electronic device 400, processing subsystem 410 may execute one or more program modules 424, such as an archiving application. This archiving application may receive, via networking interface 414, data packets from one or more of environmental monitoring devices 110 (FIG. 1). These data packets may include sensor data and/or analyzed sensor data. In some embodiments, processing subsystem 410 executes an analysis application, which analyzes the received sensor data. For example, the received sensor data may be: time stamped for time-series processing, filtered, compressed, etc. In some additional embodiments, processing subsystem 410 executes an analysis application, which can compare received sensor data analysis from one or more of environmental monitoring devices 110 (FIG. 1). As noted previously, the analysis may be based on information from external sources, such as datasets of weather and environmental phenomena. Consequently, in these embodiments networking interface 414 may be instructed by processing subsystem 410 to access the information in the external sources.

Figure 5:
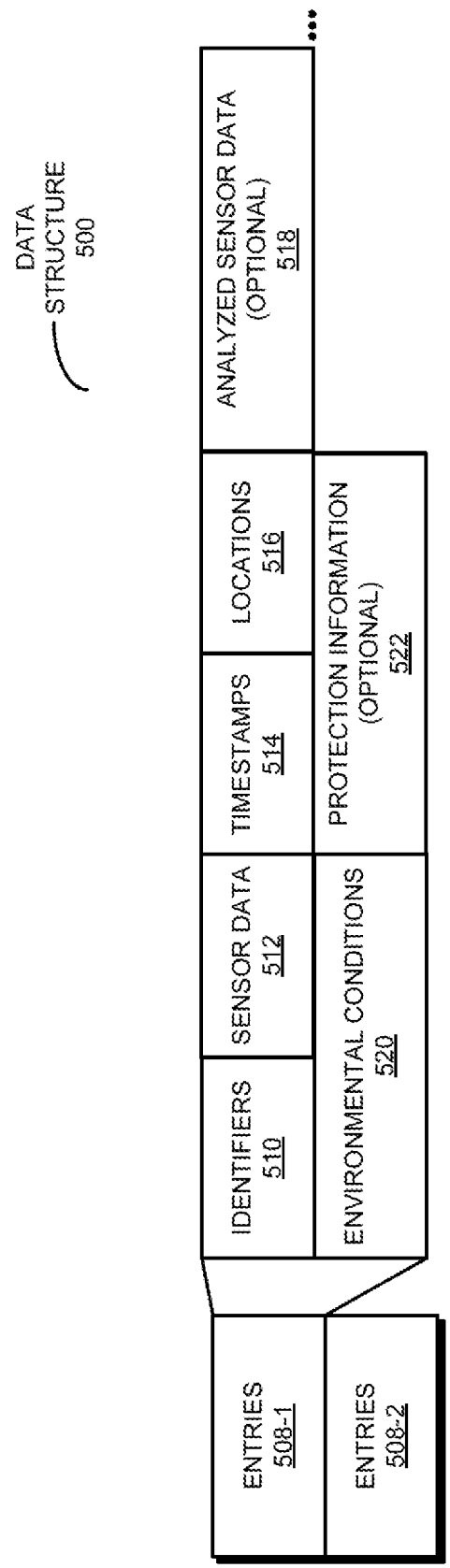
FIG. 5 is a block diagram illustrating a data structure with a historical record in the archive device of FIG. 4 in accordance with an embodiment of the present disclosure.

Then, archiving application may store the sensor data and/or the analyzed sensor data in a data structure in memory subsystem 412. This is shown in FIG. 5, which presents a block diagram illustrating data structure 500. In particular, data structure 500 may include entries 508 with: identifiers 510 of environmental monitoring devices, sensor data 512, timestamps 514, locations 516, optional analyzed sensor data 518, environmental conditions 520 and/or optional protection information 522.

Referring back to FIG. 4, in some embodiments the received data packets include protected information. For example, the sensor data and/or the analyzed sensor data may be encrypted using an encryption key associated with one of environmental monitoring devices 110 (FIG. 1) and/or a secure channel in the one of environmental monitoring devices 110 (FIG. 1). Alternatively or additionally, there may be a digital signature associated with the sensor data and/or the analyzed sensor data, and/or the sensor data and/or the analyzed sensor data may be protected using a secure hash function. In these embodiments, optional protection information 522 (FIG. 5) may include information that can confirm the source(s) of the received data packets (such as one or more of environmental monitoring devices 110 in FIG. 1) and/or can be used to unprotect the sensor data and/or the analyzed sensor data. Note that optional protection information 522 (FIG. 5) may be received, via networking interface 414, from one of environmental monitoring devices 110 (FIG. 1). This protection information may include the encryption key or an encryption key associated with the encryption key (which can be used to confirm the digital signature and/or decrypt encrypted information). Networking device 414 can utilize: encrypted tunneling in at least one networking interface, a network switch and/or network router between one of environmental monitoring devices 110 and archive device 116 in FIG. 1. Similarly, optional protection information 522 (FIG. 5) may specify the secure hash function, may include the identifier for one of environmental monitoring devices 110 (FIG. 1) and/or may include the random (or pseudorandom) number (which also can be used to unprotect information). Note that protection information 522 may include fault tolerance information (such as parity bits or hashes) to aid in the detection of tampered data, corrupted data, and/or erroneous sensor readings in the event of a sensor failure or miscalibration.

In an exemplary embodiment, a public-private encryption-key technique is used. In particular, a certified, secure data package may be signed by one of environmental monitoring devices 110 (FIG. 1) using a public encryption key of archive device 116 (FIG. 1), and the digital signature may be verified and the certified, secure data package may be decrypted using the private encryption key of archive device 116 (FIG. 1). However, in other embodiments a symmetric encryption technique is used. Thus, the same encryption key may be used to sign, encrypt and/or decrypt the certified, secure data package.

In some embodiments, the one or more program modules 424 includes a data-sharing application. This data-sharing application may receive, via networking subsystem 414, authorization information for a recipient of sensor data and/or analyzed sensor data. In response to the authorization information, the data-sharing application may provide, via networking subsystem 414, the requested sensor data and/or analyzed sensor data to the recipient. Alternatively, the data-sharing application may provide, via networking subsystem 414, a pointer to a location in memory subsystem 412 where the recipient can access the requested sensor data and/or analyzed sensor data. Note that the data-sharing application may also optionally provide the optional protection information 522 (FIG. 5) to the recipient (which may allow the recipient to confirm the source(s) and/or to unprotect protected information).

Additionally, in some embodiments the one or more program modules 424 includes a notification application. This notification application may receive, via networking subsystem 414, information, such as feedback associated with one or more environmental conditions in environment 112 (FIG. 1) and/or a notification (such as a maintenance notification). In response, the notification application may communicate, via networking subsystem 414, the information and/or one or more reports based on the information (such as daily, weekly or monthly summaries of analyzed sensor data, which may be included in documents or files) to: one or more of environmental monitoring devices 110 (FIG. 1), data-sharing electronic device 118 (FIG. 1) and/or other electronic devices (such as computers or servers associated with or operated on behalf of: component suppliers, retailers, insurance companies, security personnel, emergency service personnel, maintenance organizations, shipping companies, landlords or property owners, a corporate-compliance organization, inspectors, businesses, government agencies, etc.). For example, the communication of the information may utilize a Short Message Service, email, a social network and/or a message service with a restricted number of characters per message. In some embodiments, a link to purchase a product or service in response to an event can be included in the notification, e.g., a low battery notification can provide a link to an online ordering form and a prepaid account at a retailer, so that new batteries can be ordered from the retailer directly via the link included in the notification. Similarly, a service can be arranged and/or scheduled, e.g., cleaning of a pool filter can be arranged and scheduled via a link included in a notification. Alternatively, the information may be posted to a web page or website (and, more generally, a location on a network), and one or more recipients may be notified via networking subsystem 414, e.g., a link to the location may be provided to the recipients.

When the notification includes a maintenance notification, the archiving application may store information specifying the maintenance notification in a historical record or log for the environment. In addition, the archiving application may store any subsequent remedial action (such as a repair or service performed on an electronic device in the environment) in a historical record or log for the environment in memory subsystem 412.

Within electronic device 400, processing subsystem 410, memory subsystem 412, and/or networking subsystem 414 may be coupled using one or more interconnects, such as bus 420. These interconnects may include an electrical, optical, and/or electro-optical connection that the subsystems can use to communicate commands and data among one another. Note that different embodiments can include a different number or configuration of electrical, optical, and/or electro-optical connections among the subsystems.

Electronic device 400 can be (or can be included in) any electronic device with at least one network interface. For example, electronic device 400 can be (or can be included in): a sensor (such as a smart sensor), a tablet computer, a smartphone, a cellular telephone, an appliance, a regulator device, a consumer-electronic device, a portable computing device, test equipment, a digital signal processor, a controller, a personal digital assistant, a facsimile machine, a laser printer (or other office equipment such as a photocopier), a personal organizer, a toy, a set-top box, a computing device (such as a laptop computer, a desktop computer, a server, and/or a sub-notebook/netbook), an alarm, a light (such as a nightlight), a monitoring device, and/or another electronic device.

Although specific components are used to describe electronic device 400, in alternative embodiments, different components and/or subsystems may be present in electronic device 400. For example, electronic device 400 may include one or more additional processing subsystems, memory subsystems, and/or networking subsystems. Additionally, one or more of the subsystems may not be present in electronic device 400. Moreover, in some embodiments, electronic device 400 may include one or more additional subsystems that are not shown in FIG. 4, such as a power supply and/or a user-interface subsystem (which a user may use to modify settings of one or more of environmental monitoring devices 110 in FIG. 1, such as settings for alarms or notifications). Although separate subsystems are shown in FIG. 4, in some embodiments, some or all of a given subsystem or component can be integrated into one or more of the other subsystems or components in electronic device 400. For example, in some embodiments the one or more program modules 424 are included in operating system 422.

Moreover, the circuits and components in electronic device 400 may be implemented using any combination of analog and/or digital circuitry, including: bipolar, PMOS and/or NMOS gates or transistors. Furthermore, signals in these embodiments may include digital signals that have approximately discrete values and/or analog signals that have continuous values. Additionally, components and circuits may be single-ended or differential, and power supplies may be unipolar or bipolar.

Note that an integrated circuit may implement some or all of the functionality of electronic device 400.

While some of the operations in the preceding embodiments were implemented in hardware or software, in general the operations in the preceding embodiments can be implemented in a wide variety of configurations and architectures. Therefore, some or all of the operations in the preceding embodiments may be performed in hardware, in software or both.

Figure 6:
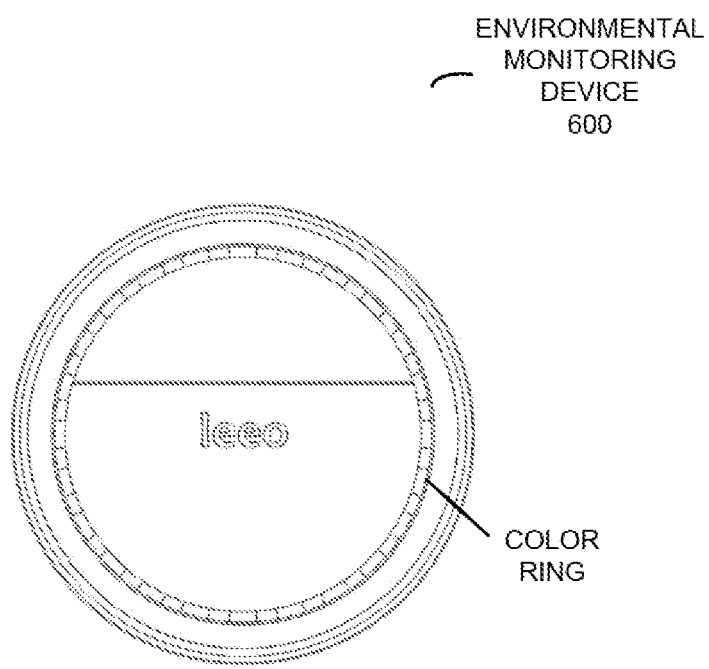
FIG. 6 is a drawing illustrating a front view of an environmental monitoring device in FIG. 1 in accordance with an embodiment of the present disclosure.
Figure 7:
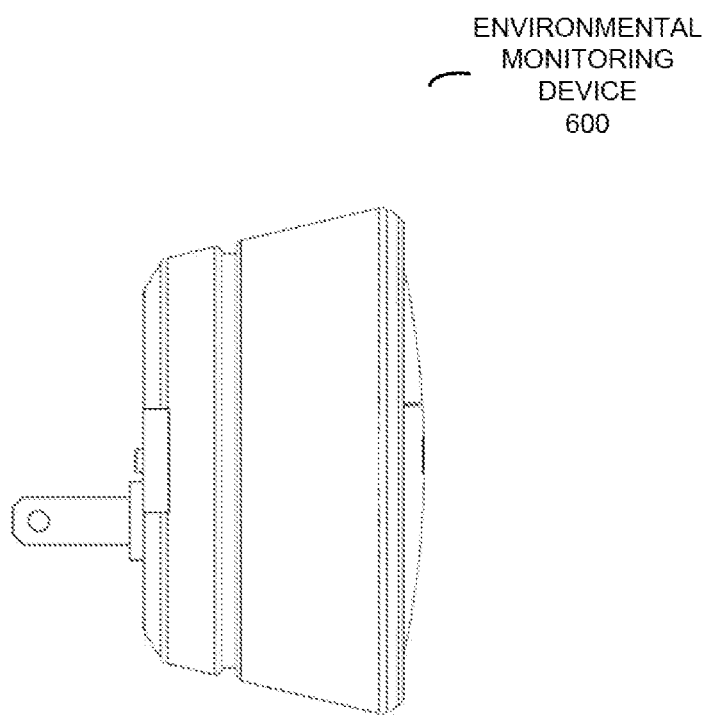
FIG. 7 is a drawing illustrating a side view of the environmental monitoring device in FIG. 6 in accordance with an embodiment of the present disclosure.
Figure 8:
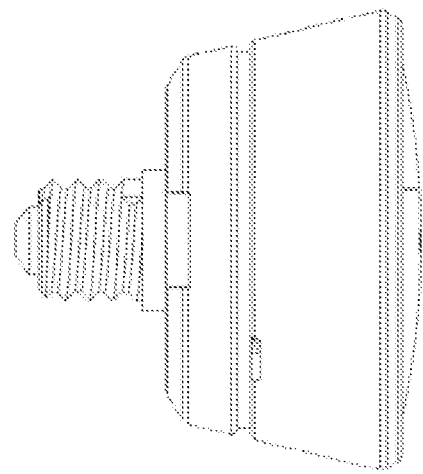
FIG. 8 is a drawing illustrating a side view of the environmental monitoring device in FIG. 6 in accordance with an embodiment of the present disclosure.
Figure 9:
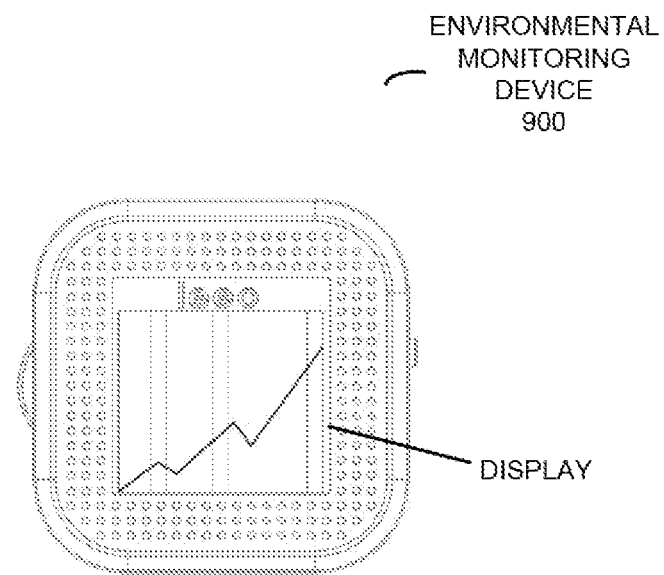
FIG. 9 is a drawing illustrating a front view of an environmental monitoring device in FIG. 1 in accordance with an embodiment of the present disclosure.
Figure 10:
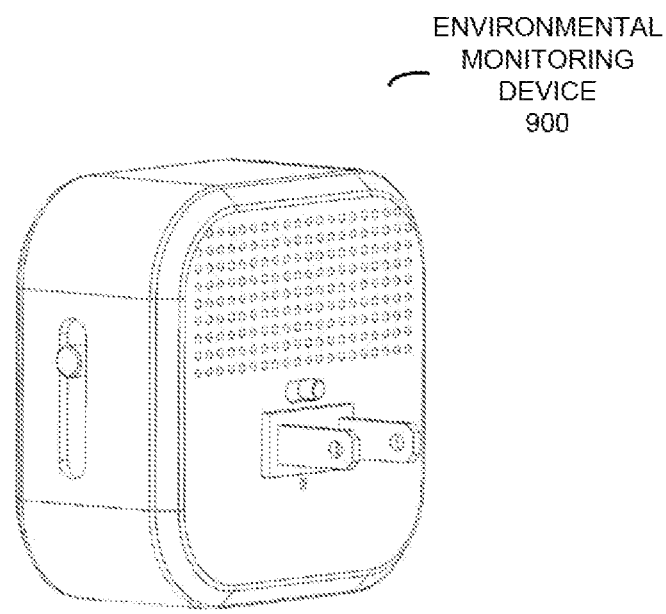
FIG. 10 is a drawing illustrating a side view of the environmental monitoring device in FIG. 9 in accordance with an embodiment of the present disclosure.

An exemplary embodiment of the environmental monitoring device is shown in FIGS. 6-8, which respectively show front, and side views of environmental monitoring device 600, which may be one of environmental monitoring devices 110 (FIG. 1). Alternatively, the environmental monitoring device may include a display. This shown in FIGS. 9 and 10, which respectively show front and side views of environmental monitoring device 900, which may be one of environmental monitoring devices 110 (FIG. 1).

Embodiments of the environmental monitoring device may include a grating in the chassis or housing (such as a case or a shell on the outside of the environmental monitoring device) that prevents large particles, soil and mud from damaging or otherwise obscuring inputs to one or more sensor devices in the environmental monitoring device. Alternatively or additionally, the chassis or housing may facilitate airflow or fluid flow through vents or openings to one or more sensor devices in the environmental monitoring device. In addition, the environmental monitoring device may include a forced-fluid driver (such as a fan) to facilitate airflow or fluid-flow through the vents. However, in other embodiments airflow or fluid flow is facilitated using convection (e.g., by heating the air or the fluid), or the airflow or fluid flow may occur passively.

A wide variety of materials may be used to fabricate the environmental monitoring device (and, in particular, the housing or chassis of the environmental monitoring device), including: organic materials (such as plastic, polyethylene, wood, etc.), inorganic materials (such as a metal), glass, concrete, rubber, a semiconductor, a fabric, etc. Moreover, the housing or chassis may be transparent or opaque.

Figure 11:
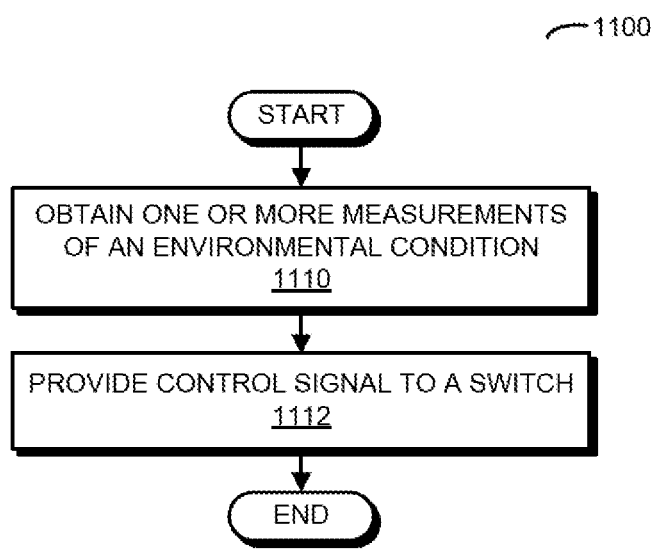
FIG. 11 is a flow diagram illustrating a method for selectively electrically coupling a first electrical-connection node and a second electrical-connection node in accordance with an embodiment of the present disclosure.

We now further describe operation of the environmental monitoring device and, in particular, functionality of the environmental monitoring device in various embodiments. FIG. 11 presents a flow diagram illustrating a method 1100 for selectively electrically coupling a first electrical-connection node and a second electrical-connection node, which may be performed by the environmental monitoring device. During operation, the environmental monitoring device obtains one or more measurements of an environmental condition (operation 1110) in an external environment that includes the environmental monitoring device. For example, a sensor (or a sensor mechanism) in the environmental monitoring device may optionally provide sensor data based on the one or more measurements of the environmental condition and/or the sensor data may be optionally received from an electronic device that is separate from the environmental monitoring device (such as another environmental monitoring device and/or a legacy electronic device in the external environment, which is sometimes referred to as a 'fourth electronic device'). Note that the sensor may include: a temperature sensor, a humidity sensor, an acoustic sensor, a fire-detection sensor, a load-monitoring sensor, and/or a motion sensor:

Then, a processor (and, more generally, a control mechanism, which may include an integrated circuit or control logic) in the environmental monitoring device, provides a control signal to a switch (operation 1112) or a switching mechanism in the environmental monitoring device to selectively electrically couple the first electrical-connection node and the second electrical-connection node in the environmental monitoring device based on the one or more measurements of the environmental condition. This may selectively electrically couple an electronic device (which is electrically coupled to the first electrical-connection node) to a second electronic device (which is electrically coupled to the second electrical-connection node). Note that the electronic device and/or the second electronic device may be one of the electronic devices in FIG. 1, such as a legacy electronic device, a regulator device, an appliance, a light source (such as a lamp or a light bulb), etc. Thus, method 1100 may allow the environmental monitoring device to turn the electronic device and/or the second electronic device on or off (and, more generally, to modify the function of the electronic device and/or the second electronic device) without or excluding interaction (such as communication and/or electrical coupling of instructions) between environmental monitoring devices 110 and the electronic device and/or the second electronic device.

For example, the sensor may include an acoustic sensor and the environmental condition may include a sound in the external environment. In this example, the processor may selectively electrically decouple the first electrical-connection node and the second electrical-connection node when the sound exceeds a threshold value (such as 30-40 dB), and may selectively electrically couple the first electrical-connection node and the second electrical-connection node when the sound is less than the threshold value. Thus, the processor may change the control signal based on the presence or absence of the sound, such as: during a telephone call, when a door is opened or closed (such as when someone comes into or leaves a room), or when an alarm occurs (such as when a fire alarm or a carbon-monoxide detector is activated). Alternatively or additionally, the sensor may include a fire-detection sensor (or a carbon-monoxide detector) and the environmental condition may include presence of fire (or carbon monoxide). In this example, the processor may selectively electrically decouple the first electrical-connection node from the second electrical-connection node when the presence of fire (or carbon monoxide) is detected.

In another example, the sensor may include a load-monitoring sensor and the environmental condition may include an electrical characteristic associated with the electronic device and/or the second electronic device. Then, the processor may selectively electrically decouple the first electrical-connection node from the second electrical-connection node when the electrical characteristic indicates a standby operating mode for the electronic device and/or the second electronic device. This may allow the environmental monitoring device to reduce or eliminate so-called 'vampire,' 'phantom' or 'parasitic' power consumption or waste. Alternatively or additionally, the selective electrical decoupling may occur when the electrical characteristic indicates a safety concern, such as: a fire hazard, a short circuit, a risk of electric shock or electrocution, etc.

In general, the switch may be an electronic (such as an electrically operated switch or relay) or an electromechanical component that can interrupt a circuit and/or divert current from the first electrical-connector node to the second electrical-connector node. For example, the switch may be single pole or multiple pole, and may (or may not) be make before break. Thus, the switch may selectively switch between a closed state and an open state.

In some embodiments, the switch regulates the electrical coupling. For example, the switch may provide voltage-limited or current-limited coupling between the first electrical-connection node and the second electrical-connection node. This may be accomplished using a voltage clamp (such as a diode) in parallel with a load (such as the electronic device or the second electronic device) or with a circuit that includes combination of active and passive elements (such as diodes, transistors, etc.).

In some embodiments, the selective electrical coupling includes an impedance value between the impedance values when the electrical coupling corresponds to the open state of the switch and when the electrical coupling corresponds to the closed state of the switch. For example, the impedance of the switch may be electronically selected by the control signal to have values between a maximum (open state) and a minimum (closed state) impedance of the switch. This may allow the switch to function as a dimmer switch. Consequently, the control signal may correspond to a grey-scale value associated with the impedance value.

At least one of the first electrical-connection node and the second electrical-connection node may include: a light socket, a rotatable connector configured to electrically couple to a light socket, an AC power plug, an AC power socket, a multi-wire electrical terminal, a DC power plug, a DC power socket, and/or a USB-compatible connector. Thus, the first electrical-connection node and/or the second electrical-connection node may include male connectors, female connectors and/or wires. For example, the first electrical-connection node may include a multi-wire electrical terminal, and the second electrical-connection node may include: a light socket, a rotatable connector configured to electrically couple to a light socket, an AC power plug, an AC power socket, a multi-wire electrical terminal, a DC power plug, a DC power socket, and/or a USB-compatible connector. Note that the environmental monitoring device may be used in conjunction with a variety of electrical standards. Thus, the first electrical-connection node may correspond to a first electrical standard having a first root-mean-square voltage (such as 230 V and a fundamental frequency of 50 Hz, which is used in the European Union) and the second electrical-connection node may correspond to a second electrical standard having a second root-mean-square voltage (such as 120 V and a fundamental frequency of 60 Hz, which is used in North America). Consequently, the environmental monitoring device may include a transformer. In some embodiments, the environmental monitoring device accepts three-phase electric power and outputs electrical power according to one or more electrical standards.

While the environmental monitoring device may function independently or without direct communication with the other electronic devices in FIG. 1, in other embodiments the environmental monitoring device works in conjunction with one or more electronic devices that are remotely located or separate from the environmental monitoring device. For example, the environmental monitoring device may include: an antenna, and an interface circuit that communicates with a third electronic device (such as a cellular telephone of the user) that is separate from the environmental monitoring device. This communication may include an identifier of the third electronic device, and the control mechanism may selectively electrically couple the first electrical-connection node and the second electrical-connection node based on the identifier. For example, the identifier may include a media access control (MAC) address of the user's cellular telephone, the user's cellular-telephone number or information specifying the user's account (such as an account number) with a provider of the environmental monitoring device. Then, the selective electrical coupling may be based on the identifier. Thus, the switch may be actuated when the user is in proximity to the environmental monitoring device (such as when the user is within 1-10 m) or is in the external environment (such as, when the environmental monitoring device infers that the user arrived at home, the lights may be turned on).

More generally, the identifier may allow the environmental monitoring device to personalize the environmental condition based on who is in or is expected to be in the external environment. To do so, the processor in the environmental monitoring device may access or obtain a predefined preference of an individual associated with the identifier (such as the user or someone other than the user). In particular, the processor may access one or more locally or remotely stored preferences of the individual, such as those stored in the user's account information. The selective electrical coupling may then be based on the one or more predefined preferences. For example, the predefined preference may specify a threshold value for the environmental condition (such as a maximum temperature of 80 F or a minimum temperature of 65 F, a maximum humidity of 80% or a minimum humidity of 30%, a maximum or a minimum concentration of a chemical or an allergen in the external environment, etc.), and the switch may selectively electrically couple the first electrical-connection node and the second electrical-connection node based on the threshold value. In this way, a regulator device (such as a fan, an air conditioner, a heater, an air filter, a humidifier, etc.) may be selectively activated. Alternatively or additionally, the predefined preference may be related to a medical condition of the user or an illumination preference (such as desired lighting conditions at a particular time of day). Note that instead of accessing or obtaining the predefined preference of the individual, the preference may be included in the communication (i.e., may be received using the antenna and the interface circuit), and the selective electrical coupling may be based on the preference.

While preceding discussion illustrated selective electrical coupling based on a static or fixed preference, more generally, the preference may evolve or change as a function of time or the environmental condition, which may allow the environmental monitoring device to dynamically respond to or control the environmental condition.

In these ways, the environmental monitoring device may facilitate dynamic switching based on one or more environmental conditions, the presence (or absence) of the individual and/or one or more preferences of the individual. Consequently, the environmental monitoring device may provide improved ways to monitor and modify the environmental conditions in the external environment.

Figure 12:
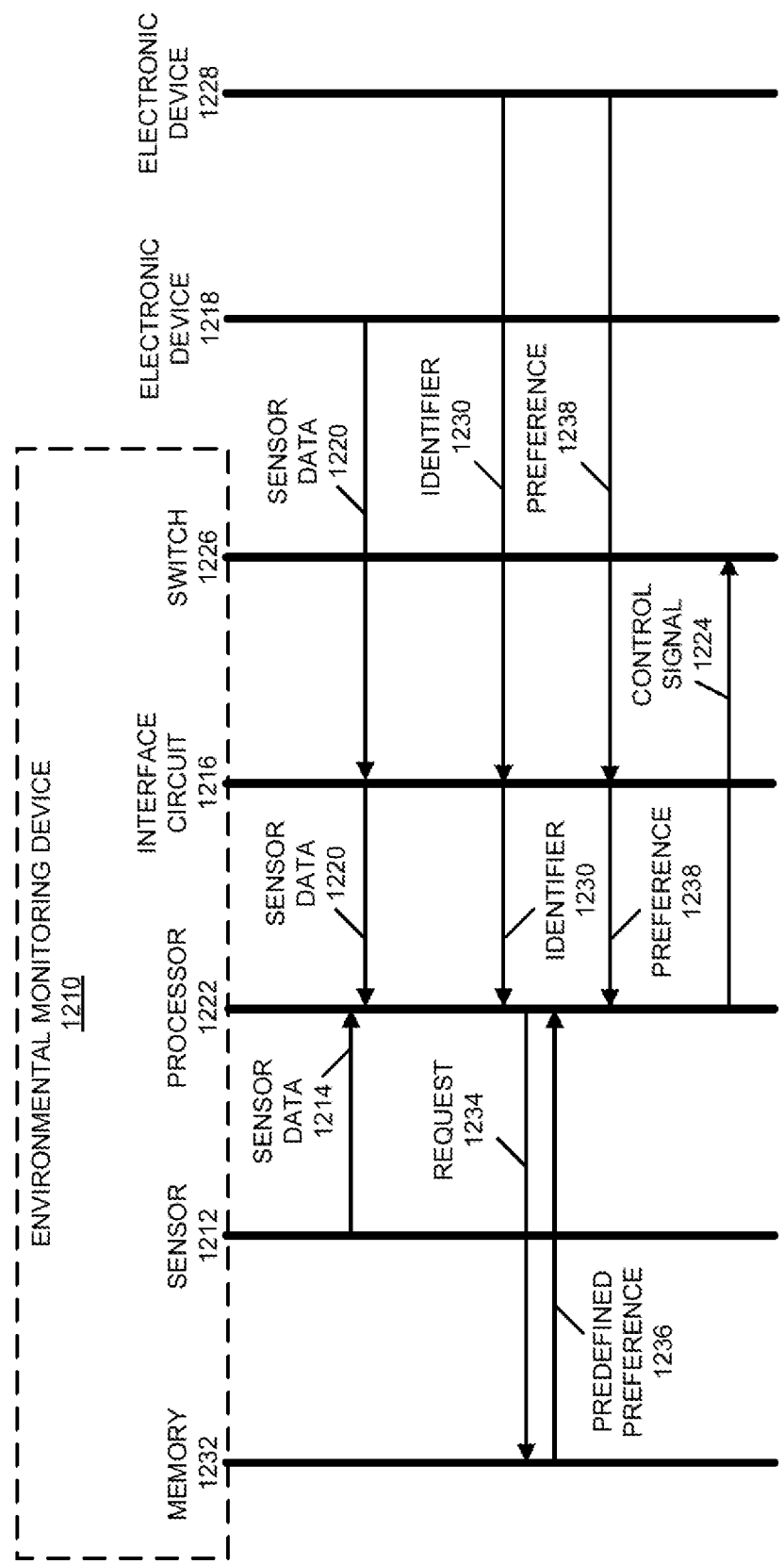
FIG. 12 is a drawing illustrating communication within an environmental monitoring device during the method of FIG. 11 in accordance with an embodiment of the present disclosure.

FIG. 12 presents a drawing illustrating communication within environmental monitoring device 1210 during method 1100 (FIG. 11). During operation of environmental monitoring device 1210 (such as during an environmentally gated switching mode of operation), sensor 1212 optionally provides sensor data 1214 to processor 1222 based on the one or more measurements of the environmental condition. Alternatively or additionally, interface circuit 1216 optionally receives sensor data 1220 based on the one or more measurements of the environmental condition from electronic device 1218 (such as a legacy electronic device or another environmental monitoring device) and provides sensor data 1220 to processor 1222.

Then, processor 1222 provides control signal 1224 to a switch 1226 to selectively electrically couple the first electrical-connection node and the second electrical-connection node in the environmental monitoring device based on the one or more measurements of the environmental condition.

In some embodiments, interface circuit 1216 optionally receives identifier 1230 from electronic device 1228 (such as the user's cellular telephone). In response, processor 1222 may optionally access or obtain predefined preference 1236 from memory 1232 based on identifier 1230. For example, processor 1222 may receive predefined preference 1234 in response to request 1234. Alternatively, interface circuit 1216 may optionally receive preference 1238 from electronic device 1228 (for example, the user may provide preference 1236 using a user interface in electronic device 1228), which interface circuit 1216 then provides to processor 1222. Consequently, processor 1222 may optionally base control signal 1224 on: identifier 1230, predefined preference 1236 and/or preference 1238.

Figure 13:
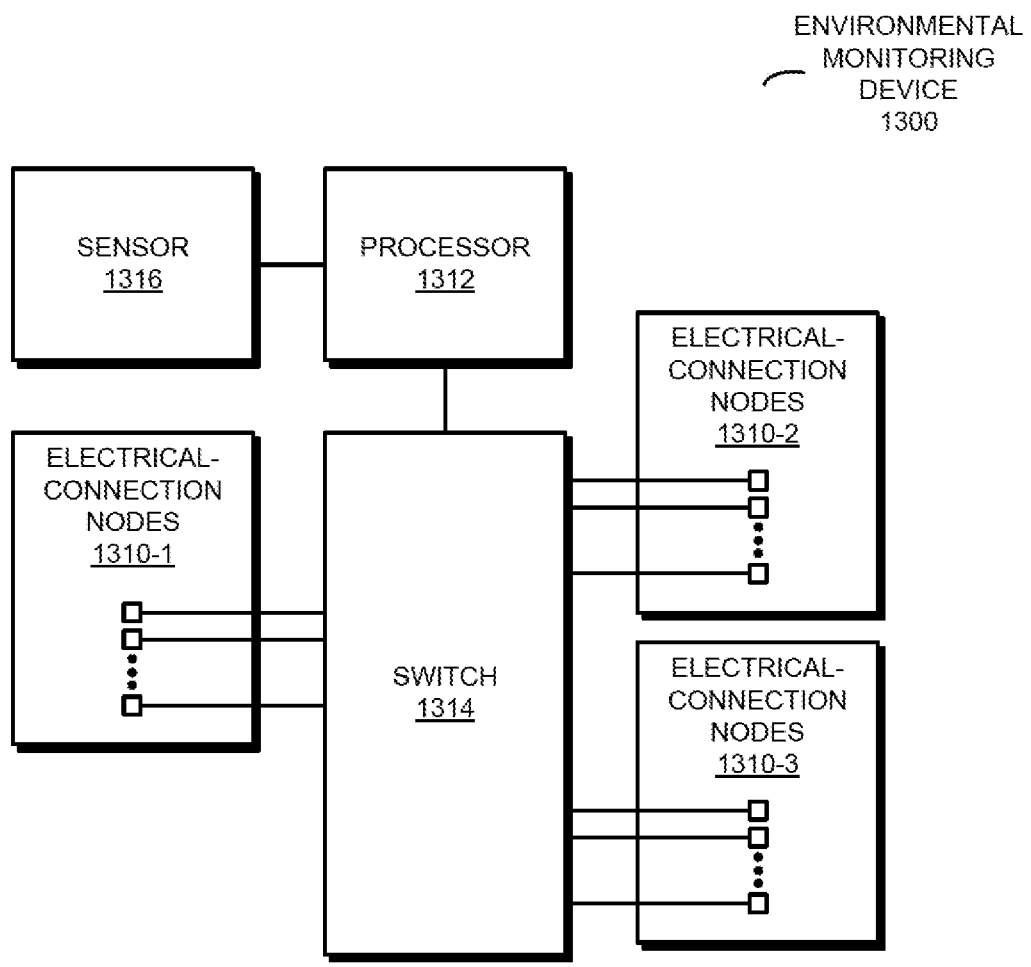
FIG. 13 is a block diagram illustrating a switch in an environmental monitoring device during the method of FIG. 11 in accordance with an embodiment of the present disclosure.

While the preceding discussion illustrated the environmental monitoring device with two electrical-connection nodes, in some embodiments the environmental monitoring device includes one or more additional electrical-connection nodes. For example, as shown in FIG. 13, which presents a block diagram illustrating a switch 1314 (or switching mechanism) in environmental monitoring device 1300 during method 1100 (FIG. 11). During operation, environmental monitoring device 1300 may include electrical-connection nodes 1310, and based on the control signal from processor 1312 (which is based on the one or more measurements of the environmental condition by sensor 1316), switch 1314 may selectively electrically couple electrical-connection node 1310-1, electrical-connection node 1310-2 and/or electrical-connection node 1310-3. In some embodiments, the selective electrical coupling of electrical-connection nodes 1310-1 and 1310-2 and the selective electrical coupling of electrical-connection nodes 1310-1 and 1310-3 are independent of each other (e.g., electrical-connection nodes 1310-1 and 1310-2 may be selectively electrically coupled whether or not electrical-connection nodes 1310-1 and 1310-3 are selectively electrically coupled). Alternatively, the selective electrical coupling of electrical-connection nodes 1310-1 and 1310-2 and the selective electrical coupling of electrical-connection nodes 1310-1 and 1310-3 may depend on each other (such as concurrent or alternating electrical coupling). Thus, when electrical-connection nodes 1310-1 and 1310-2 are electrically coupled electrical-connection nodes 1310-1 and 1310-3 may be electrically decoupled, and when electrical-connection nodes 1310-1 and 1310-2 are electrically decoupled electrical-connection nodes 1310-1 and 1310-3 may be electrically coupled. For example, the electronic devices electrically coupled to electrical-connection nodes 1310-2 and 1310-3 may have opposite functions, which may allow push-pull regulation of the environmental condition in the external environment.

Figure 14:
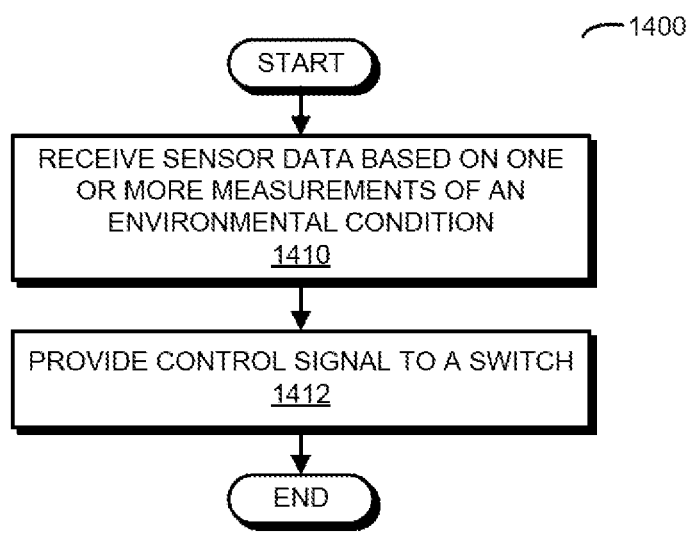
FIG. 14 is a flow diagram illustrating a method for selectively electrically coupling a first electrical-connection node and a second electrical-connection node in accordance with an embodiment of the present disclosure.

In some embodiments, the selective electrical coupling is based on or facilitates charging of the rechargeable battery. This is shown in FIG. 14, which presents a flow diagram illustrating a method 1400 for selectively electrically coupling the first electrical-connection node and the second electrical-connection node, which may be performed by the environmental monitoring device. During operation, the environmental monitoring device receives (or obtains) the sensor data based on the one or more measurements of the environmental condition (operation 1410) from the sensor (or the sensor mechanism) in the environmental monitoring device, where the environmental condition is associated with the charging of the rechargeable battery. For example, the first electrical-connection node may be electrically coupled to a power source, and the second electrical-connection node may be electrically coupled to the electronic device (or the second electronic device) that includes the rechargeable battery. Note that the rechargeable battery may include one or more electrochemical cells that store energy, such as: a lithium-ion battery, a nickel-metal-hydride battery, etc.

Then, the processor (or the control mechanism) in the environmental monitoring device provides the control signal to the switch (operation 1412) or the switching mechanism in the environmental monitoring device to selectively electrically couple the first electrical-connection node and the second electrical-connection node based on the one or more measurements of the environmental condition. Moreover, the processor selects the charging mode of the rechargeable battery based on the one or more measurements of the environmental condition.

For example, the charging mode may include: a charging profile as a function of time that increase life of the rechargeable battery (e.g., by avoiding excess current, using pulsed charging and/or avoiding overcharging, such as by using a delta-V or delta-peak-voltage charging circuit), a charging profile as a function of time that reduces a charging time of the rechargeable battery, and/or a charging profile as a function of time that reduces power consumption while charging the rechargeable battery. Thus, the environmental condition may include: the current through the rechargeable battery, the voltage across the rechargeable battery, the temperature of the rechargeable battery (or a thermal signature or a thermal image of the rechargeable battery), an internal impedance of the rechargeable battery and/or, more generally (as described further below), an electrical characteristic of the rechargeable battery. In particular, the environmental condition may include an infrared image of the rechargeable battery, which may allow hot spots or the temperature of the rechargeable battery to be determined, which, in turn, may allow intelligent or smart charging of the rechargeable battery to increase its life. Alternatively, the environmental condition may include the voltage across, the current through and/or the impedance of one or more electrochemical cells in the rechargeable battery (e.g., the voltage, current and/or impedance of individual electrochemical cells in the rechargeable battery may be directly measured or may be indirectly inferred), which may allow the rechargeable battery to be charged quickly and safely.

In some embodiments, the sensor includes a load-monitoring sensor and the environmental condition may include the electrical characteristic associated with the rechargeable battery, the electronic device and/or the second electronic device. Then, the processor may selectively electrically decouple the first electrical-connection node from the second electrical-connection node when the electrical characteristic indicates the standby operating mode for the electronic device and/or the second electronic device. Alternatively or additionally, the selective electrical decoupling may occur when the electrical characteristic indicates a safety concern (such as a fire hazard, a short circuit, a risk of electric shock or electrocution, etc.). Note that the electrical characteristic may include: a current, a voltage, a phase relative to at least a reference signal (such as a power-line signal or a clock signal), a quality factor, a harmonic of a fundamental frequency, a resonance frequency, a time constant, noise, and/or power consumption. For example, the electrical characteristic may include a root-mean-square electrical noise and/or the ratio of energy associated with harmonics to the energy at the fundamental frequency (such as a clock frequency) output on a power line or a signal line electrically coupled to the electronic device and/or the second electronic device.

The electrical characteristic (and, more generally, the one or more measurements of the environmental condition) may be used by the processor to predict failure of at least a component in the electronic device and/or the second electronic device. For example, an increase in the root-mean-square electrical or acoustic noise, the ratio of energy associated with harmonics to the energy at the fundamental frequency, and/or the power consumption as a function of time may indicate an impending failure of at least the component. Alternatively, the electrical characteristic may include the absolute or a relative change in the charging time under certain charging conditions (such as the voltage, the current, the pulse rise time, the pulse duration, the pulse amplitude, the pulse frequency, etc.), the charging mode, the total charge, etc., which may indicate an impending failure of the rechargeable battery. (Note that 'failure' may be defined as a failure to operate, a safety condition and, more generally, exceeding at least one specified operating range of a parameter associated with the component.) In some embodiments, the predicted failure is based on sensor data output from a chemical sensor, an optical sensor and/or a fire-detection sensor.

Predicting an impending failure may be facilitated by the processor (or an integrated circuit or control logic) in the environmental monitoring device determining information associated with the electronic device and/or the second electronic device. Note that the information may include: a type of electronic device, a model of electronic device, a brand of electronic device, and/or a unique identifier of the electronic device and/or the second electronic device. Using the information, the processor may also access or obtained a predefined device profile stored in local or remote memory that includes information about the electronic device and/or the second electronic device (such as specifications and/or components in the electronic device and/or the second electronic device, predictive models of component lifetime or failure rates, etc.).

Figure 15:
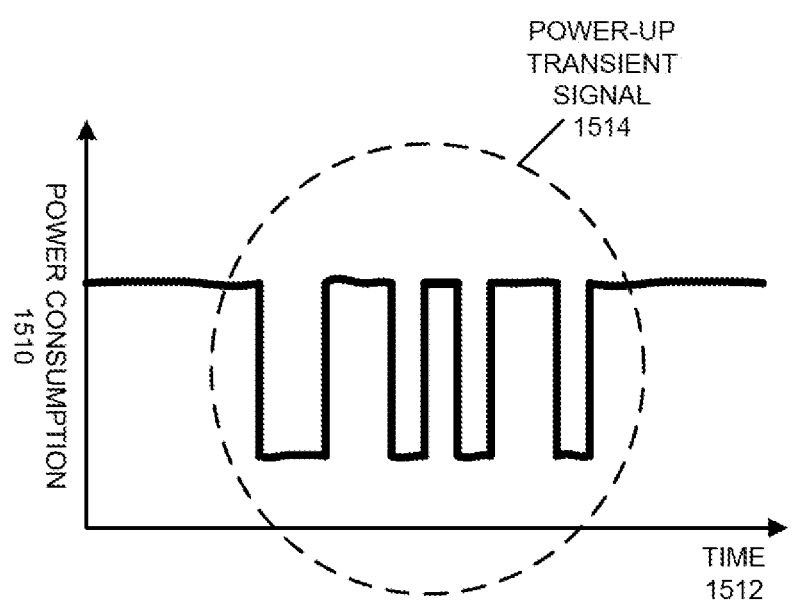
FIG. 15 is a drawing illustrating identification of an environmental monitoring device in accordance with an embodiment of the present disclosure.

In particular, the processor may determine the information based on the one or more measurements of the environmental condition during operation of the electronic device and/or the second electronic device. For example, the environmental condition may be associated with a power-up transient signal of the electronic device and/or the second electronic device. As shown in FIG. 15, power-up transient signal 1514 may include a power consumption 1510 that varies with time 1512 (which is sometimes referred to as a 'time-varying power consumption') and is associated with a programmed electrical characteristic of the electronic device and/or the second electronic device. In particular, the time-varying power consumption may include a sequence two or more discrete (or approximately discrete) power-consumption levels. These power-consumption levels may be associated with operation of an integrated circuit in the electronic device and/or the second electronic device based on a predefined identifier, such as execution of a program module by a processor in the electronic device and/or the second electronic device (e.g., initialization of firmware by the processor, selectively activating a circuit or block in the processor to vary the power consumption as a function of time, etc.). Moreover, the power-consumption levels may correspond to (or represent): a pulse-code modulation sequence, a quadrature-modulation sequence, and/or a DC-balanced sequence. Thus, the power-consumption levels may represent digital values in the predefined identifier. In some embodiments, the power-consumption levels include information encoded with: an error-detection code, a parity-bit technique, a checksum, a hash function, a cyclic-redundancy check, a hamming code, and/or an error-correction code. While FIG. 15 illustrates a particular type of coding, in other embodiments other codes and/or modulation techniques may be used, including: amplitude modulation, frequency modulation and/or spread-spectrum modulation. In addition, while FIG. 15 illustrates a particular example of the time-varying power consumption, more generally the time-varying power consumption includes a modulated waveform.

Thus, by determining the information, the processor may recognize classes of electronic devices, and may monitor aging of the electronic device and/or the second electronic device. When impending failure is predicted (or a failure is detected), the environmental monitoring device may provide an alert to the user. The environmental monitoring device may also perform remedial action, such as: ordering a replacement component or electronic device, schedule maintenance, etc.

In some embodiments, the processor may associate a user (and, more generally, an individual) with the determined information based a predefined list of electronic devices of the user. For example, user-account information may include the predefined list of the user's electronic devices. If the determined information specifies a unique identifier of an electronic device, the processor may use this information and the predefined list to lookup the user. Then, the processor may obtain or access a predefined preference of the user. As described previously with reference to FIG. 11, the selective electrical coupling of the first electrical-connection node and the second electrical-connection node may be based on this predefined preference.

While the preceding embodiments illustrated the identification of the electronic device and/or the second electronic device (as well as associated information, such as a type, model or brand), e.g., by measuring the programmed electrical characteristic, in other embodiments the identity of the electronic device and/or the second electronic device (or the associated information) is determined based on the selective electrical coupling. For example, an electrical characteristic measured by a load-monitoring sensor may be associated with a predefined device profile, which may include metadata that facilitates the identification. This association may also be based on a location of the environmental monitoring device (such as in the bathroom), which may facilitate the identification. In some embodiments, the user of the environmental monitoring device is queried to facilitate the identification. For example, the user may be asked (e.g., via communication with the user's cellular telephone) to identify the electronic device and/or the second electronic device. Alternatively or additionally, the user may be asked to provide a name (such as a nick name) for the electronic device and/or the second electronic device.

Furthermore, changes to the environmental condition (such as a change in the temperature or the humidity) after a change in the selective electrical coupling may facilitate the identification. For example, the presence (or absence) of sound after the first electrical-connection node is electrically coupled to (or electrically decoupled from) the second electrical-connection node may facilitate identification of the electronic device and/or the second electronic device as stereo equipment. Similarly, a change in the temperature after the first electrical-connection node is electrically coupled to (or electrically decoupled from) the second electrical-connection node may facilitate identification of the electronic device and/or the second electronic device as a thermostat. Furthermore, a change in the humidity after the first electrical-connection node is electrically coupled to (or electrically decoupled from) the second electrical-connection node may facilitate identification of the electronic device and/or the second electronic device as a humidifier.

Figure 16:
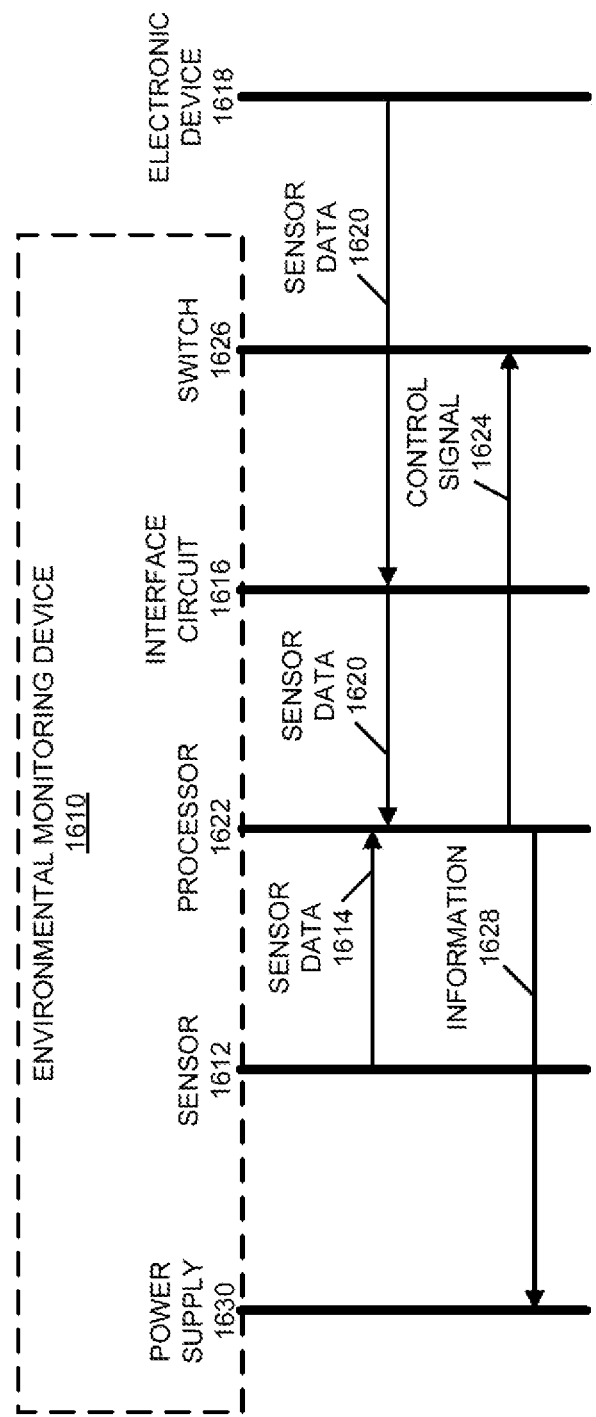
FIG. 16 is a drawing illustrating communication within an environmental monitoring device during the method of FIG. 14 in accordance with an embodiment of the present disclosure.

FIG. 16 presents a drawing illustrating communication within environmental monitoring device 1610 during method 1400 (FIG. 41). During operation of environmental monitoring device 1610 (such as during an environmentally gated switching mode of operation), sensor 1612 optionally provides sensor data 1614 to processor 1622 based on the one or more measurements of the environmental condition. Alternatively or additionally, interface circuit 1616 optionally receives sensor data 1620 based on the one or more measurements of the environmental condition from electronic device 1618 (such as a legacy electronic device or another environmental monitoring device), which provides sensor data 1620 to processor 1622. Note that the environmental condition may be associated with the charging of the rechargeable battery.

Figure 17:
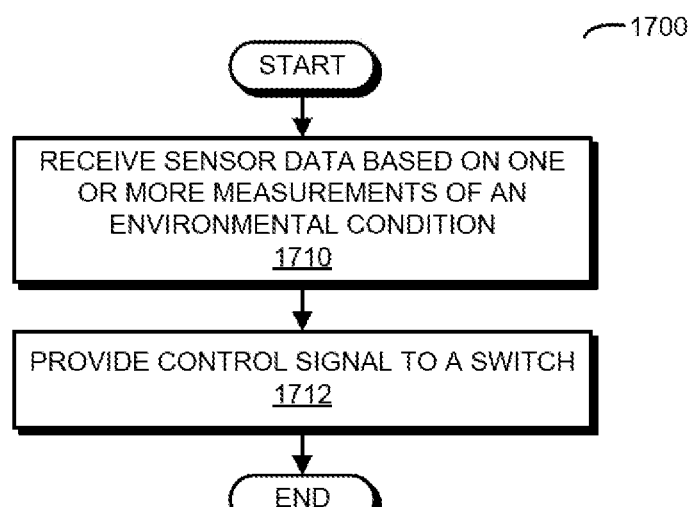
FIG. 17 is a flow diagram illustrating a method for selectively electrically coupling a first electrical-connection node and a second electrical-connection node in accordance with an embodiment of the present disclosure.

Then, processor 1622 provides control signal 1624 to a switch 1626 to selectively electrically couple the first electrical-connection node and the second electrical-connection node in the environmental monitoring device based on the one or more measurements of the environmental condition. In this way, processor 1622 selects the charging mode of the rechargeable battery based on the one or more measurements of the environmental condition. Alternatively or additionally to the selective electrical coupling, processor 1622 optionally provides information 1628 specifying the charging mode to power supply 1630, which then accordingly recharges the rechargeable battery:

In some embodiments, the environmental monitoring device receives the sensor data from a remotely located or separate electronic device. This is shown in FIG. 17, which presents a flow diagram illustrating a method 1700 for selectively electrically coupling the first electrical-connection node and the second electrical-connection node, which may be performed by the environmental monitoring device. During operation, the environmental monitoring device receives, from another electronic device (such as the fourth electronic device), the sensor data based on the one or more measurements of the environmental condition (operation 1710) in the external environment that includes the environmental monitoring device. For example, the environmental monitoring device may communicate with the fourth electronic device via the antenna and the interface circuit. The fourth electronic device may be separate from the environmental monitoring device, such as a legacy electronic device and/or another environmental monitoring device. Moreover, the fourth electronic device may include a sensor (or sensor mechanism) that performs the one or more measurements. Note that the sensor data may include: temperature, humidity, acoustic information, fire-detection information, load-monitoring information, and/or motion information.

Then, the processor (or the control mechanism) in the environmental monitoring device provides the control signal to the switch (operation 1712) or the switching mechanism in the environmental monitoring device to selectively electrically couple the first electrical-connection node and the second electrical-connection node based on the one or more measurements of the environmental condition.

For example, as noted previously in the discussion of FIG. 11, the sensor data may include acoustic information (such as audio information) and the environmental condition may include a sound in the external environment. Thus, the processor may change the control signal based on the presence or absence of the sound. Alternatively or additionally, the sensor data may include fire-detection information (or a carbon-monoxide concentration) and the environmental condition may include presence of fire (or carbon monoxide). In this example, the processor may selectively electrically decouple the first electrical-connection node from the second electrical-connection node when the presence of fire (or carbon monoxide) is detected.

In another example, the sensor data may include load-monitoring information and the environmental condition may include the electrical characteristic associated with the electronic device and/or the second electronic device. Then, the processor may selectively electrically decouple the first electrical-connection node from the second electrical-connection node when the electrical characteristic indicates a safety concern (such as a fire hazard, a short circuit, a risk of electric shock or electrocution, etc.) or a standby operating mode for the electronic device and/or the second electronic device.

Note that the switch may provide selectively switching between a closed state of the switch and an open state of the switch. Alternatively, the selective electrical coupling may include the impedance value between the open-state impedance value and the close-state impedance value. Furthermore, the switch may regulate the electrical coupling, such as by providing voltage-limited or current-limited coupling. In addition, the environmental monitoring device may be used in conjunction with a variety of electrical standards. As described previously with reference to FIG. 13, the switch may include multiple electrical-connection nodes that are independently or dependently (such as concurrently) selectively electrically coupled.

Additionally, the environmental monitoring device may communicate with the third electronic device (via the antenna and the interface circuit) that is separate from the environmental monitoring device, and may receive the identifier and/or the preference of the individual. Alternatively, the processor may access or obtain the predefined preference of the individual. This information may allow the processor to selectively electrically couple the first electrical-connection node and the second electrical-connection node based on the identifier, the predefined preference of the individual and/or the preference of the individual. As noted previously, this approach may allow the environmental monitoring device to personalize the environmental condition based on who is in or is expected to be in the external environment.

In these ways, the environmental monitoring device may facilitate dynamic switching based on remote monitoring or measurements of one or more environmental conditions, the presence (or absence) of the individual and/or one or more preferences of the individual. Consequently, the environmental monitoring device may provide improved ways to monitor and modify the environmental conditions in the external environment. As illustrated in this discussion, at least some of the different embodiments of the environmental monitoring device may be used separately or in conjunction with each other, such as those described previously with reference to FIGS. 11-13.

Figure 18:
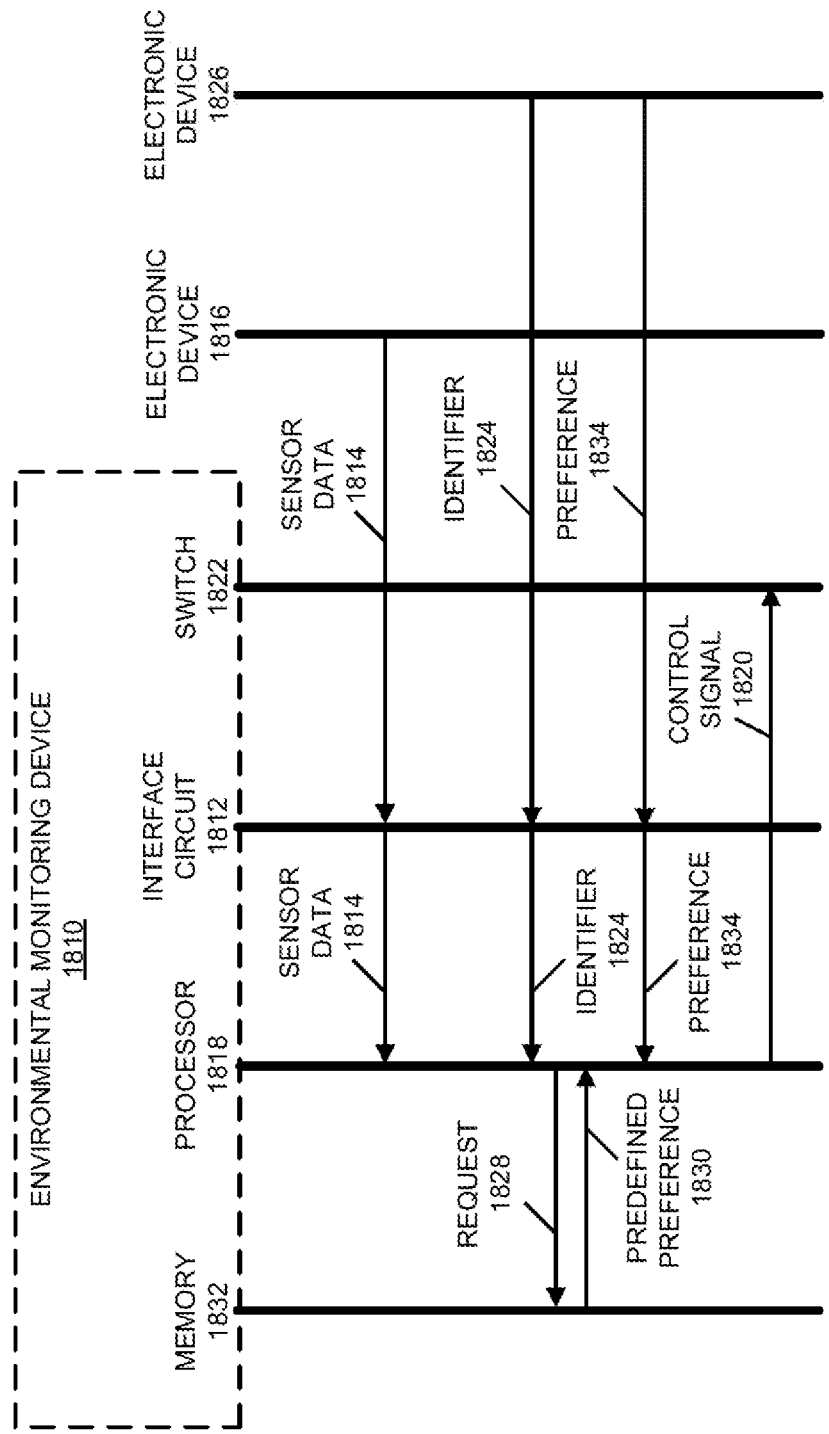
FIG. 18 is a drawing illustrating communication within an environmental monitoring device during the method of FIG. 17 in accordance with an embodiment of the present disclosure.

FIG. 18 presents a drawing illustrating communication within environmental monitoring device 1810 during method 1700 (FIG. 17). During operation of environmental monitoring device 1810 (such as during an environmentally gated switching mode of operation), interface circuit 1812 receives sensor data 1814 based on the one or more measurements of the environmental condition from electronic device 1816 (such as a legacy electronic device or another environmental monitoring device). Then, interface circuit 1812 provides sensor data 1814 to processor 1818.

Next, processor 1818 provides control signal 1820 to a switch 1822 to selectively electrically couple the first electrical-connection node and the second electrical-connection node in the environmental monitoring device based on the one or more measurements of the environmental condition.

In some embodiments, interface circuit 1812 optionally receives identifier 1824 from electronic device 1826 (such as the user's cellular telephone), and interface circuit 1812 then provides identifier 1824 to processor 1818. In response, processor 1818 may optionally access or obtain predefined preference 1830 from memory 1832 based on identifier 1824. For example, processor 1818 may receive predefined preference 1830 in response to request 1828. Alternatively, interface circuit 1812 may optionally receive preference 1834 from electronic device 1826 (for example, the user may provide preference 1834 using a user interface in electronic device 1826), which interface circuit 1812 then provides to processor 1818. Note that processor 1818 may optionally base control signal 1820 on: identifier 1824, predefined preference 1830 and/or preference 1834.

Figure 19:
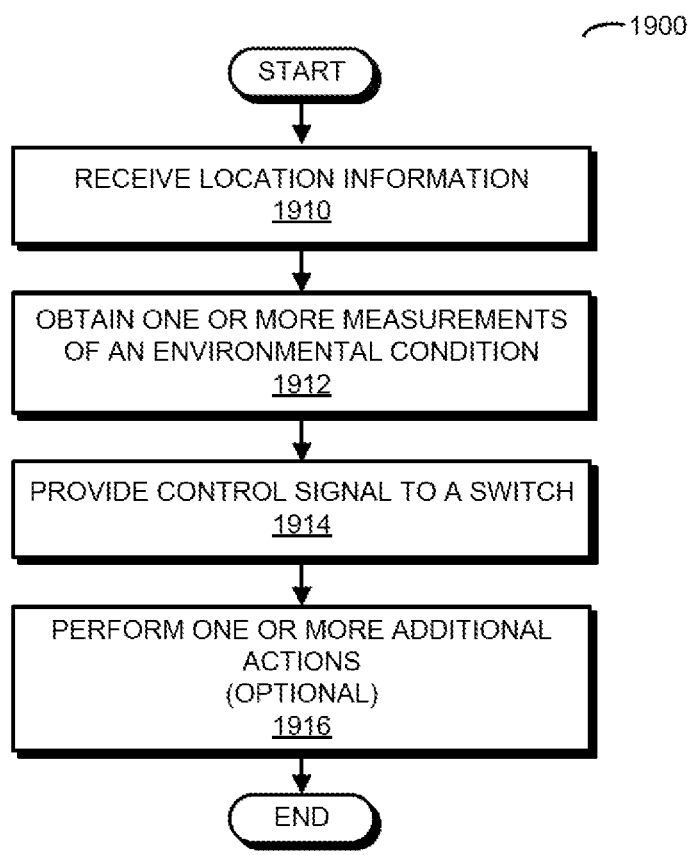
FIG. 19 is a flow diagram illustrating a method for selectively electrically coupling a first electrical-connection node and a second electrical-connection node in accordance with an embodiment of the present disclosure.

In some embodiments, the environmental monitoring device provides geo-fencing services. This is shown in FIG. 19, which presents a flow diagram illustrating a method 1900 for selectively electrically coupling the first electrical-connection node and the second electrical-connection node, which may be performed by the environmental monitoring device. During operation, the environmental monitoring device receives, from an electronic device (such as the third electronic device), the location information (operation 1910) of the individual. For example, the environmental monitoring device may receive the location information from the third electronic device (such as the user's cellular telephone), which is separate from the environmental monitoring device, via the antenna and the interface circuit.

Moreover, the environmental monitoring device may optionally obtain the one or more measurements of the environmental condition (operation 1912) in the external environment that includes the environmental monitoring device. For example, the sensor (or the sensor mechanism) in the environmental monitoring device may provide sensor data based on the one or more measurements of the environmental condition and/or the sensor data may be received from another electronic device that is separate from the environmental monitoring device (such as the fourth electronic device). In particular, the environmental monitoring device may communicate with the fourth electronic device via the antenna and the interface circuit, and this communication may include the sensor data. Note that the sensor may include: a temperature sensor, a humidity sensor, an acoustic sensor, a fire-detection sensor, a load-monitoring sensor, and/or a motion sensor.

Furthermore, the processor (or the control mechanism) in the environmental monitoring device provides the control signal to the switch (operation 1914) or the switching mechanism in the environmental monitoring device to selectively electrically couple the first electrical-connection node and the second electrical-connection node based on the one or more measurements of the environmental condition and the location information. For example, the selective electrical coupling may occur when the location information indicates that the individual is within a region, such as: a room or a building. This region may include the external environment.

Note that the location information may be based on triangulation and trilateration. For example, the location information may be based on: communication in a network (such as a cellular-telephone network or a wireless network), communication within a subset of a network (such as within 100 m of a network switch or within range of a wireless access point, e.g., within approximately 50-300 m), a local positioning system, and/or a Global Positioning System. Furthermore, the location information may specify the location of the individual in two dimensions and/or three dimensions. Thus, the location of the individual may be specified in a plane (such as on a location on a floor in a building) and/or the location of the individual may be specify the floor and the location on the floor. Additionally, the location information may include: an absolute position of the individual and/or a position of the individual relative to that of the environmental monitoring device (such as within 10, 20, 50, 100 or more feet of the environmental monitoring device).

In some embodiments, the processor optionally performs one or more additional actions (operation 1916) using the location information. For example, the processor may calculate, based on the location information, a predicted location of the individual and a time when the individual is estimated to be proximate to or at the location (such as when the environmental monitoring device determines that the individual will arrive at home or, alternatively, when the individual will leave their office for the location). In particular, the location information may specify a sequence of locations as a function of time and/or a velocity of the individual, which may allow the predictions and estimates to be calculated. Alternatively, the location information may specify a position of the individual along a predefined route, which may allow the predictions and estimates to be calculated based on traffic conditions, weather conditions, etc. Thus, the processor may estimate that the individual will be in a room in a building in ten minutes. Then, the selective electrical coupling may be based on the predicted location and the time. This may allow the environmental monitoring device to adjust or modify the environmental condition in a predictive manner (e.g., in advance), so that the environmental condition meets the individual's needs, e.g., the lights may be turned on (or off), the temperature or the humidity in a room may be increased (or decreased), an air filter may be turned on (or off), a meal may be heated or ready to eat, an electronic device (such as a computer) may be turned on (or off), the individual may be checked into a hotel, etc. Moreover, these changes to the environmental condition may occur without the individual taking an action when they arrive at or are proximate to the location.

To facilitate such predictive capability, the communication with the third electronic device may include an identifier (such as the identifier of the third electronic device and, more generally, an identifier of the individual). This information may allow the environmental monitoring device to know both the location and the identity of the individual (e.g., based on a listed owner or user of the third electronic device). For example, the information may include a MAC address, which can be assigned to a network-enabled electronic device, and the MAC address may be transmitted to a portion of the network (which may include an environmental monitoring device). Alternatively or additionally, a MAC address for a user's mobile device (such as their cellular telephone) can be registered with or associated with an environmental monitoring device, and the environmental monitoring device can query for the MAC address of the mobile device on a portion of the network. If the MAC address appears in the routing table of a switch or a wireless-network router, the environmental monitoring device may recognize that the user's mobile device is located within range of the environmental monitoring device (or within range of the wireless-network router), and the environmental monitoring device may use this information to turn on or off features that are to be enabled and/or disabled by a geo-fencing technique (such as software that turns on a fan when the user's mobile device appears on a wireless network in the user's home). Then, the processor may selectively electrically couple the first electrical-connection node and the second electrical-connection node based on the identifier. This may allow the environmental monitoring device to meet the individual's need. In particular, based on the identifier, the environmental monitoring device may access or obtain a predefined preference of the individual, such as information that specifies the desired environmental condition. Alternatively, the communication may include a preference of the individual, and the selective electrical coupling may be based on the preference. For example, the individual may provide the preference using a user interface in the third electronic device.

In these ways, the environmental monitoring device may facilitate dynamic switching based on the one or more environmental conditions, the location of the individual and/or one or more preferences of the individual. Consequently, the environmental monitoring device may provide improved ways to monitor and modify the environmental conditions in the external environment.

Figure 20:
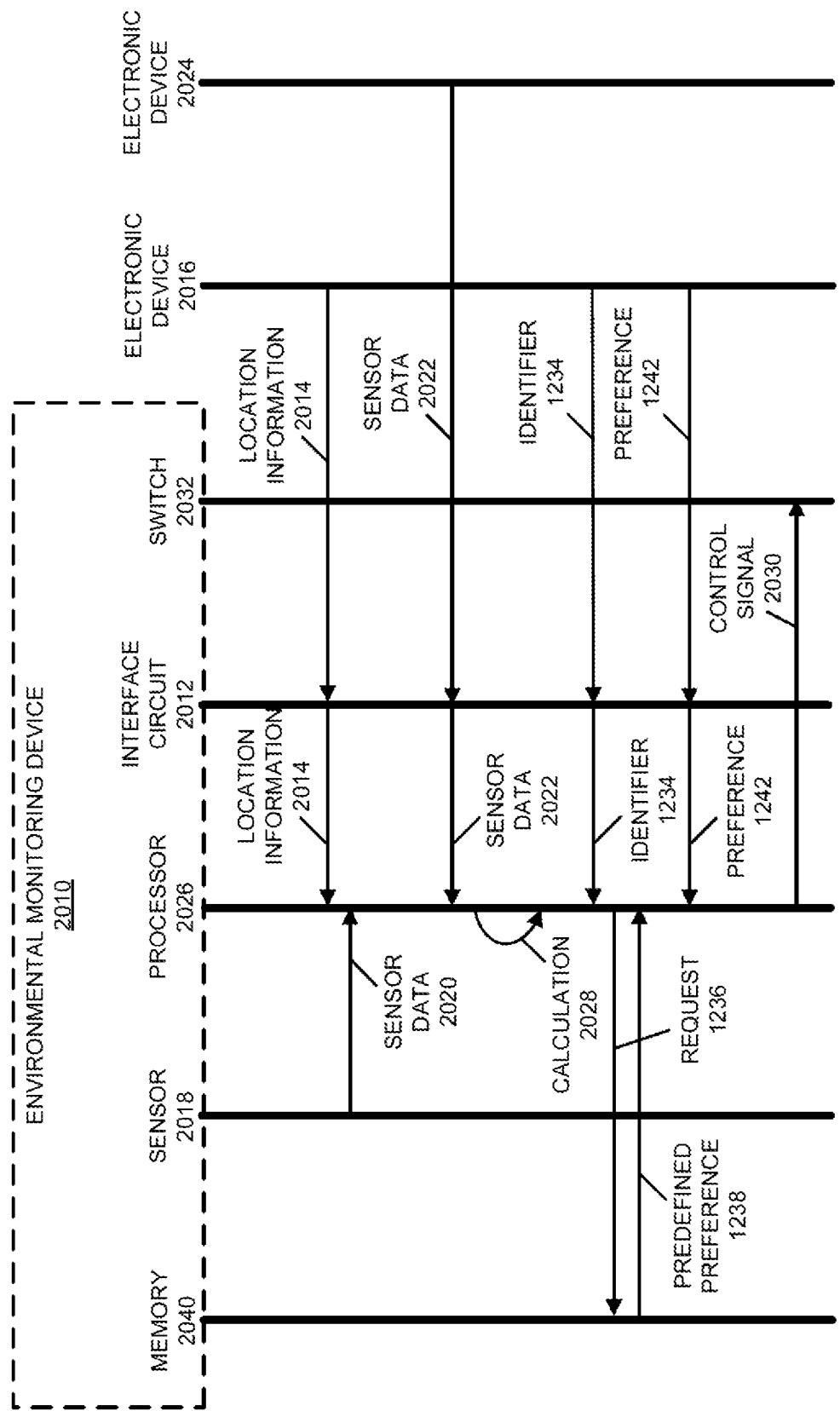
FIG. 20 is a drawing illustrating communication within an environmental monitoring device during the method of FIG. 19 in accordance with an embodiment of the present disclosure.

FIG. 20 presents a drawing illustrating communication within environmental monitoring device 2010 during method 1900 (FIG. 19). During operation of environmental monitoring device 2010 (such as during an environmentally gated switching mode of operation), interface circuit 2012 receives location information 2014 from electronic device 2016 (such as an individual's cellular telephone), and interface circuit 2012 provides location information 2014 to processor 2026.

Then, sensor 2018 optionally provides sensor data 2020 based on the one or more measurements of the environmental condition. Alternatively or additionally, interface circuit 2012 optionally receives sensor data 2022 based on the one or more measurements of the environmental condition from electronic device 2024 (such as a legacy electronic device or another environmental monitoring device), which is then provided to processor 2026.

Moreover, processor 2026 optionally performs a calculation 2028, such as calculating the estimated location and/or the arrival time based on location information 2014.

Next, processor 2026 provides control signal 2030 to switch 2032 to selectively electrically couple the first electrical-connection node and the second electrical-connection node in the environmental monitoring device based on the one or more measurements of the environmental condition, location information 2014 and/or calculation 2028.

In some embodiments, interface circuit 2012 optionally receives identifier 2034 from electronic device 2016, which is then provided to processor 2026. In response, processor 2026 may optionally access or obtain predefined preference 2038 from memory 2040 based on identifier 2034. For example, processor 2026 may receive predefined preference 2038 in response to request 2036. Alternatively, interface circuit 2012 may optionally receive preference 2042 from electronic device 2016 (for example, the user may provide preference 2042 using a user interface in electronic device 2016). Then, processor 2026 may optionally base control signal 2028 on: identifier 2034, predefined preference 2038 and/or preference 2042.

Figure 21:
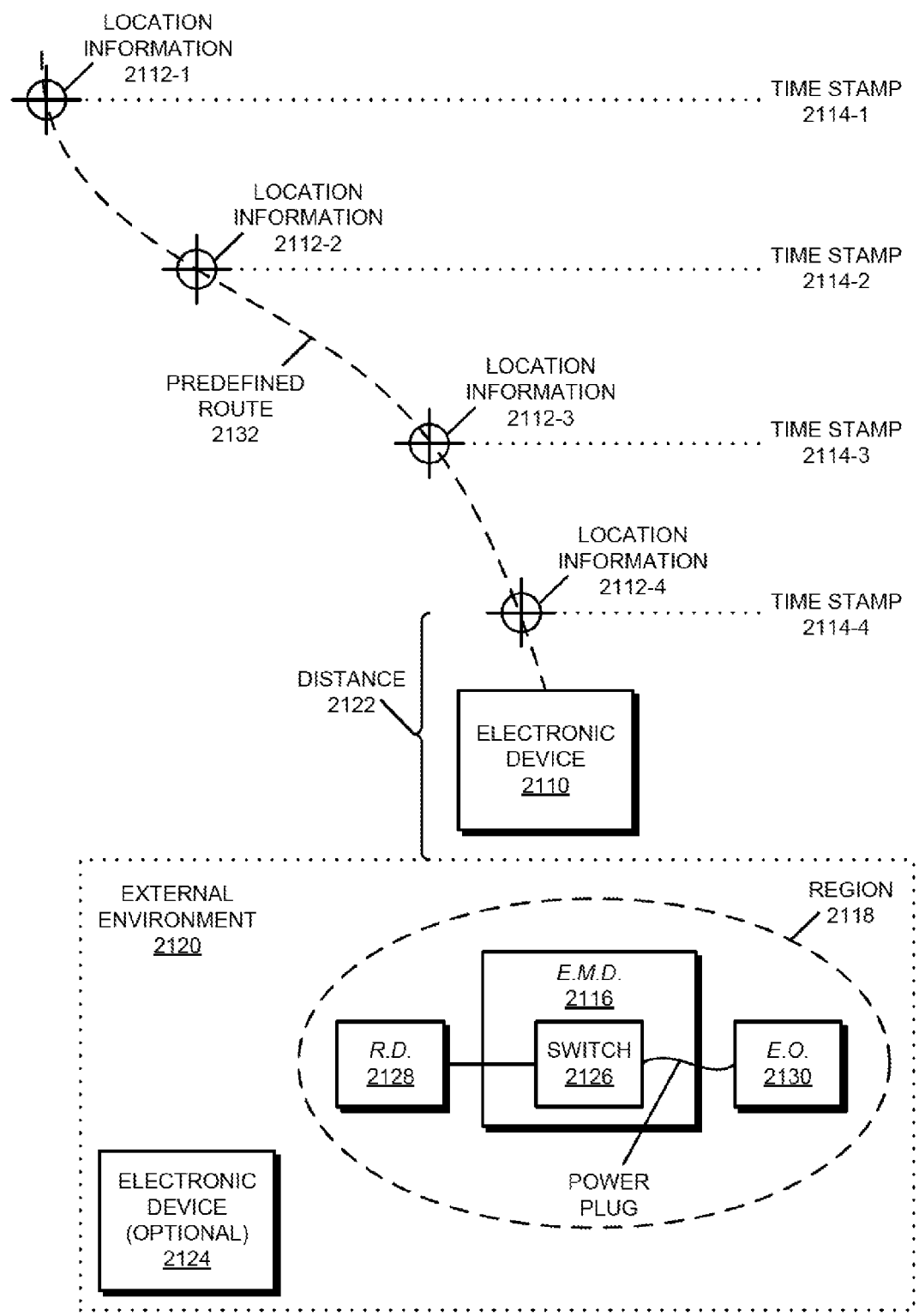
FIG. 21 is a drawing illustrating geo-fencing service in accordance with an embodiment of the present disclosure.

FIG. 21 presents a drawing illustrating a geo-fencing service. In particular, electronic device 2110 may provide location information 2112 at different times or time stamps 2114. This location information may be received by environmental monitoring device (E.M.D.) 2116, e.g., via wired and/or wireless communication. Using location information 2112, environmental monitoring device 2116 may estimate a location of electronic device 2110 at a future time, such as when electronic device 2110 (and, thus, a user or individual associated with electronic device 2110) is expected to be in region 2118 (such as a region in external environment 2120 that includes environmental monitoring device 2116). For example, subject to the constraints of the Nyquist sampling theorem, location information 2112 and associated time stamps 2114 may be used to calculate a velocity of electronic device 2110. Then, based on a distance 2122 between the most-recent instance of location information 2112 and region 2118, the estimated arrival time of electronic device 2110 at region 2118 may be calculated. Note that region 2118 may include a radius around a central location or region defined by an arbitrary set of boundaries or a perimeter (such as a room, a building, a residence, a school zone, a store, a warehouse, a work location, a commercial area, a neighborhood, etc.).

Moreover, environmental monitoring device 2116 may perform one or more measurements of the environmental condition in external environment 2120 and/or may receive one or more measurements of the environmental condition in external environment 2120 performed by optional electronic device 2124, e.g., via wired and/or wireless communication. Then, environmental monitoring device 2116 may selectively electrically couple (or selectively decouple) regulator device (R.D.) 2128 and power cord plugged into an electrical outlet (E.O.) 2130 (e.g., an AC power plug) using switch 2126. In this way, environmental monitoring device 2114 may regulate or modify the environmental condition without communication between environmental monitoring device 2114 and regulator device 2128.

In some embodiments, location information 2110 is along a predefined route 2132. In these embodiments, environmental monitoring device 2116 may use information about predefined route 2132 (such as a length of predefined route 2132), historical data (such as arrival times of the user or the individual at different times of the day, week, month or year based on the most-recent instance of location information 2110) and/or current conditions along predefined route 2132 (such as traffic conditions, weather conditions, etc.) to calculate the estimated arrival time at region 2118.

While the preceding example illustrated a geo-fencing service based on an estimated arrival time, in other embodiments geo-fencing is used to monitor whether the user or the individual is within region 2118. For example, a geo-fencing service may monitor whether a child is within region 2118. If the child leaves region 2118, environmental monitoring device 2116 may modify the selective electrical coupling provided by switch 2126. Thus, the geo-fencing service may be based on the individual being with region 2118 and/or outside of region 2118.

Figure 22:
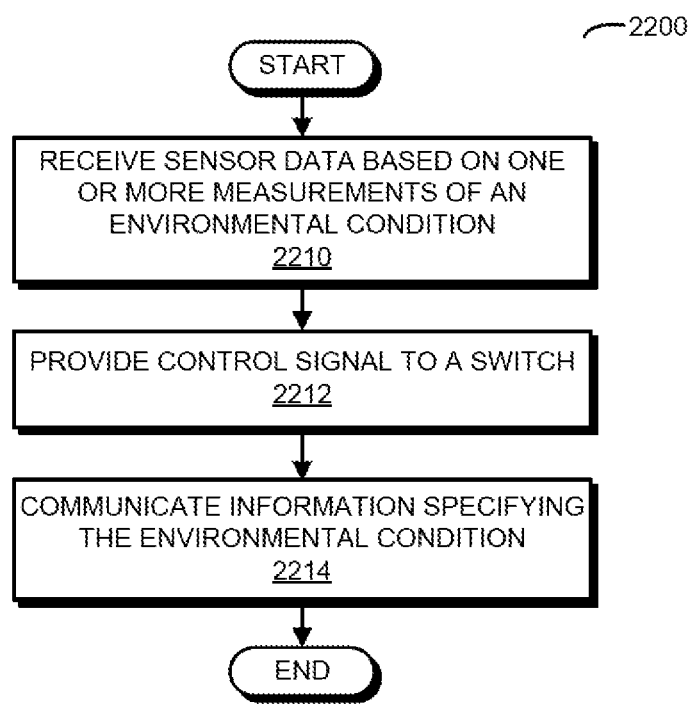
FIG. 22 is a flow diagram illustrating a method for selectively electrically coupling a first electrical-connection node and a second electrical-connection node in accordance with an embodiment of the present disclosure.

In some embodiments, the environmental monitoring device uses monitored energy usage or power consumption to control the selective electrical coupling. This is shown in FIG. 22, which presents a flow diagram illustrating a method 2200 for selectively electrically coupling the first electrical-connection node and the second electrical-connection node, which may be performed by the environmental monitoring device. During operation, the environmental monitoring device receives, from the sensor (or the sensor mechanism) in the environmental monitoring device, the sensor data (operation 2210) based on the one or more measurements of an environmental condition in the external environment that includes the environmental monitoring device. Note that the environmental condition may correspond to (or may be related to or a function of) power consumption by the electronic device that is separate from the environmental monitoring device, and that is electrically coupled to the first electrical-connection node. Alternatively or additionally, the environmental condition may correspond to (or may be related to or a function of) power consumption by the second electronic device that is separate from the environmental monitoring device, and that is electrically coupled to the second electrical-connection node.

Then, the processor (or the control mechanism) in the environmental monitoring device provides the control signal to the switch (operation 2212) or the switching mechanism in the environmental monitoring device to selectively electrically couple the first electrical-connection node and the second electrical-connection node based on the one or more measurements of the environmental condition.

Moreover, an antenna and an interface circuit in the environmental monitoring device may communicate information specifying the environmental condition (operation 2214) to another electronic device (such as the third electronic device and/or an electronic device associated with a power company, e.g., a power meter), which is separate from the environmental monitoring device. This capability may allow the environmental monitoring device to facilitate so-called 'smart monitoring' and/or 'smart regulation' of power consumption (such as dynamic regulation of demand based on a condition in a power system, e.g., the spot price of electricity, current demand, etc.) in the external environment (such as a home or building). Furthermore, this may allow reports about power consumption and/or total working time or the duration of usage to be sent to the user (such as the user's cellular telephone).

As noted previously, the environmental condition may include energy consumption and/or power consumption. Moreover, the environmental condition may indicate, during a time interval, usage of the electronic device and/or the second electronic device (such as whether or not the electronic device and/or the second electronic device were used, e.g., a binary usage metric). For example, the environment condition may indicate whether (or not) a mini-bar was used or whether (or not) an individual watched television. In some embodiments, the sensor data includes measurements of heat generated by the electronic device and/or the second electronic device. Alternatively or additionally, the environmental condition may indicate a duration of usage of the electronic device and/or the second electronic device, e.g., a real-valued usage metric. For example, how long the individual watched television. In these ways, the environmental monitoring device may monitor and report information that is equivalent to the power usage on a power meter and/or may monitor activities or actions of the individual. In addition, the environmental monitoring device may control the selective electrical coupling based on predefined constraints. Thus, the environmental monitoring device may electrically decouple a television after an allotted viewing time has been exceeded, or may electrically decouple the electronic device and/or the second electronic device when a predefined energy-consumption value is exceeded.

In some embodiments, the sensor includes a load-monitoring sensor and the environmental condition includes an electrical characteristic associated with the electronic device and/or the second electronic device. For example, the electrical characteristic may include: a current, a voltage, a phase relative to at least a reference signal, a quality factor, a harmonic of a fundamental frequency, a resonance frequency, a time constant, noise, and/or power consumption. Thus, the one or more measurements may directly measure the energy consumption and/or the power consumption, or the energy consumption and/or the power consumption may be determined indirectly (such as based on heat measurements, which can specify binary usage, and a predefined look-up table of the energy consumption and/or the power consumption of the electronic device and/or the second electronic device).

Moreover, the selective electrical decoupling may occur when the electrical characteristic indicates a safety concern (such as a fire hazard, a short circuit, a risk of electric shock or electrocution, etc.).

Furthermore, as described previously with reference to FIG. 15, the environmental condition may be associated with a power-up transient signal of the electronic device and/or the second electronic device. In particular, the electrical characteristic may include a time-varying power consumption of the electronic device and/or the second electronic device, where the time variation may include a sequence of approximately discrete values (such as two power-consumption levels or multiple power-consumption levels). Additionally, the electrical characteristic may correspond to (or be related to or a function of): a pulse-code modulation sequence, a quadrature-modulation sequence, and/or a DC-balanced sequence. In some embodiments, the power-consumption levels include information encoded with: an error-detection code, a parity-bit technique, a checksum, a hash function, a cyclic-redundancy check, a hamming code, and/or an error-correction code.

Note that the processor may determine information associated with the electronic device and/or the second electronic device based on the one or more measurements of the environmental condition during operation of the electronic device and/or the second electronic device. For example, the information may include: a type of electronic device, a model of electronic device, a brand of electronic device, and/or a unique identifier of the electronic device and/or the second electronic device. Furthermore, the processor may associate a user with the determined information based a predefined list of electronic devices of the user. Alternatively or additionally, the selective electrical coupling may be based on a predefined preference of the user or the individual. Thus, the predefined preference may indicate that the user (such as a child) can watch television for an hour per day. When the environmental condition indicates this has occurred, the environmental monitoring device may selectively electrically decouple the television from a power source.

Figure 23:
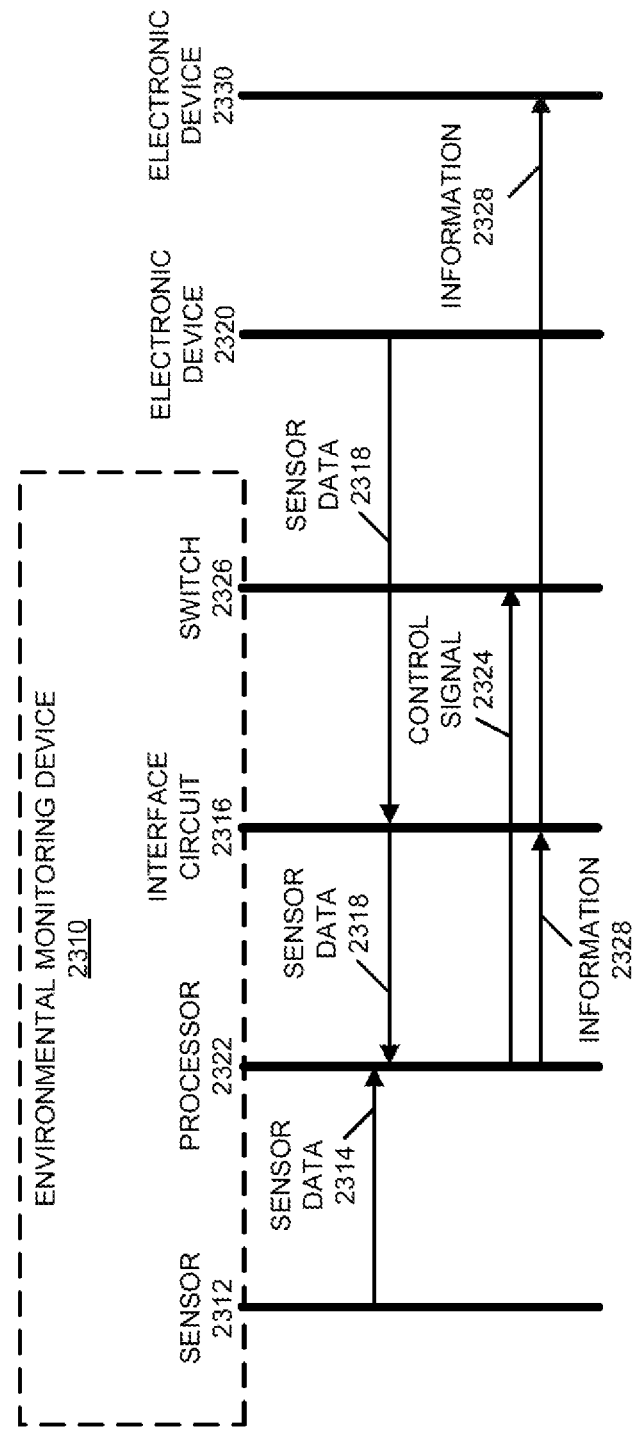
FIG. 23 is a drawing illustrating communication within an environmental monitoring device during the method of FIG. 22 in accordance with an embodiment of the present disclosure.

FIG. 23 presents a drawing illustrating communication within environmental monitoring device 2310 during method 2200 (FIG. 22). During operation of environmental monitoring device 2310 (such as during an environmentally gated switching mode of operation), sensor 2312 optionally provides sensor data 2314 based on the one or more measurements of the environmental condition to processor 2322. Alternatively or additionally, interface circuit 2316 optionally receives sensor data 2318 based on the one or more measurements of the environmental condition from electronic device 2320 (such as a legacy electronic device or another environmental monitoring device), and then provides sensor data 2318 to processor 2322. As noted previously, the environmental condition may include energy consumption and/or power consumption of the electronic device and/or the second electronic device.

Then, processor 2322 provides control signal 2324 to switch 2326 to selectively electrically couple the first electrical-connection node and the second electrical-connection node in the environmental monitoring device based on the one or more measurements of the environmental condition.

Moreover, processor 2322 provides information 2328 (which specifies the environmental condition) to interface circuit 2316, which communicates information 2328 to electronic device 2330 (such as a power meter).

Figure 24:
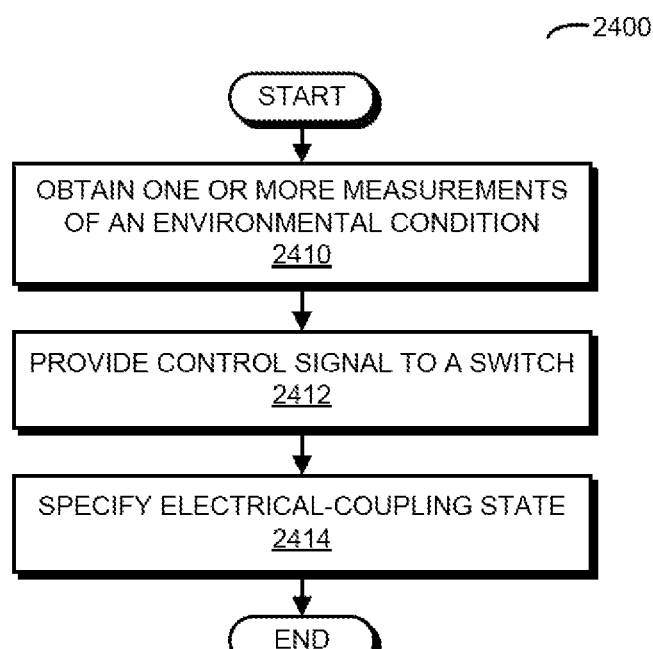
FIG. 24 is a flow diagram illustrating a method for selectively electrically coupling a first electrical-connection node and a second electrical-connection node in accordance with an embodiment of the present disclosure.

In some embodiments, the environmental monitoring device includes an override mechanism that provides the user control over whether (or not) there is selective electrical coupling or decoupling. This is shown in FIG. 24, which presents a flow diagram illustrating a method 2400 for selectively electrically coupling the first electrical-connection node and the second electrical-connection node, which may be performed by the environmental monitoring device. During operation, the environmental monitoring device obtains the one or more measurements of the environmental condition (operation 2410) in the external environment that includes the environmental monitoring device. For example, the sensor (or the sensor mechanism) in the environmental monitoring device may optionally provide sensor data based on the one or more measurements of the environmental condition and/or the sensor data may be optionally received from another electronic device that is separate from the environmental monitoring device (such as the fourth electronic device). In particular, the environmental monitoring device may communicate with the fourth electronic device via the antenna and the interface circuit, and this communication may include the sensor data. Note that the sensor may include: a temperature sensor, a humidity sensor, an acoustic sensor, a fire-detection sensor, a load-monitoring sensor, and/or a motion sensor.

Then, the processor (or the control mechanism) in the environmental monitoring device provides the control signal (operation 2412) to the switch (or the switching mechanism) in the environmental monitoring device to selectively electrically couple the first electrical-connection node and the second electrical-connection node based on the one or more measurements of the environmental condition.

Next, a user may use the manual-control or override mechanism in the environmental monitoring device to specify the electrical coupling state (operation 2414) of the first electrical-connection node and the second electrical-connection node, where the electrical coupling state specified by the override mechanism supersedes the selective electrical coupling specified by the control signal. Note that the override mechanism may supersede the selective electrical coupling either directly or indirectly. In particular, the override mechanism may be electrically coupled to the switch and/or the processor.

For example, a user of the environmental monitoring device may activate the override mechanism (such as by flipping an override switch or pushing an override button), which may pass through or skip all the digital aspects performed by the processor in operation 2414 and may force the electrical coupling state (such as electrical coupling or electrical decoupling of the first electrical-connection node and the second electrical-connection node). In particular, the override mechanism may have a first electrical coupling state and a second electrical coupling state, and may include an override switch and/or an override button. In a first electrical coupling state of the override mechanism, the first electrical-connection node and the second electrical-connection node may be electrically coupled, and in a second electrical coupling state of the override mechanism the first electrical-connection node and the second electrical-connection node may be electrically decoupled. The user may activate the override mechanism to select the first electrical coupling state or the second electrical coupling state.

In these ways, the environmental monitoring device may facilitate dynamic switching based on the one or more environmental conditions, while allowing the user the ability to assert control, as needed, of the selective electrical coupling of the switch (so that, for example, things just 'work' the way the user wants). Consequently, the environmental monitoring device may provide improved ways to monitor and modify the environmental conditions in the external environment in accordance with the user's wishes, thereby providing an improved user experience when using the environmental monitoring device.

Figure 25:
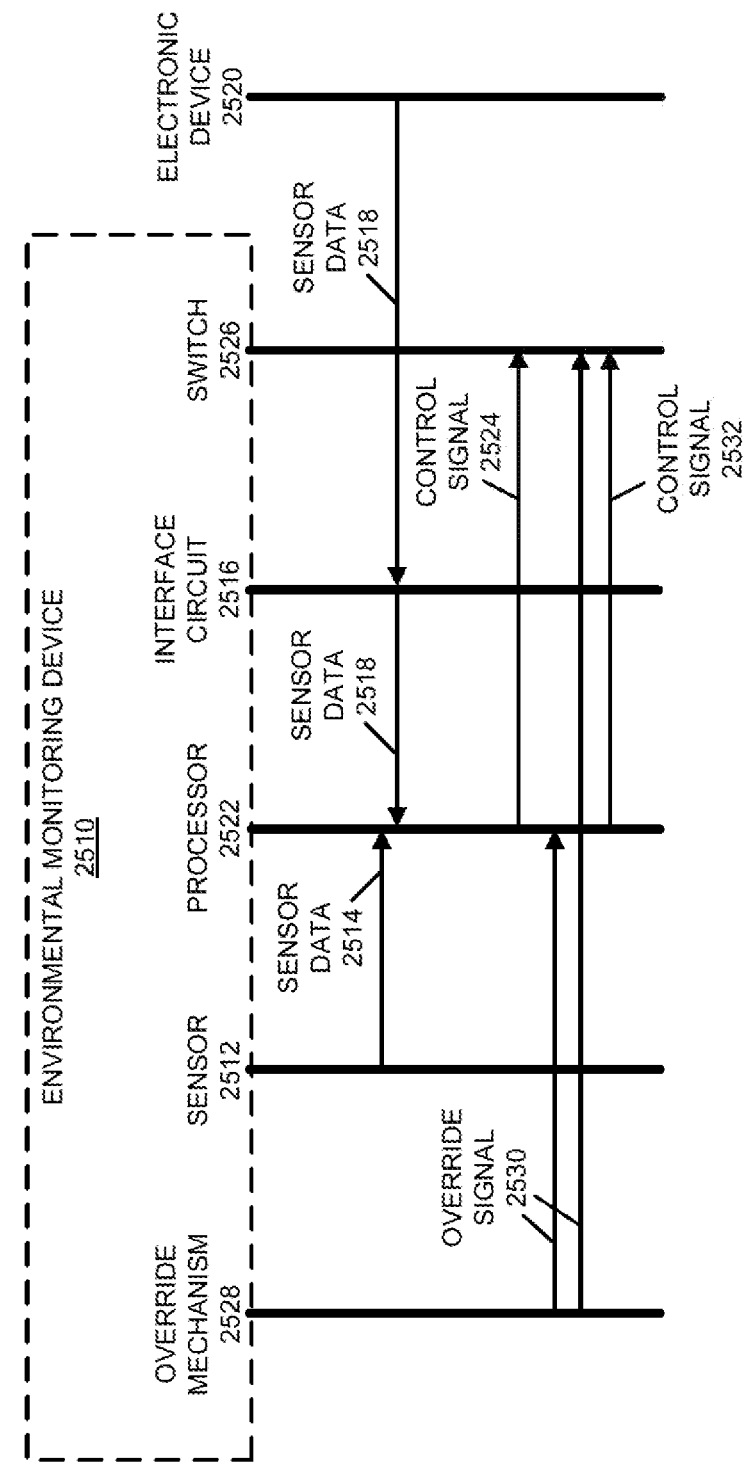
FIG. 25 is a drawing illustrating communication within an environmental monitoring device during the method of FIG. 24 in accordance with an embodiment of the present disclosure.

FIG. 25 presents a drawing illustrating communication within environmental monitoring device 2510 during method 2400 (FIG. 24). During operation of environmental monitoring device 2510 (such as during an environmentally gated switching mode of operation), sensor 2512 optionally provides sensor data 2514 based on the one or more measurements of the environmental condition to processor 2522. Alternatively or additionally, interface circuit 2516 optionally receives sensor data 2518 based on the one or more measurements of the environmental condition from electronic device 2520 (such as a legacy electronic device or another environmental monitoring device), which then provides sensor data 2518 to processor 2522.

Then, processor 2522 provides control signal 2524 to switch 2526 to selectively electrically couple the first electrical-connection node and the second electrical-connection node in the environmental monitoring device based on the one or more measurements of the environmental condition.

Moreover, based on a user action or instruction, override mechanism 2528 may provide override signal 2530 to processor 2522 and/or switch 2526 to specify the electrical coupling state of switch 2526. For example, when processor 2522 receives override signal 2530, control signal 2532 may optionally be accordingly modified. Alternatively or additionally, when switch 2526 optionally receives override signal 2530, the selective electrical coupling may optionally be accordingly modified (so that the first electrical-connection node and the second electrical-connection node are electrically coupled or electrically decoupled based on override signal 2530).

Figure 26:
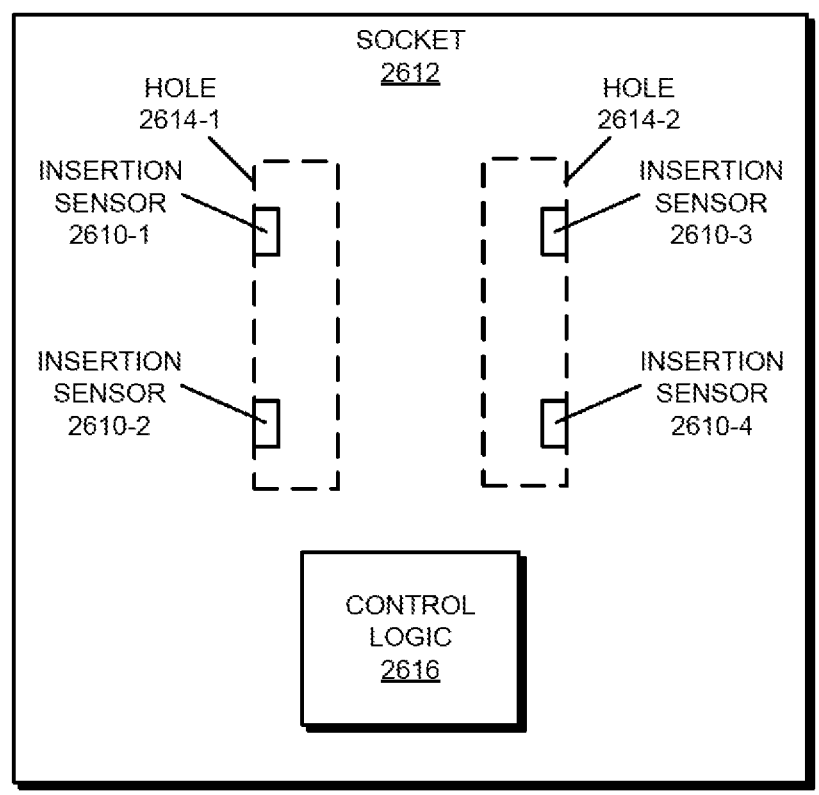
FIG. 26 is a drawing illustrating a safety sensor in the environmental monitoring device for safety monitoring in accordance with an embodiment of the present disclosure.

In some embodiments, the environmental monitoring device includes a safety mechanism that detects a safety condition and decouples the first electrical-connection node and the second electrical-connection node. This is shown in FIG. 26 presents a drawing illustrating a safety mechanism 2600 for safety monitoring in the environmental monitoring device. This safety mechanism may include one or more insertion sensors 2610 that detect insertion of an object other than a power plug into a socket 2612 associated with the first electrical-connection node and/or the second electrical-connection node. Moreover, the one or more insertion sensors 2610 may be passive and/or active. For example, the one or more insertion sensors 2610 may include: an optical detector, a pressure sensor (such as a spring or a tactile switch), a chemical sensor (which detects burning material), and/or an electrical sensor.

In particular, socket 2612 may have holes 2614, and the safety condition may involve detecting insertion of the object into hole 2614-1 without insertion of the object into hole 2614-2. For example, the optical detector may detect a blocked beam (between an optical source and a photodiode) in hole 2614-1 and not hole 2614-2. Alternatively, the electrical sensor may detect current between contacts in hole 2614-1 and not hole 2614-2. Furthermore, a spring (such as a sheet metal spring) in hole 2614-1 may be compressed, while a spring in hole 2614-2 may not be compressed. Note that the springs in holes 2614 may be position towards the top and the bottom of hole 2614 (as well as or instead of on the sides of holes 2614) so that an angular position of the object in holes 2614 may be determined.

In some embodiments, the detection of the insertion of the object into hole 2614-1 and the absence of detection of the insertion of the object into hole 2614-2 may be within a time interval. Thus, if the one or more insertion sensors 2610 simultaneously (or within a time window of a few milliseconds to several hundred milliseconds) detect the object in holes 2614, control logic 2616 in safety mechanism 2600 may conclude that the object is the power plug. This conclusion may be reinforced if the measured electrical resistance or conductivity (and, more generally, electrical impedance) of the object in holes 2614 matches that of the power plug.

Furthermore, the safety condition may involve detecting: insertion of the object into a hot contact associated with socket 2612 and/or a ground-fault current. For example, safety mechanism 2600 may include: a ground-fault circuit interrupter, a surge protector, a fuse and/or a short detector. These capabilities may allow safety mechanism 2600 to run a test prior to the switch selectively electrically coupling the first electrical-connection node and the second electrical-connection node. If the electronic device and/or the second electronic device fails this test (e.g., a safety condition is detected), the environmental monitoring device may not selectively electrically couple the first electrical-connection node and the second electrical-connection node.

Thus, safety mechanism 2600 may help ensure safe operation of the environmental monitoring device. For example, the environmental monitoring device may have a child-safety operating mode that may that the environmental monitoring device can be used in environments in which children may inadvertently attempt to stick objects in either or both of holes 2614 without the occurrence of a safety concern (such as a risk of electric shock, a short circuit, a fire hazard and, more generally, a dangerous condition that can result in injury). This may allow environmental monitoring device to be safely used in these external environments, e.g., in conjunction with or as a night light.

In some embodiments of one or more of the preceding methods, there may be additional or fewer operations. Furthermore, the order of the operations may be changed, and/or two or more operations may be combined into a single operation. In addition, in some of the preceding embodiments there are fewer components, more components, a position of a component is changed and/or two or more components are combined.

In the preceding description, we refer to 'some embodiments.' Note that 'some embodiments' describes a subset of all of the possible embodiments, but does not always specify the same subset of embodiments.

The foregoing description is intended to enable any person skilled in the art to make and use the disclosure, and is provided in the context of a particular application and its requirements. Moreover, the foregoing descriptions of embodiments of the present disclosure have been presented for purposes of illustration and description only. They are not intended to be exhaustive or to limit the present disclosure to the forms disclosed. Accordingly, many modifications and variations will be apparent to practitioners skilled in the art, and the general principles defined herein may be applied to other embodiments and applications without departing from the spirit and scope of the present disclosure. Additionally, the discussion of the preceding embodiments is not intended to limit the present disclosure. Thus, the present disclosure is not intended to be limited to the embodiments shown, but is to be accorded the widest scope consistent with the principles and features disclosed herein.

What is claimed is:

1. An environmental monitoring device, comprising:
    a first electrical-connection node configured to electrically couple to an electronic device that includes a power source;
    a second electrical-connection node configured to electrically couple to a second electronic device that includes a rechargeable battery;
    a switching mechanism, electrically coupled to the first electrical-connection node and the second electrical-connection node, configured to selectively electrically couple the first electrical-connection node and the second electrical-connection node;
    a sensor mechanism that provides sensor data based on the one or more measurements of an environmental condition in an external environment that includes the environmental monitoring device, wherein the environmental condition is associated with charging of the rechargeable battery; and
    a control mechanism, electrically coupled to the switching mechanism and the sensor mechanism, configured to:
        provide a control signal to the switching mechanism to selectively electrically couple the first electrical-connection node and the second electrical-connection node based on the one or more measurements of the environmental condition;
        select a charging mode of the rechargeable battery based on the one or more measurements of the environmental condition; and
        predict failure of at least a component in one of the electronic device and the second electronic device based on the one or more measurements of the environmental condition as a function of time.

2. The environmental monitoring device of claim 1, wherein the charging mode includes one of: a charging profile as a function of time that increases life of the rechargeable battery, a charging profile as a function of time that reduces a charging, time of the rechargeable battery, a charging profile as a function of time that reduces power consumption while charging the rechargeable battery.

3. The environmental monitoring device of claim 1, wherein the control mechanism is configured determine information associated with one of the electronic device and the second electronic device based on the one or more measurements of the environmental condition during operation of the one of the electronic device and the second electronic device; and
    wherein the predicted failure is based on the determined information.

4. The environmental monitoring device of claim 3, wherein the environmental condition is associated with a power-up transient signal of one of: the electronic device, and the second electronic device.

5. The environmental monitoring device of claim 3, wherein the information includes one of: a type of electronic device, a model of electronic device, a brand of electronic device, and a unique identifier of the one of the electronic device and the second electronic device.

6. The environmental monitoring device of claim 1, wherein the control mechanism is configured determine information associated with one of the electronic device and the second electronic device based on the one or more measurements environmental condition during operation of the one of the electronic device and the second electronic device.

7. The environmental monitoring device of claim 6, wherein the control mechanism is configured to associate a user with the determined information based a predefined list of electronic devices of the user.

8. The environmental monitoring device of claim 7, wherein the selective electrical coupling of the first electrical-connection node and the second electrical-connection node is based on a predefined preference of the user.

9. The environmental monitoring device of claim 6, wherein the environmental condition is associated with a power-up transient signal of one of: the electronic, device, and the second electronic device.

10. The environmental monitoring device of claim 6, wherein the information includes one of: a type of electronic device, a model of electronic device, a brand of electronic device, and a unique identifier of the one of the electronic device and the second electronic device.

11. The environmental monitoring device of claim 10, wherein the determining is based on a predefined device profile.

12. The environmental monitoring device of claim 1, wherein the sensor mechanism includes a load-monitoring sensor and the environmental condition includes an electrical characteristic associated with one of the electronic device, and the second electronic device.

13. The environmental monitoring device of claim 12, wherein the electrical characteristic includes one of a current, a voltage, a phase relative to at least a reference signal, a quality factor, a harmonic of a fundamental frequency, a resonance frequency, a time constant, noise, and power consumption.

14. The environmental monitoring device of claim 12, wherein the control mechanism is configured to selectively electrically decouple the first electrical-connection node from the second electrical-connection node when the electrical characteristic indicates a standby operating mode for the one of the electronic device, and the second electronic device.

15. The environmental monitoring device of claim 12, wherein the control mechanism is configured to selectively electrically decouple the first electrical-connection node from the second electrical-connection node when the electrical characteristic indicates a safety concern.

16. The environmental monitoring device of claim 15, wherein the safety concern includes one of: a risk of electric shock, a short circuit, and a fire hazard.

17. A computer-program product for use in conjunction with an environmental monitoring device, the computer-program product comprising a non-transitory computer-readable storage medium and a computer-program mechanism embedded therein to selectively electrically couple a first electrical-connection node and a second electrical-connection node, the computer-program mechanism including:
  instructions for receiving sensor data based on one or more measurements of an environmental condition from a sensor mechanism in the environmental monitoring device, wherein the environmental condition is associated with charging of a rechargeable battery;
  instructions for providing a control signal to a switching mechanism in the environmental monitoring device to selectively electrically couple the first electrical-connection node and the second electrical-connection node based on the one or more measurements of the environmental condition;
  instructions for selecting a charging mode of the rechargeable battery based on the one or more measurements of the environmental condition; and
  instructions for predicting failure of at least a component in one of the electronic device and the second electronic device based on the one or more measurements of the environmental condition as a function of time.

18. The computer-program product of claim 17, wherein charging mode includes one of: a charging profile as a function of time that increases life of the rechargeable battery, a charging profile as a function of time that reduces a charging time of the rechargeable battery, a charging profile as a function of time that reduces power consumption while charging the rechargeable battery.

19. A control-mechanism-implemented method for selectively electrically coupling, a first electrical-connection node and a second electrical-connection node in an environmental monitoring device, wherein the method comprises:
  receiving sensor data based on one or more measurements of an environmental condition from a sensor mechanism in the environmental monitoring device, wherein the environmental condition is associated with charging of a rechargeable battery;
  using the control mechanism in the environmental monitoring device, providing a control signal to a switching mechanism in the environmental monitoring device to selectively electrically couple the first electrical-connection node and the second electrical-connection node based on the one or more measurements of the environmental condition;
  selecting a charging mode of the rechargeable battery based on the one or more measurements of the environmental condition; and
  predicting, failure of at least a component in one of the electronic device and the second electronic device based on the one or more measurements of the environmental condition as a function of time.

20. An environmental monitoring device, comprising:
  a first electrical-connection node configured to electrically couple to an electronic device that includes a power source;
  a second electrical-connection node configured to electrically couple a second electronic device that includes a rechargeable battery;
  a switching mechanism, electrically coupled to the first electrical-connection node and the second electrical-connection node, configured to selectively electrically couple the first electrical-connection node and the second electrical-connection node;
  a sensor mechanism that provides sensor data based on the one or more measurements of an environmental condition in an external environment that includes the environmental monitoring device, wherein the environmental condition is associated with charging of the rechargeable battery; and
  a control mechanism, electrically coupled to the switching mechanism and the sensor mechanism, configured to:
    provide a control signal to the switching mechanism to selectively electrically couple the first electrical-connection node and the second electrical-connection node based on the one or more measurements of the environmental condition;
    select a charging mode of the rechargeable battery based on the one or more measurements of the environmental condition;
    determine information associated with one of the electronic device and the second electronic device based on the one or more measurements environmental condition during operation of the one of the electronic device and the second electronic device; and
    associate a user with the determined information based a predefined list of electronic devices of the user.

21. A computer-program product for use in conjunction with an environmental monitoring device, the computer-program product comprising a non-transitory computer-readable storage medium and a computer-program mechanism embedded therein to selectively electrically couple a first electrical-connection node and a second electrical-connection node, the computer-program mechanism including:
- instructions for receiving sensor data based on one or more measurements of an environmental condition from a sensor mechanism in the environmental monitoring device, wherein the environmental condition is associated with charging of a rechargeable battery;
- instructions for providing a control signal to a switching mechanism in the environmental monitoring device to selectively electrically couple the first electrical-connection node and the second electrical-connection node based on the one or more measurements of the environmental condition;
- instructions for selecting a charging mode of the rechargeable battery based on the one or more measurements of the environmental condition;
- instructions for determining information associated with one of the electronic device and the second electronic device based on the one or more measurements environmental condition during operation of the one of the electronic device and the second electronic device; and
- instructions for associating a user with the determined information based a predefined list of electronic devices of the user.

22. A control-mechanism-implemented method for selectively electrically coupling a first electrical-connection node and a second electrical-connection node in an environmental monitoring device, wherein the method comprises:
- receiving sensor data based on one or more measurements of an environmental condition from a sensor mechanism in the environmental monitoring device, wherein the environmental condition is associated with charging of a rechargeable battery;
- using the control mechanism in the environmental monitoring device, providing a control signal to a switching mechanism in the environmental monitoring device to selectively electrically couple the first electrical-connection node and the second electrical connection node based on the one or more measurements of the environmental condition;
- selecting a charging mode of the rechargeable battery based on the one or more measurements of the environmental condition;
- determining information associated with one of the electronic device and the second electronic device based on the one or more measurements environmental condition during operation of the one of the electronic device and the second electronic device; and
- associating a user with the determined information based a predefined list of electronic devices of the user.

* * * * *